United States Patent [19]

Couture et al.

[11] Patent Number: 5,705,388
[45] Date of Patent: Jan. 6, 1998

[54] CETP RIBOZYMES

[75] Inventors: Larry Couture, Louisville; Dan Stinchcomb; James McSwiggen, both of Boulder, all of Colo.; Charles Bisgaier; Michael Pape, both of Ann Arbor, Mich.

[73] Assignees: Ribozyme Pharmaceuticals, Inc., Boulder, Colo.; Warner-Lambert Company, Ann Arbor, Mich.

[21] Appl. No.: 363,240

[22] Filed: Dec. 23, 1994

[51] Int. Cl.$^6$ .............................. C12N 15/85; C12Q 1/68
[52] U.S. Cl. ...................... 435/366; 435/6; 435/91.31; 435/172.3; 435/320.1; 435/325; 536/23.1; 536/23.2; 536/24.5; 514/44
[58] Field of Search .................. 435/6, 91.31, 172.3, 435/325, 366, 320.1; 536/23.1, 23.2, 24.5; 514/44

[56] References Cited

U.S. PATENT DOCUMENTS

| | | | |
|---|---|---|---|
| 4,987,071 | 1/1991 | Cech et al. | 536/23.1 |
| 5,279,540 | 1/1994 | Davidson | 604/4 |

FOREIGN PATENT DOCUMENTS

| | | |
|---|---|---|
| 0360257 | 3/1990 | European Pat. Off. . |
| 0519463 | 12/1992 | European Pat. Off. . |
| 9103162 | 3/1991 | WIPO . |
| 9207065 | 4/1992 | WIPO . |
| 9311782 | 6/1993 | WIPO . |
| 9315187 | 8/1993 | WIPO . |
| 9323569 | 11/1993 | WIPO . |
| 9402595 | 2/1994 | WIPO . |

OTHER PUBLICATIONS

Gerwitz et al. PNAS 93: 3161–3163, 1996.
Rojanasakul et al. Adv. Drug Delivery Reviews 18:115–131, 1996.
Stull et al. Pharm. Res. 12: 465–483 (1995).
Abbey et al., "Effects of blocking plasma lipid transfer protein activity in the rabbit," *Biochim. Biophys. Acta* 1003:20 (1989).
Agellon et al., "Organization of the Human Cholesteryl Ester Transfer Protein Gene," *Biochemistry* 29:1372 (1990).
Bailey, "Lipid Metabolism in Cultured Cells," *Exp. Cell Res.* 37:175–182 (1965).
Barr et al., "Protein–lipid Relationships in Human Plasma," *Amer. J. Med.* 11:480 (1951).
Beisiegel et al., "The LDL–related protein, LRP, is an apolipoprotein E–binding protein," *Nature* 341:162 (1989).
Brown et al., "Molecular basis of lipid transfer protein deficiency in a family with increased high–density lipoproteins," *Nature* 342:448–451 (1989).
Carter, "Adeno–Associated Virus Vectors," *Curr Opi. Biotech.* 3:533–539 (1992).
Chen et al., "Multitarget–Ribozyme Directed to Cleave at up to Nine Highly Conserved HIV–1 env RNA Regions Inhibits HIV–1 Replication–Potential Effectiveness Against Most PresentlySequenced HIV–1 Isolates," *Nucleic Acids Research* 20:4581–4589 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).
Chowrira and Burke, "Extensive Phosphorothioate Substitution Yields Highly Active and Nuclease–Resistant Hairpin Ribozymes," *Nucleic Acids Res.* 20:2835–2840 (1992).
Collins and Olive, "Reaction Conditions and Kinetics of Self–Cleavage of a Ribozyme Derived from Neurospora VS RNA," *Biochemistry* 32:2795–2799 (1993).
Davignon et al., "Apolipoprotein E Polymorphism and Atherosclerosis," *Arteriosclerosis* 8:1 (1988).
Drayna et al., "Cloning and sequence of human cholesteryl ester transfer protein cDNA," *Nature* 327:632 (1987).
Dropulic et al., "Functional Characterization of a U5 Ribozyme: Intracellular Suppression of Human Immunodeficiency Virus Type I Expression," *Journal of Virology* 66:1432–1441 (1992).
Duval–Valentin, "Specific inhibition of transcription by triple helix–forming oligonucleotides," *Proc. Natl. Acad. Sci. USA* 89:504 (1992).
Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).
Evans et al., "Inhibition of cholesteryl ester transfer protein in normochoesterolemic and hypercholesterolemic hamsters: effects of HDL subspecies, quantity and apolipoprotein distribution," *J. Lipid Res.* 35:1634 (1994).
Expert Panel, "Report of the National Cholesterol Education Program Expert Panel on Detection, Evaluation, and Treatment of High Blood Cholesterol in Adults," *Arch Intern. Med.* 148:36 (1988).
Gao and Huang, "Cytoplasmic Expression of a Reporter Gene by Co–Delivery of T7 RNA Polymerase and T7 Promoter Sequence with Cationic Liposomes," *Nucleic Acids Res.* 21:2867–2872 (1993).
Goldstein et al., "Receptor–mediated Endocytosis: Concepts Emerging from the LDL Receptor System," *Ann Rev. Cell Biol.* 1:1 (1985).
Groener et al., "Effect of lipid transfer protein on plasma lipids, apolipoproteins, and metabolism of high–density lipoprotein cholesteryl ester in the rat," *Biochem. Biophys. Acta* 1002:93 (1989).
Grundy et al., "The Place of HDL in Cholesterol Management," *Arch. Intern. Med.* 149:505 (1989).
Guerrier–Takada et al., "The RNA Moiety of Ribonuclease P Is the Catalytic Subunit of the Enzyme," *Cell* 35:849–857 (1983).
Ha et al., "Effects of injecting exogenous lipid transfer protein into rats," *Biochim. Biophys. Acta* 833A:203 (1985).

(List continued on next page.)

*Primary Examiner*—John L. LeGuyader
*Attorney, Agent, or Firm*—Lyon & Lyon LLP

[57] ABSTRACT

A nucleic acid molecule which blocks synthesis and/or expression of mRNAs associated with initial development, progression or regression of vascular disease.

14 Claims, 6 Drawing Sheets

OTHER PUBLICATIONS

Hampel et al., "'Hairpin' Catalytic RNA Model: Evidence for Helices and Sequence Requirement for Substrate RNA," *Nucleic Acids Research* 18:299–304 (1990).

Hampel and Tritz, "RNA Catalytic Properties of the Minimum (–)sTRSV Sequence," *Biochemistry* 28:4929–4933 (1989).

Haseloff and Gerlach, "Simple RNA Enzymes with New and Highly Specific Endoribonuclease Activities," *Nature* 334:585–591 (1988).

Hertel et al., "Numbering System for the Hammerhead," *Nucleic Acids Res.* 20:3252 (1992).

Hirano et al., "Frequency of intron 14 splicing defect of cholesteryl ester transfer protein gene in the Japanese general population—relation between the mutation and hyperalphalipoproteineima," *Atherosclerosis* 100:85 (1993).

Hulley et al., "HDL–Cholesterol Levels in the Multiple Risk Factor Intervention Trial (MRFIT) by the MRFIT Research Group[1,2]," *Lipids* 14:119–125 (1978).

Inazu et al., "Alternative Splicing of the mRNA Encoding the Human Cholesteryl Ester Transfer Protein," *Biochemistry* 31:2352 (1991).

Inazu et al., "Enhanced Cholesteryl Ester Transfer Protein Activities and Abnormalities of High Density Lipoproteins in Familial Hypercholesterolemia," *Horm. Metab. Res.* 24:284 (1992).

Jaeger et al., "Improved Predictions of Secondary Structures for RNA," *Proc. Natl. Acad. Sci. USA* 86:7706–7710 (1989).

Jeffries and Symons, "A Catalytic 13–mer Ribozyme," *Nucleic Acids Research* 17:1371–1377 (1989).

Kannel et al., "Serum Cholesterol, Lipoproteins, and the Risk of Coronary Heart Disease," *Ann. Intern. Med.* 74:1 (1971).

Kashani–Sabet et al., "Reversal of the Malignant Phenotype by an Anti–ras Ribozyme," *Antisense Research & Development* 2:3–15 (1992).

Koizumi et al., "Deficiency of Serum Cholesteryl–Ester Transfer Activity in Patients with Familial Hyperalphalipoproteinaemia," *Atherosclerosis* 58:175 (1985).

Koizumi et al., "Serum lipoprotein lipid concentration and composition in homozygous and heterozygous patients with cholesteryl ester transfer protein deficiency," *Atherosclerosis* 90:189 (1991).

L'Huillier et al., "Cytoplasmic Delivery of Ribozymes Leads to Efficient Reduction in α–Lactalbumin mRNA Levels in C1271 Mouse," *Embo J.* 11:4411–4418 (1992).

Lagrost, "Influence of Apolipoprotein Composition of High Density Lipoprotein Particles on Cholesteryl Ester Transfer Protein Activity," *J. Biol. Chem.* 269:31893197 (1994).

Levy et al., "The influence of changes in lipid values induced by cholestyramine and diet on progression of coronary artery disease: results of the NHLBI Type II Coronary Intervention Study," *Circulation* 69:325 (1984).

Lieber et al., "Stable High–Level Gene Expression in Mammalian Cells by T7 Phage RNA Polymerase," *Methods Enzymol.* 217:47–66 (1993).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Lusis et al., "Assignment of the Human Gene for Cholesteryl Ester Transfer Protein to Chromosome 16q12–16q21," *Genomics* 1:232 (1987).

Mahley, "Apolipoprotein E: Cholesterol Transport Protein with Expanding Role in Cell Biology," *Science* 240:622 (1988).

Marotti et al., "The Role of Cholesteryl Ester Transfer Protein in Primate Apolipoprotein A–1 Metabolism," *Arterioscler. Thrombosis* 12:736 (1992).

McPherson et al., "Plasma Concentrations of Cholesteryl Ester Transfer Protein in Hyperlipoproteinemia," *Arterioscler. Thromb.* 11:797 (1991).

Melchior et al., "Apolipoprotein A–1 Metabolism in Cholesteryl Ester Transfer Protein Transgenic Mice," *J. Biol. Chem.* 269:8044–8051 (1994).

Milligan and Uhlenbeck, "Synthesis of Small RNAs Using T7 RNA Polymerase," *Methods Enzymol.* 180:51–62 (1989).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Pape et al., "Molecular Cloning, Sequence, and Expression of Cynomolgus, Monkey Cholesteryl Ester Transfer Protein," *Arterioscler. Thromb.* 11:1759 (1991).

Pattnaik et al., "Cholesteryl Ester Exchange Protein in Human Plasma Isolation and Characterization," *Biochem. Biophys. Acta* 530:428 (1978).

Pederson et al., "Randomised trail of cholesterol lowering in 4444 patients with coronary heart disease: the Scandinavian Simvastatin Survival Study," *Lancet* 344:1383 (1994).

Perreault et al., "Mixed Deoxyribo– and Ribo–Oligonucleotides with Catalytic Activity," *Nature* 344:565–567 (1990).

Perrotta and Been, "Cleavage of Oligoribonucleotides by a Ribozyme Derived from the Hepatitis δ Virus RNA Sequence," *Biochemistry* 31:16–21 (1992).

Pieken et al., "Kinetic Characterization of Ribonuclease–Resistant 2'–Modified Hammerhead Ribozymes," *Science* 253:314–317 (1991).

Plump et al., "Severe Hypercholesterolemia and Atherosclerosis in Apolipoprotein E–Deficient Mice Created by Homologous Recombination in ES Cells," *Cell* 71:343 (1992).

Plump et al., "Human apolipoprotein A–1 gene expression increases high density lipoprotein and supresses atherosclerosis in the apolipoprotein E–deficient mouse," *Proc. Natl. Acad. Sci. USA* 91:9607 (1994).

Quinet et al., "Inhibition of the Cellular Secretion of Cholesteryl Ester Transfer Protein by a Variant Protein Formed by Alternative Splicing of mRNA," *J. Biol. Chem.* 268:16891 (1993).

Reaven et al., "Role of Insulin Resistance in Human Disease," *Diabetes* 37:1595 (1988).

Rossi et al., "Ribozymes as Anti–HIV–1 Therapeutic Agents: Principles, Applications, and Problems," *Aids Research and Human Retroviruses* 8:183–189 (1992).

Sarver et al., "Catalytic RNAs (Ribozymes): A New Frontier in Biomedical Applications," *AIDS Res. Revs.* 2:259 (1992).

Saville and Collins, "A Site–Specific Self–Cleavage Reaction Performed by a Novel RNA In *Neurospora mitochondria*," *Cell* 61:685–696 (1990).

Saville and Collins, "RNA–Mediated Ligation of Self–Cleavage Products of a Neurospora Mitochondrial Plasmid Transcript," *Proc. Natl. Acad. Sci. USA* 88:8826–8830 (1991).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Tall et al., "Plasma cholesteryl ester transfer protein," *J. Lipid. Res.* 34:1255 (1993).

Torrence et al., "Targeting RNA for degradation with a (2'–5') oligodenylate–antisense chimera," *Proc. Natl. Acad. Sci. USA* 90:1300 (1993).

Uhlenbeck, "A Small Catalytic Oligoribonucleotide," *Nature* 328:596–600 (1987).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule on an *Escherichia coli* Formylmethoionine tRNA," *J. Am. Chem. Soc.* 109:7845–7854 (1987).

Usman and Cedergren, "Exploiting the chemical synthesis of RNA," *TIBS* 17:334–339 (1992).

Ventura et al., "Activation of HIV–Specific Ribozyme Activity by Self–Cleavage," *Nucleic Acids Research* 21:3249–3255 (1993).

Walden et al., "Apolipoprotein E in Hyperlipidemia," *Ann Intern. Med.* 120:1026 (1994).

Weerasinghe et al., "Resistance to Human Immunodeficiency Virus Type 1 (HIV–1) Infection in Human $CD4^+$ Lymphocyte–Derived Cell Lines Conferred by Using Retroviral Vectors Expressing an HIV–1 RNA–Specific Ribozyme," *Journal of Virology* 65:5531–5534 (1994).

Yamashita et al., "Characterization of Plasma Lipoproteins in Patients Heterozygous for Human Plasma Cholesteryl Ester Transfer Protein (CETP) Deficiency: Plasma CETP Regulates High–Density Lipoprotein Concentration and Composition," *J. Clin. Invest.* 86:688 (1990).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zabner et al., "Adenovirus–Mediated Gene Transfer Transiently Corrects the Chloride Transport Defect in Nasal Epithelia of Patients with Cystic Fibrosis," *Cell* 75:207–216 (1993).

Zhang et al., "Spontaneous Hypercholesterolemia and Arterial Lesions in Mice Lacking Apolipoprotein E," *Science* 258:468 (1992).

Zhou et al., "Synthesis of Functional mRNA in Mammalian Cells by Bacteriophage T3 RNA Polymerase," *Mol. Cell. Biol.* 10:4529–4537 (1990).

Zilversmit et al., "Stimulation of Cholesterol Ester Exchange by Lipo–Protein–Free Rabbit Plasma," *Biochim. Biophys. Acta* 409:393 (1975).

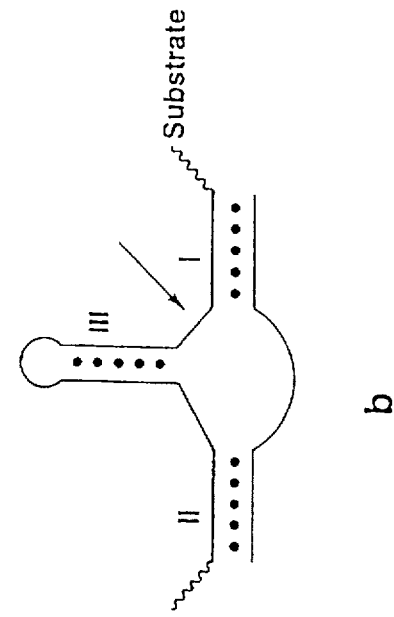
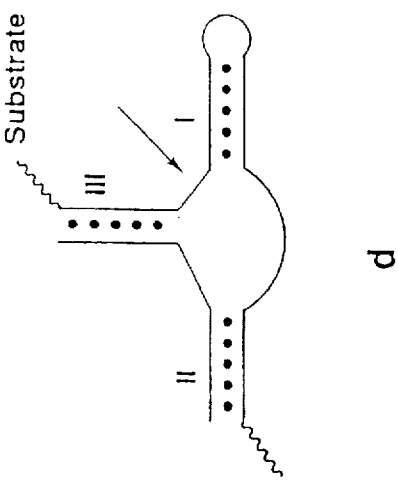
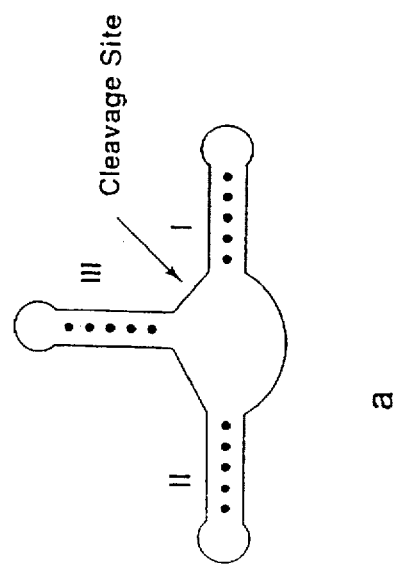
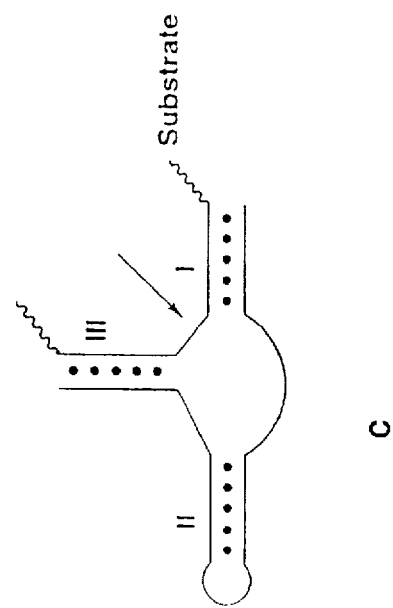

SEQUENCE LISTING ( 1 ) GENERAL INFORMATION:

( i i i ) NUMBER OF SEQUENCES: 1243

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

GGCCGAAAGG CC  12

( 2 ) INFORMATION FOR SEQ ID NO:2:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

UGAAUCUCUG GGGCC  15

( 2 ) INFORMATION FOR SEQ ID NO:3:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

AGAGCCUCAU GUUCC     15

( 2 ) INFORMATION FOR SEQ ID NO:4:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

CUCAUGUUCC GUGGG     15

( 2 ) INFORMATION FOR SEQ ID NO:5:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:5:

UCAUGUUCCG UGGGG     15

( 2 ) INFORMATION FOR SEQ ID NO:6:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:6:

CGGACAUACA UAUAC     15

( 2 ) INFORMATION FOR SEQ ID NO:7:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:7:

CAUACAUAUA CGGGC     15

( 2 ) INFORMATION FOR SEQ ID NO:8:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:8:

UACAUAUACG GGCUC     15

( 2 ) INFORMATION FOR SEQ ID NO:9:

( i ) SEQUENCE CHARACTERISTICS:

( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:9:

ACGGGCUCCA GGCUG     15

( 2 ) INFORMATION FOR SEQ ID NO:10:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:10:

AACGGCUCGG GCCAC     15

( 2 ) INFORMATION FOR SEQ ID NO:11:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:11:

GGCCACUUAC ACACC     15

( 2 ) INFORMATION FOR SEQ ID NO:12:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:12:

GCCACUUACA CACCA     15

( 2 ) INFORMATION FOR SEQ ID NO:13:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:13:

GCCUGAUAAC CAUGC     15

( 2 ) INFORMATION FOR SEQ ID NO:14:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:14:

CCACAGUCCU GACCC     15

( 2 ) INFORMATION FOR SEQ ID NO:15:

( i ) SEQUENCE CHARACTERISTICS:
( A ) LENGTH: 15 base pairs
( B ) TYPE: nucleic acid ( C ) STRANDEDNESS: single
( D ) TOPOLOGY: linear ( x i ) SEQUENCE DESCRIPTION: SEQ ID NO:15:

GCCUGCUCCA AAGGC    15

( 2 ) INFORMATION FOR SEQ ID NO:16:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:16:

GGCACCUCGC ACGAG    15

( 2 ) INFORMATION FOR SEQ ID NO:17:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:17:

CAGGCAUCGU GUGCC    15

( 2 ) INFORMATION FOR SEQ ID NO:18:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:18:

GCCGCAUCAC CAAGC    15

( 2 ) INFORMATION FOR SEQ ID NO:19:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:19:

CUGCCCUCCU GGUGU    15

( 2 ) INFORMATION FOR SEQ ID NO:20:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:20:

CUGGUGUUGA ACCAC    15

( 2 ) INFORMATION FOR SEQ ID NO:21:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:21:

AGGUGAUCCA GACCG 15

( 2 ) INFORMATION FOR SEQ ID NO:22:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

ACCGCCUUCC AGCGA 15

( 2 ) INFORMATION FOR SEQ ID NO:23:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

CCGCCUUCCA GCGAG 15

( 2 ) INFORMATION FOR SEQ ID NO:24:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

GCCAGCUACC CAGAU 15

( 2 ) INFORMATION FOR SEQ ID NO:25:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

CCCAGAUAUC ACGGG 15

( 2 ) INFORMATION FOR SEQ ID NO:26:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

CAGAUAUCAC GGGCG 15

( 2 ) INFORMATION FOR SEQ ID NO:27:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:27:

UGAUGCUCCU UGGCC 15

( 2 ) INFORMATION FOR SEQ ID NO:28:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:28:

UGCUCCUUGG CCAAG 15

( 2 ) INFORMATION FOR SEQ ID NO:29:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:29:

GCCAAGUCAA GUAUG 15

( 2 ) INFORMATION FOR SEQ ID NO:30:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:30:

GUCAAGUAUG GGUUG 15

( 2 ) INFORMATION FOR SEQ ID NO:31:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:31:

UAUGGGUUGC ACAAC 15

( 2 ) INFORMATION FOR SEQ ID NO:32:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:32:

ACAACAUCCA GAUCA 15

( 2 ) INFORMATION FOR SEQ ID NO:33:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:33:

UCCAGAUCAG CCACU 15

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

AGCCACUUGU CCAUC 15

( 2 ) INFORMATION FOR SEQ ID NO:35:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

CACUUGUCCA UCGCC 15

( 2 ) INFORMATION FOR SEQ ID NO:36:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

UGUCCAUCGC CAGCA 15

( 2 ) INFORMATION FOR SEQ ID NO:37:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

GCCAAGUCCA UUGAU 15

( 2 ) INFORMATION FOR SEQ ID NO:38:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

AGUCCAUUGA UGUCU 15

( 2 ) INFORMATION FOR SEQ ID NO:39:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

UUGAUGUCUC CAUUC 15

( 2 ) INFORMATION FOR SEQ ID NO:40:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:40:

GAUGUCUCCA UUCAG 15

( 2 ) INFORMATION FOR SEQ ID NO:41:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:41:

UCUCCAUUCA GAACG 15

( 2 ) INFORMATION FOR SEQ ID NO:42:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:42:

CUCCAUUCAG AACGU 15

( 2 ) INFORMATION FOR SEQ ID NO:43:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:43:

AACGUGUCUG UGGUC 15

( 2 ) INFORMATION FOR SEQ ID NO:44:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:44:

CUGUGGUCUU CAAGG 15

( 2 ) INFORMATION FOR SEQ ID NO:45:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:45:

GUGGUCUUCA AGGGG 15

( 2 ) INFORMATION FOR SEQ ID NO:46:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:46:

UGGUCUUCAA GGGGA 15

( 2 ) INFORMATION FOR SEQ ID NO:47:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:47:

CUGAAGUAUG GCUAC 15

( 2 ) INFORMATION FOR SEQ ID NO:48:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:48:

UAUGGCUACA CCACU 15

( 2 ) INFORMATION FOR SEQ ID NO:49:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:49:

GCUGGGUAUU GAUCA 15

( 2 ) INFORMATION FOR SEQ ID NO:50:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:50:

UGGGUAUUGA UCAGU 15

( 2 ) INFORMATION FOR SEQ ID NO:51:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( x i ) SEQUENCE DESCRIPTION: SEQ ID NO:51:

UAUUGAUCAG UCCAU 15

( 2 ) INFORMATION FOR SEQ ID NO:52:

( i ) SEQUENCE CHARACTERISTICS:
( A ) LENGTH: 15 base pairs ( B ) TYPE: nucleic acid
        ( C ) STRANDEDNESS: single
        ( D ) TOPOLOGY: linear ( x i ) SEQUENCE DESCRIPTION: SEQ ID NO:52:

GAUCAGUCCA UUGAC                                                                                   15

( 2 ) INFORMATION FOR SEQ ID NO:53:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:53:

AGUCCAUUGA CUUCG                                                                                   15

( 2 ) INFORMATION FOR SEQ ID NO:54:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:54:

AUUGACUUCG AGAUC                                                                                   15

( 2 ) INFORMATION FOR SEQ ID NO:55:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:55:

UUGACUUCGA GAUCG                                                                                   15

( 2 ) INFORMATION FOR SEQ ID NO:56:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:56:

UCGAGAUCGA CUCUG                                                                                   15

( 2 ) INFORMATION FOR SEQ ID NO:57:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:57:

AUCGACUCUG CCAUU                                                                                   15

( 2 ) INFORMATION FOR SEQ ID NO:58:

( i ) SEQUENCE CHARACTERISTICS:
        ( A ) LENGTH: 15 base pairs
        ( B ) TYPE: nucleic acid
        ( C ) STRANDEDNESS: single (D) TOPOLOGY: linear (x i) SEQUENCE DESCRIPTION: SEQ ID NO:58:

CUGCCAUUGA CCUCC 15

(2) INFORMATION FOR SEQ ID NO:59:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:59:

UUGACCUCCA GAUCA 15

(2) INFORMATION FOR SEQ ID NO:60:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:60:

UCCAGAUCAA CACAC 15

(2) INFORMATION FOR SEQ ID NO:61:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:61:

UGUGACUCUG GUAGA 15

(2) INFORMATION FOR SEQ ID NO:62:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:62:

CUCUGGUAGA GUGCG 15

(2) INFORMATION FOR SEQ ID NO:63:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:63:

GACUGCUACC UGUCU 15

(2) INFORMATION FOR SEQ ID NO:64:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:64:

UACCUGUCUU UCCAU         15

( 2 ) INFORMATION FOR SEQ ID NO:65:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:65:

CCUGUCUUUC CAUAA         15

( 2 ) INFORMATION FOR SEQ ID NO:66:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:66:

CUGUCUUUCC AUAAG         15

( 2 ) INFORMATION FOR SEQ ID NO:67:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:67:

UGUCUUUCCA UAAGC         15

( 2 ) INFORMATION FOR SEQ ID NO:68:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:68:

UUUCCAUAAG CUGCU         15

( 2 ) INFORMATION FOR SEQ ID NO:69:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:69:

AGCUGCUCCU GCAUC         15

( 2 ) INFORMATION FOR SEQ ID NO:70:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:70:

CCUGCAUCUC CAAGG 15

( 2 ) INFORMATION FOR SEQ ID NO:71:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:71:

UGCAUCUCCA AGGGG 15

( 2 ) INFORMATION FOR SEQ ID NO:72:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:72:

GGUGGAUCAA GCAGC 15

( 2 ) INFORMATION FOR SEQ ID NO:73:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:73:

CAGCUGUUCA CAAAU 15

( 2 ) INFORMATION FOR SEQ ID NO:74:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:74:

AGCUGUUCAC AAAUU 15

( 2 ) INFORMATION FOR SEQ ID NO:75:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:75:

CACAAAUUUC AUCUC 15

( 2 ) INFORMATION FOR SEQ ID NO:76:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:76:

ACAAAUUUCA UCUCC 15

( 2 ) INFORMATION FOR SEQ ID NO:77:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:77:

CAAAUUUCAU CUCCU 15

( 2 ) INFORMATION FOR SEQ ID NO:78:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:78:

AUUUCAUCUC CUUCA 15

( 2 ) INFORMATION FOR SEQ ID NO:79:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:79:

UUCAUCUCCU UCACC 15

( 2 ) INFORMATION FOR SEQ ID NO:80:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:80:

AUCUCCUUCA CCCUG 15

( 2 ) INFORMATION FOR SEQ ID NO:81:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:81:

UCUCCUUCAC CCUGA 15

( 2 ) INFORMATION FOR SEQ ID NO:82:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:82:

AGCUGGUCCU GAAGG 15

( 2 ) INFORMATION FOR SEQ ID NO:83:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:83:

GACAGAUCUG CAAAG                                                                 15

( 2 ) INFORMATION FOR SEQ ID NO:84:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:84:

AAGAGAUCAA CGUCA                                                                 15

( 2 ) INFORMATION FOR SEQ ID NO:85:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:85:

UCAACGUCAU CUCUA                                                                 15

( 2 ) INFORMATION FOR SEQ ID NO:86:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:86:

ACGUCAUCUC UAACA                                                                 15

( 2 ) INFORMATION FOR SEQ ID NO:87:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:87:

GUCAUCUCUA ACAUC                                                                 15

( 2 ) INFORMATION FOR SEQ ID NO:88:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:88:

CAUCUCUAAC AUCAU                                                                 15

( 2 ) INFORMATION FOR SEQ ID NO:89:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:89:

CUAACAUCAU GGCCG                      15

(2) INFORMATION FOR SEQ ID NO:90:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:90:

GGCCGAUUUU GUCCA                      15

(2) INFORMATION FOR SEQ ID NO:91:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:91:

GCCGAUUUUG UCCAG                      15

(2) INFORMATION FOR SEQ ID NO:92:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:92:

CCGAUUUUGU CCAGA                      15

(2) INFORMATION FOR SEQ ID NO:93:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:93:

AUUUUGUCCA GACAA                      15

(2) INFORMATION FOR SEQ ID NO:94:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:94:

CCAGCAUCCU UUCAG                      15

(2) INFORMATION FOR SEQ ID NO:95:

(i) SEQUENCE CHARACTERISTICS:
(A) LENGTH: 15 base pairs
(B) TYPE: nucleic acid (C) STRANDEDNESS: single
(D) TOPOLOGY: linear (xi) SEQUENCE DESCRIPTION: SEQ ID NO:95:

GCAUCCUUUC AGAUG 15

(2) INFORMATION FOR SEQ ID NO:96:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:96:

CAUCCUUUCA GAUGG 15

(2) INFORMATION FOR SEQ ID NO:97:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:97:

AUCCUUUCAG AUGGA 15

(2) INFORMATION FOR SEQ ID NO:98:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:98:

GAGACAUUGG GGUGG 15

(2) INFORMATION FOR SEQ ID NO:99:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:99:

UGGACAUUUC CCUGA 15

(2) INFORMATION FOR SEQ ID NO:100:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:100:

GGACAUUUCC CUGAC 15

(2) INFORMATION FOR SEQ ID NO:101:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO:101:

GACAUUUCCC UGACA 15

( 2 ) INFORMATION FOR SEQ ID NO:102:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:102:

AGGUGAUCCC GUCAU 15

( 2 ) INFORMATION FOR SEQ ID NO:103:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:103:

AUCCCGUCAU CACAG 15

( 2 ) INFORMATION FOR SEQ ID NO:104:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:104:

CCGUCAUCAC AGCCU 15

( 2 ) INFORMATION FOR SEQ ID NO:105:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:105:

ACAGCCUCCU ACCUG 15

( 2 ) INFORMATION FOR SEQ ID NO:106:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:106:

GCCUCCUACC UGGAG 15

( 2 ) INFORMATION FOR SEQ ID NO:107:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:107:

CUGGAGUCCC AUCAC 15

(2) INFORMATION FOR SEQ ID NO:108:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:108:

GUCCCAUCAC AAGGG 15

(2) INFORMATION FOR SEQ ID NO:109:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:109:

CAAGGGUCAU UUCAU 15

(2) INFORMATION FOR SEQ ID NO:110:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:110:

GGGUCAUUUC AUCUA 15

(2) INFORMATION FOR SEQ ID NO:111:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:111:

GGUCAUUUCA UCUAC 15

(2) INFORMATION FOR SEQ ID NO:112:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:112:

GUCAUUUCAU CUACA 15

(2) INFORMATION FOR SEQ ID NO:113:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:113:

AUUUCAUCUA CAAGA 15

( 2 ) INFORMATION FOR SEQ ID NO:114:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:114:

UUCAUCUACA AGAAU 15

( 2 ) INFORMATION FOR SEQ ID NO:115:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:115:

AGAAUGUCUC AGAGG 15

( 2 ) INFORMATION FOR SEQ ID NO:116:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:116:

AAUGUCUCAG AGGAC 15

( 2 ) INFORMATION FOR SEQ ID NO:117:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:117:

AGGACCUCCC CCUCC 15

( 2 ) INFORMATION FOR SEQ ID NO:118:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:118:

UCCCCCUCCC CACCU 15

( 2 ) INFORMATION FOR SEQ ID NO:119:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:119:

CCCACCUUCU CGCCC 15

( 2 ) INFORMATION FOR SEQ ID NO:120:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:120:

CCACCUUCUC GCCCA　　　　　　　　　　　　　　　　　15

( 2 ) INFORMATION FOR SEQ ID NO:121:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:121:

ACCUUCUCGC CCACA　　　　　　　　　　　　　　　　　15

( 2 ) INFORMATION FOR SEQ ID NO:122:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:122:

GGGGACUCCC GCAUG　　　　　　　　　　　　　　　　　15

( 2 ) INFORMATION FOR SEQ ID NO:123:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:123:

AUGCUGUACU UCUGG　　　　　　　　　　　　　　　　　15

( 2 ) INFORMATION FOR SEQ ID NO:124:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:124:

CUGUACUUCU GGUUC　　　　　　　　　　　　　　　　　15

( 2 ) INFORMATION FOR SEQ ID NO:125:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:125:

UGUACUUCUG GUUCU　　　　　　　　　　　　　　　　　15

( 2 ) INFORMATION FOR SEQ ID NO:126:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:126:

UUCUGGUUCU CUGAG 15

( 2 ) INFORMATION FOR SEQ ID NO:127:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:127:

UCUGGUUCUC UGAGC 15

( 2 ) INFORMATION FOR SEQ ID NO:128:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:128:

UGGUUCUCUG AGCGA 15

( 2 ) INFORMATION FOR SEQ ID NO:129:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:129:

AGCGAGUCUU CCACU 15

( 2 ) INFORMATION FOR SEQ ID NO:130:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:130:

CGAGUCUUCC ACUCG 15

( 2 ) INFORMATION FOR SEQ ID NO:131:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:131:

GAGUCUUCCA CUCGC 15

( 2 ) INFORMATION FOR SEQ ID NO:132:

( i ) SEQUENCE CHARACTERISTICS:
    ( A ) LENGTH: 15 base pairs

```
            ( B ) TYPE: nucleic acid
            ( C ) STRANDEDNESS: single
            ( D ) TOPOLOGY: linear ( x i ) SEQUENCE DESCRIPTION: SEQ ID NO:132:

UUCCACUCGC UGGCC                                                                        15

( 2 ) INFORMATION FOR SEQ ID NO:133:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:133:

CCAAGGUAGC UUUCC                                                                        15

( 2 ) INFORMATION FOR SEQ ID NO:134:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:134:

GGUAGCUUUC CAGGA                                                                        15

( 2 ) INFORMATION FOR SEQ ID NO:135:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:135:

GUAGCUUUCC AGGAU                                                                        15

( 2 ) INFORMATION FOR SEQ ID NO:136:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:136:

UAGCUUUCCA GGAUG                                                                        15

( 2 ) INFORMATION FOR SEQ ID NO:137:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:137:

GCCGCCUCAU GCUCA                                                                        15

( 2 ) INFORMATION FOR SEQ ID NO:138:

( i ) SEQUENCE CHARACTERISTICS:
            ( A ) LENGTH: 15 base pairs
            ( B ) TYPE: nucleic acid
            ( C ) STRANDEDNESS: single
```

(D) TOPOLOGY: linear (xi) SEQUENCE DESCRIPTION: SEQ ID NO:138:

UCAUGCUCAG CCUGA 15

(2) INFORMATION FOR SEQ ID NO:139:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:139:

GACGAGUUCA AGGCA 15

(2) INFORMATION FOR SEQ ID NO:140:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:140:

ACGAGUUCAA GGCAG 15

(2) INFORMATION FOR SEQ ID NO:141:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:141:

UGGGGCUUCA ACACC 15

(2) INFORMATION FOR SEQ ID NO:142:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:142:

GGGGCUUCAA CACCA 15

(2) INFORMATION FOR SEQ ID NO:143:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:143:

AGGAAAUCUU CCAAG 15

(2) INFORMATION FOR SEQ ID NO:144:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:144:

GAAAUCUUCC AAGAG                                                                 15

(2) INFORMATION FOR SEQ ID NO:145:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:145:

AAAUCUUCCA AGAGG                                                                 15

(2) INFORMATION FOR SEQ ID NO:146:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:146:

AAGAGGUUGU CGGCG                                                                 15

(2) INFORMATION FOR SEQ ID NO:147:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:147:

AGGUUGUCGG CGGCU                                                                 15

(2) INFORMATION FOR SEQ ID NO:148:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:148:

GGCGGCUUCC CCAGC                                                                 15

(2) INFORMATION FOR SEQ ID NO:149:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:149:

GCGGCUUCCC CAGCC                                                                 15

(2) INFORMATION FOR SEQ ID NO:150:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:150:

CCCAAGUCAC CGUCC　15

( 2 ) INFORMATION FOR SEQ ID NO:151:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:151:

UCACCGUCCA CUGCC　15

( 2 ) INFORMATION FOR SEQ ID NO:152:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:152:

ACUGCCUCAA GAUGC　15

( 2 ) INFORMATION FOR SEQ ID NO:153:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:153:

CCAAGAUCUC CUGCC　15

( 2 ) INFORMATION FOR SEQ ID NO:154:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:154:

AAGAUCUCCU GCCAA　15

( 2 ) INFORMATION FOR SEQ ID NO:155:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:155:

AGGGAGUCGU GGUCA　15

( 2 ) INFORMATION FOR SEQ ID NO:156:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:156:

UCGUGGUCAA UUCUU　15

( 2 ) INFORMATION FOR SEQ ID NO:157:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:157:

GGUCAAUUCU UCAGU     15

( 2 ) INFORMATION FOR SEQ ID NO:158:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:158:

GUCAAUUCUU CAGUG     15

( 2 ) INFORMATION FOR SEQ ID NO:159:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:159:

CAAUUCUUCA GUGAU     15

( 2 ) INFORMATION FOR SEQ ID NO:160:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:160:

AAUUCUUCAG UGAUG     15

( 2 ) INFORMATION FOR SEQ ID NO:161:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:161:

GUGAAAUUCC UCUUU     15

( 2 ) INFORMATION FOR SEQ ID NO:162:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:162:

UGAAAUUCCU CUUUC     15

( 2 ) INFORMATION FOR SEQ ID NO:163:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:163:

AAUUCCUCUU UCCAC      15

( 2 ) INFORMATION FOR SEQ ID NO:164:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:164:

UUCCUCUUUC CACGC      15

( 2 ) INFORMATION FOR SEQ ID NO:165:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:165:

UCCUCUUUCC ACGCC      15

( 2 ) INFORMATION FOR SEQ ID NO:166:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:166:

CCUCUUUCCA CGCCC      15

( 2 ) INFORMATION FOR SEQ ID NO:167:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:167:

GCAACAUUCU GUAGC      15

( 2 ) INFORMATION FOR SEQ ID NO:168:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:168:

CAACAUUCUG UAGCU      15

( 2 ) INFORMATION FOR SEQ ID NO:169:

( i ) SEQUENCE CHARACTERISTICS:

(A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:169:

AUUCUGUAGC UUACA                                                                             15

( 2 ) INFORMATION FOR SEQ ID NO:170:

( i ) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:170:

UGUAGCUUAC ACAUU                                                                             15

( 2 ) INFORMATION FOR SEQ ID NO:171:

( i ) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:171:

GUAGCUUACA CAUUU                                                                             15

( 2 ) INFORMATION FOR SEQ ID NO:172:

( i ) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:172:

UACACAUUUG AAGAG                                                                             15

( 2 ) INFORMATION FOR SEQ ID NO:173:

( i ) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:173:

ACACAUUUGA AGAGG                                                                             15

( 2 ) INFORMATION FOR SEQ ID NO:174:

( i ) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:174:

AGAGGAUAUC GUGAC                                                                             15

( 2 ) INFORMATION FOR SEQ ID NO:175:

( i ) SEQUENCE CHARACTERISTICS:
        (A) LENGTH: 15 base pairs
        (B) TYPE: nucleic acid 5,705,388

-continued ( C ) STRANDEDNESS: single
                    ( D ) TOPOLOGY: linear ( x i ) SEQUENCE DESCRIPTION: SEQ ID NO:175:

AGGAUAUCGU GACUA                                                          15

( 2 ) INFORMATION FOR SEQ ID NO:176:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:176:

CGUGACUACC GUCCA                                                          15

( 2 ) INFORMATION FOR SEQ ID NO:177:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:177:

CUACCGUCCA GGCCU                                                          15

( 2 ) INFORMATION FOR SEQ ID NO:178:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:178:

CAGGCCUCCU AUUCU                                                          15

( 2 ) INFORMATION FOR SEQ ID NO:179:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:179:

GCCUCCUAUU CUAAG                                                          15

( 2 ) INFORMATION FOR SEQ ID NO:180:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:180:

CUCCUAUUCU AAGAA                                                          15

( 2 ) INFORMATION FOR SEQ ID NO:181:

( i ) SEQUENCE CHARACTERISTICS:
                    ( A ) LENGTH: 15 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:181:

UCCUAUUCUA AGAAA                                                                 15

( 2 ) INFORMATION FOR SEQ ID NO:182:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:182:

CUAUUCUAAG AAAAA                                                                 15

( 2 ) INFORMATION FOR SEQ ID NO:183:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:183:

AAAAGCUCUU CUUAA                                                                 15

( 2 ) INFORMATION FOR SEQ ID NO:184:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:184:

AAGCUCUUCU UAAGC                                                                 15

( 2 ) INFORMATION FOR SEQ ID NO:185:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:185:

AGCUCUUCUU AAGCC                                                                 15

( 2 ) INFORMATION FOR SEQ ID NO:186:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:186:

CUCUUCUUAA GCCUC                                                                 15

( 2 ) INFORMATION FOR SEQ ID NO:187:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:187:

```
UCUUCUUAAG CCUCU                                                                    15
```

(2) INFORMATION FOR SEQ ID NO:188:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:188:

```
UAAGCCUCUU GGAUU                                                                    15
```

(2) INFORMATION FOR SEQ ID NO:189:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:189:

```
AGCCUCUUGG AUUUC                                                                    15
```

(2) INFORMATION FOR SEQ ID NO:190:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:190:

```
CUUGGAUUUC CAGAU                                                                    15
```

(2) INFORMATION FOR SEQ ID NO:191:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:191:

```
UUGGAUUUCC AGAUU                                                                    15
```

(2) INFORMATION FOR SEQ ID NO:192:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:192:

```
UGGAUUUCCA GAUUA                                                                    15
```

(2) INFORMATION FOR SEQ ID NO:193:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:193:

```
UCCAGAUUAC ACCAA                                                                    15
```

( 2 ) INFORMATION FOR SEQ ID NO:194:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:194:

CCAGAUUACA CCAAA                                  15

( 2 ) INFORMATION FOR SEQ ID NO:195:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:195:

AGACUGUUUC CAACU                                  15

( 2 ) INFORMATION FOR SEQ ID NO:196:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:196:

GACUGUUUCC AACUU                                  15

( 2 ) INFORMATION FOR SEQ ID NO:197:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:197:

ACUGUUUCCA ACUUG                                  15

( 2 ) INFORMATION FOR SEQ ID NO:198:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:198:

UCCAACUUGA CUGAG                                  15

( 2 ) INFORMATION FOR SEQ ID NO:199:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:199:

AGCAGCUCCG AGUCC                                  15

( 2 ) INFORMATION FOR SEQ ID NO:200:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:200:

UCCGAGUCCA UCCAG     15

( 2 ) INFORMATION FOR SEQ ID NO:201:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:201:

AGUCCAUCCA GAGCU     15

( 2 ) INFORMATION FOR SEQ ID NO:202:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:202:

CAGAGCUUCC UGCAG     15

( 2 ) INFORMATION FOR SEQ ID NO:203:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:203:

AGAGCUUCCU GCAGU     15

( 2 ) INFORMATION FOR SEQ ID NO:204:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:204:

CUGCAGUCAA UGAUC     15

( 2 ) INFORMATION FOR SEQ ID NO:205:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:205:

CAAUGAUCAC CGCUG     15

( 2 ) INFORMATION FOR SEQ ID NO:206:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:206:

UGGGCAUCCC UGAGG      15

( 2 ) INFORMATION FOR SEQ ID NO:207:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:207:

CUGAGGUCAU GUCUC      15

( 2 ) INFORMATION FOR SEQ ID NO:208:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:208:

GUCAUGUCUC GGCUC      15

( 2 ) INFORMATION FOR SEQ ID NO:209:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:209:

CAUGUCUCGG CUCGA      15

( 2 ) INFORMATION FOR SEQ ID NO:210:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:210:

CUCGGCUCGA GGUAG      15

( 2 ) INFORMATION FOR SEQ ID NO:211:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:211:

UCGAGGUAGU GUUUA      15

( 2 ) INFORMATION FOR SEQ ID NO:212:

( i ) SEQUENCE CHARACTERISTICS:
    ( A ) LENGTH: 15 base pairs 5,705,388

113

114

-continued ( B ) TYPE: nucleic acid
        ( C ) STRANDEDNESS: single
        ( D ) TOPOLOGY: linear ( x i ) SEQUENCE DESCRIPTION: SEQ ID NO:212:

GUAGUGUUUA CAGCC                                                                15

( 2 ) INFORMATION FOR SEQ ID NO:213:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:213:

UAGUGUUUAC AGCCC                                                                15

( 2 ) INFORMATION FOR SEQ ID NO:214:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:214:

AGUGUUUACA GCCCU                                                                15

( 2 ) INFORMATION FOR SEQ ID NO:215:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:215:

CAGCCCUCAU GAACA                                                                15

( 2 ) INFORMATION FOR SEQ ID NO:216:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:216:

UGAGCCUCUU CGACA                                                                15

( 2 ) INFORMATION FOR SEQ ID NO:217:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:217:

AGCCUCUUCG ACAUC                                                                15

( 2 ) INFORMATION FOR SEQ ID NO:218:

( i ) SEQUENCE CHARACTERISTICS:
        ( A ) LENGTH: 15 base pairs
        ( B ) TYPE: nucleic acid
        ( C ) STRANDEDNESS: single (D) TOPOLOGY: linear (x i) SEQUENCE DESCRIPTION: SEQ ID NO:218:

GCCUCUUCGA CAUCA  15

(2) INFORMATION FOR SEQ ID NO:219:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:219:

UCGACAUCAU CAACC  15

(2) INFORMATION FOR SEQ ID NO:220:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:220:

ACAUCAUCAA CCCUG  15

(2) INFORMATION FOR SEQ ID NO:221:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:221:

CUGAGAUUAU CACUC  15

(2) INFORMATION FOR SEQ ID NO:222:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:222:

UGAGAUUAUC ACUCG  15

(2) INFORMATION FOR SEQ ID NO:223:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:223:

AGAUUAUCAC UCGAG  15

(2) INFORMATION FOR SEQ ID NO:224:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:224:

UAUCACUCGA GAUGG    15

( 2 ) INFORMATION FOR SEQ ID NO:225:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:225:

GAUGGCUUCC UGCUG    15

( 2 ) INFORMATION FOR SEQ ID NO:226:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:226:

AUGGCUUCCU GCUGC    15

( 2 ) INFORMATION FOR SEQ ID NO:227:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:227:

AUGGACUUUG GCUUC    15

( 2 ) INFORMATION FOR SEQ ID NO:228:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:228:

UGGACUUUGG CUUCC    15

( 2 ) INFORMATION FOR SEQ ID NO:229:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:229:

UUUGGCUUCC CUGAG    15

( 2 ) INFORMATION FOR SEQ ID NO:230:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:230:

UUGGCUUCCC UGAGC                                                    15

( 2 ) INFORMATION FOR SEQ ID NO:231:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:231:

GGUGGAUUUC CUCCA                                                    15

( 2 ) INFORMATION FOR SEQ ID NO:232:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:232:

GUGGAUUUCC UCCAG                                                    15

( 2 ) INFORMATION FOR SEQ ID NO:233:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:233:

UGGAUUUCCU CCAGA                                                    15

( 2 ) INFORMATION FOR SEQ ID NO:234:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:234:

AUUUCCUCCA GAGCU                                                    15

( 2 ) INFORMATION FOR SEQ ID NO:235:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:235:

CAGAGCUUGA GCUAG                                                    15

( 2 ) INFORMATION FOR SEQ ID NO:236:

( i ) SEQUENCE CHARACTERISTICS:
     ( A ) LENGTH: 15 base pairs
     ( B ) TYPE: nucleic acid
     ( C ) STRANDEDNESS: single
     ( D ) TOPOLOGY: linear ( x i ) SEQUENCE DESCRIPTION: SEQ ID NO:236:

UUGAGCUAGA AGUCU                                                    15

( 2 ) INFORMATION FOR SEQ ID NO:237:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:237:

UAGAAGUCUC CAAGG 15

( 2 ) INFORMATION FOR SEQ ID NO:238:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:238:

GAAGUCUCCA AGGAG 15

( 2 ) INFORMATION FOR SEQ ID NO:239:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:239:

AGGAGGUCGG GAUGG 15

( 2 ) INFORMATION FOR SEQ ID NO:240:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:240:

UGGGGCUUGU AGCAG 15

( 2 ) INFORMATION FOR SEQ ID NO:241:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:241:

GGCUUGUAGC AGAAG 15

( 2 ) INFORMATION FOR SEQ ID NO:242:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:242:

CCAGGCUCAC AGCUG 15

( 2 ) INFORMATION FOR SEQ ID NO:243:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:243:

CUGGUGUCUC CUCCA    15

( 2 ) INFORMATION FOR SEQ ID NO:244:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:244:

GGUGUCUCCU CCAGC    15

( 2 ) INFORMATION FOR SEQ ID NO:245:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:245:

GUCUCCUCCA GCGUG    15

( 2 ) INFORMATION FOR SEQ ID NO:246:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:246:

UGGAAGUUGG GUUAG    15

( 2 ) INFORMATION FOR SEQ ID NO:247:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:247:

GUUGGGUUAG GAGUA    15

( 2 ) INFORMATION FOR SEQ ID NO:248:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:248:

UUGGGUUAGG AGUAC    15

( 2 ) INFORMATION FOR SEQ ID NO:249:

( i ) SEQUENCE CHARACTERISTICS:

(A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:249:

UAGGAGUACG GAGAU							15

(2) INFORMATION FOR SEQ ID NO:250:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:250:

UGGAGAUUGG CUCCC							15

(2) INFORMATION FOR SEQ ID NO:251:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:251:

AUUGGCUCCC AACUC							15

(2) INFORMATION FOR SEQ ID NO:252:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:252:

CCCAACUCCU CCCUA							15

(2) INFORMATION FOR SEQ ID NO:253:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:253:

AACUCCUCCC UAUCC							15

(2) INFORMATION FOR SEQ ID NO:254:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:254:

CCUCCCUAUC CUAAA							15

(2) INFORMATION FOR SEQ ID NO:255:

(i) SEQUENCE CHARACTERISTICS:
            (A) LENGTH: 15 base pairs
            (B) TYPE: nucleic acid ( C ) STRANDEDNESS: single
            ( D ) TOPOLOGY: linear ( x i ) SEQUENCE DESCRIPTION: SEQ ID NO:255:

UCCCUAUCCU AAAGG                                                                                           15

( 2 ) INFORMATION FOR SEQ ID NO:256:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:256:

CUAUCCUAAA GGCCC                                                                                           15

( 2 ) INFORMATION FOR SEQ ID NO:257:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:257:

CUGGCAUUAA AGUGC                                                                                           15

( 2 ) INFORMATION FOR SEQ ID NO:258:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:258:

UGGCAUUAAA GUGCU                                                                                           15

( 2 ) INFORMATION FOR SEQ ID NO:259:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:259:

GGCCCCACUG AUGAGGCCGA AAGGCCGAAA GAUUCA                                                                    36

( 2 ) INFORMATION FOR SEQ ID NO:260:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:260:

GGAACAUCUG AUGAGGCCGA AAGGCCGAAA GGCUCU                                                                    36

( 2 ) INFORMATION FOR SEQ ID NO:261:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:261:

CCCACGGCUG AUGAGGCCGA AAGGCCGAAA CAUGAG 36

( 2 ) INFORMATION FOR SEQ ID NO:262:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:262:

CCCCACGCUG AUGAGGCCGA AAGGCCGAAA ACAUGA 36

( 2 ) INFORMATION FOR SEQ ID NO:263:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:263:

GUAUAUGCUG AUGAGGCCGA AAGGCCGAAA UGUCCG 36

( 2 ) INFORMATION FOR SEQ ID NO:264:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:264:

GCCCGUACUG AUGAGGCCGA AAGGCCGAAA UGUAUG 36

( 2 ) INFORMATION FOR SEQ ID NO:265:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:265:

GAGCCCGCUG AUGAGGCCGA AAGGCCGAAA UAUGUA 36

( 2 ) INFORMATION FOR SEQ ID NO:266:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:266:

CAGCCUGCUG AUGAGGCCGA AAGGCCGAAA GCCCGU 36

( 2 ) INFORMATION FOR SEQ ID NO:267:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:267:

GUGGCCCCUG AUGAGGCCGA AAGGCCGAAA GCCGUU    36

( 2 ) INFORMATION FOR SEQ ID NO:268:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:268:

GGUGUGUCUG AUGAGGCCGA AAGGCCGAAA GUGGCC    36

( 2 ) INFORMATION FOR SEQ ID NO:269:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:269:

UGGUGUGCUG AUGAGGCCGA AAGGCCGAAA AGUGGC    36

( 2 ) INFORMATION FOR SEQ ID NO:270:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:270:

GCAUGGUCUG AUGAGGCCGA AAGGCCGAAA UCAGGC    36

( 2 ) INFORMATION FOR SEQ ID NO:271:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:271:

GGGUCAGCUG AUGAGGCCGA AAGGCCGAAA CUGUGG    36

( 2 ) INFORMATION FOR SEQ ID NO:272:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:272:

GCCUUUGCUG AUGAGGCCGA AAGGCCGAAA GCAGGC    36

( 2 ) INFORMATION FOR SEQ ID NO:273:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:273:

CUCGUGCCUG AUGAGGCCGA AAGGCCGAAA GGUGCC    36

( 2 ) INFORMATION FOR SEQ ID NO:274:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:274:

GGCACACCUG AUGAGGCCGA AAGGCCGAAA UGCCUG    36

( 2 ) INFORMATION FOR SEQ ID NO:275:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:275:

GCUUGGUCUG AUGAGGCCGA AAGGCCGAAA UGCGGC    36

( 2 ) INFORMATION FOR SEQ ID NO:276:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:276:

ACACCAGCUG AUGAGGCCGA AAGGCCGAAA GGGCAG    36

( 2 ) INFORMATION FOR SEQ ID NO:277:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:277:

GUGGUUCCUG AUGAGGCCGA AAGGCCGAAA CACCAG    36

( 2 ) INFORMATION FOR SEQ ID NO:278:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:278:

CGGUCUGCUG AUGAGGCCGA AAGGCCGAAA UCACCU    36

( 2 ) INFORMATION FOR SEQ ID NO:279:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:279:

UCGCUGGCUG AUGAGGCCGA AAGGCCGAAA GGCGGU    36

( 2 ) INFORMATION FOR SEQ ID NO:280:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:280:

CUCGCUGCUG AUGAGGCCGA AAGGCCGAAA AGGCGG  36

( 2 ) INFORMATION FOR SEQ ID NO:281:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:281:

AUCUGGGCUG AUGAGGCCGA AAGGCCGAAA GCUGGC  36

( 2 ) INFORMATION FOR SEQ ID NO:282:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:282:

CCCGUGACUG AUGAGGCCGA AAGGCCGAAA UCUGGG  36

( 2 ) INFORMATION FOR SEQ ID NO:283:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:283:

CGCCCGUCUG AUGAGGCCGA AAGGCCGAAA UAUCUG  36

( 2 ) INFORMATION FOR SEQ ID NO:284:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:284:

GGCCAAGCUG AUGAGGCCGA AAGGCCGAAA GCAUCA  36

( 2 ) INFORMATION FOR SEQ ID NO:285:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:285:

CUUGGCCCUG AUGAGGCCGA AAGGCCGAAA GGAGCA  36

( 2 ) INFORMATION FOR SEQ ID NO:286:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:286:

CAUACUUCUG AUGAGGCCGA AAGGCCGAAA CUUGGC    36

( 2 ) INFORMATION FOR SEQ ID NO:287:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:287:

CAACCCACUG AUGAGGCCGA AAGGCCGAAA CUUGAC    36

( 2 ) INFORMATION FOR SEQ ID NO:288:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:288:

GUUGUGCCUG AUGAGGCCGA AAGGCCGAAA CCCAUA    36

( 2 ) INFORMATION FOR SEQ ID NO:289:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:289:

UGAUCUGCUG AUGAGGCCGA AAGGCCGAAA UGUUGU    36

( 2 ) INFORMATION FOR SEQ ID NO:290:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:290:

AGUGGCUCUG AUGAGGCCGA AAGGCCGAAA UCUGGA    36

( 2 ) INFORMATION FOR SEQ ID NO:291:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:291:

GAUGGACCUG AUGAGGCCGA AAGGCCGAAA GUGGCU    36

( 2 ) INFORMATION FOR SEQ ID NO:292:

( i ) SEQUENCE CHARACTERISTICS:
  ( A ) LENGTH: 36 base pairs ( B ) TYPE: nucleic acid
            ( C ) STRANDEDNESS: single
            ( D ) TOPOLOGY: linear ( x i ) SEQUENCE DESCRIPTION: SEQ ID NO:292:

GGCGAUGCUG AUGAGGCCGA AAGGCCGAAA CAAGUG        36

( 2 ) INFORMATION FOR SEQ ID NO:293:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:293:

UGCUGGCCUG AUGAGGCCGA AAGGCCGAAA UGGACA        36

( 2 ) INFORMATION FOR SEQ ID NO:294:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:294:

AUCAAUGCUG AUGAGGCCGA AAGGCCGAAA CUUGGC        36

( 2 ) INFORMATION FOR SEQ ID NO:295:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:295:

AGACAUCCUG AUGAGGCCGA AAGGCCGAAA UGGACU        36

( 2 ) INFORMATION FOR SEQ ID NO:296:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:296:

GAAUGGACUG AUGAGGCCGA AAGGCCGAAA CAUCAA        36

( 2 ) INFORMATION FOR SEQ ID NO:297:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:297:

CUGAAUGCUG AUGAGGCCGA AAGGCCGAAA GACAUC        36

( 2 ) INFORMATION FOR SEQ ID NO:298:

( i ) SEQUENCE CHARACTERISTICS:
            ( A ) LENGTH: 36 base pairs
            ( B ) TYPE: nucleic acid
            ( C ) STRANDEDNESS: single (D) TOPOLOGY: linear (xi) SEQUENCE DESCRIPTION: SEQ ID NO:298:

CGUUCUGCUG AUGAGGCCGA AAGGCCGAAA UGGAGA    36

(2) INFORMATION FOR SEQ ID NO:299:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:299:

ACGUUCUCUG AUGAGGCCGA AAGGCCGAAA AUGGAG    36

(2) INFORMATION FOR SEQ ID NO:300:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:300:

GACCACACUG AUGAGGCCGA AAGGCCGAAA CACGUU    36

(2) INFORMATION FOR SEQ ID NO:301:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:301:

CCUUGAACUG AUGAGGCCGA AAGGCCGAAA CCACAG    36

(2) INFORMATION FOR SEQ ID NO:302:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:302:

CCCCUUGCUG AUGAGGCCGA AAGGCCGAAA GACCAC    36

(2) INFORMATION FOR SEQ ID NO:303:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:303:

UCCCCUUCUG AUGAGGCCGA AAGGCCGAAA AGACCA    36

(2) INFORMATION FOR SEQ ID NO:304:

(i) SEQUENCE CHARACTERISTICS:
    (A) LENGTH: 36 base pairs
    (B) TYPE: nucleic acid
    (C) STRANDEDNESS: single
    (D) TOPOLOGY: linear ( x i ) SEQUENCE DESCRIPTION: SEQ ID NO:304:

GUAGCCACUG AUGAGGCCGA AAGGCCGAAA CUUCAG    36

( 2 ) INFORMATION FOR SEQ ID NO:305:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:305:

AGUGGUGCUG AUGAGGCCGA AAGGCCGAAA GCCAUA    36

( 2 ) INFORMATION FOR SEQ ID NO:306:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:306:

UGAUCAACUG AUGAGGCCGA AAGGCCGAAA CCCAGC    36

( 2 ) INFORMATION FOR SEQ ID NO:307:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:307:

ACUGAUCCUG AUGAGGCCGA AAGGCCGAAA UACCCA    36

( 2 ) INFORMATION FOR SEQ ID NO:308:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:308:

AUGGACUCUG AUGAGGCCGA AAGGCCGAAA UCAAUA    36

( 2 ) INFORMATION FOR SEQ ID NO:309:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:309:

GUCAAUGCUG AUGAGGCCGA AAGGCCGAAA CUGAUC    36

( 2 ) INFORMATION FOR SEQ ID NO:310:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:310:

CGAAGUCCUG AUGAGGCCGA AAGGCCGAAA UGGACU 36

( 2 ) INFORMATION FOR SEQ ID NO:311:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:311:

GAUCUCGCUG AUGAGGCCGA AAGGCCGAAA GUCAAU 36

( 2 ) INFORMATION FOR SEQ ID NO:312:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:312:

CGAUCUCCUG AUGAGGCCGA AAGGCCGAAA AGUCAA 36

( 2 ) INFORMATION FOR SEQ ID NO:313:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:313:

CAGAGUCCUG AUGAGGCCGA AAGGCCGAAA UCUCGA 36

( 2 ) INFORMATION FOR SEQ ID NO:314:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:314:

AAUGGCACUG AUGAGGCCGA AAGGCCGAAA GUCGAU 36

( 2 ) INFORMATION FOR SEQ ID NO:315:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:315:

GGAGGUCCUG AUGAGGCCGA AAGGCCGAAA UGGCAG 36

( 2 ) INFORMATION FOR SEQ ID NO:316:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:316:

UGAUCUGCUG AUGAGGCCGA AAGGCCGAAA GGUCAA 36

( 2 ) INFORMATION FOR SEQ ID NO:317:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:317:

GUGUGUUCUG AUGAGGCCGA AAGGCCGAAA UCUGGA  36

( 2 ) INFORMATION FOR SEQ ID NO:318:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:318:

UCUACCACUG AUGAGGCCGA AAGGCCGAAA GUCACA  36

( 2 ) INFORMATION FOR SEQ ID NO:319:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:319:

CGCACUCCUG AUGAGGCCGA AAGGCCGAAA CCAGAG  36

( 2 ) INFORMATION FOR SEQ ID NO:320:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:320:

AGACAGGCUG AUGAGGCCGA AAGGCCGAAA GCAGUC  36

( 2 ) INFORMATION FOR SEQ ID NO:321:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:321:

AUGGAAACUG AUGAGGCCGA AAGGCCGAAA CAGGUA  36

( 2 ) INFORMATION FOR SEQ ID NO:322:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:322:

UUAUGGACUG AUGAGGCCGA AAGGCCGAAA GACAGG  36

( 2 ) INFORMATION FOR SEQ ID NO:323:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:323:

CUUAUGGCUG AUGAGGCCGA AAGGCCGAAA AGACAG 36

( 2 ) INFORMATION FOR SEQ ID NO:324:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:324:

GCUUAUGCUG AUGAGGCCGA AAGGCCGAAA AAGACA 36

( 2 ) INFORMATION FOR SEQ ID NO:325:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:325:

AGCAGCUCUG AUGAGGCCGA AAGGCCGAAA UGGAAA 36

( 2 ) INFORMATION FOR SEQ ID NO:326:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:326:

GAUGCAGCUG AUGAGGCCGA AAGGCCGAAA GCAGCU 36

( 2 ) INFORMATION FOR SEQ ID NO:327:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:327:

CCUUGGACUG AUGAGGCCGA AAGGCCGAAA UGCAGG 36

( 2 ) INFORMATION FOR SEQ ID NO:328:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:328:

CCCCUUGCUG AUGAGGCCGA AAGGCCGAAA GAUGCA 36

( 2 ) INFORMATION FOR SEQ ID NO:329:

( i ) SEQUENCE CHARACTERISTICS:

( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:329:

GCUGCUUCUG AUGAGGCCGA AAGGCCGAAA UCCACC    36

( 2 ) INFORMATION FOR SEQ ID NO:330:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:330:

AUUUGUGCUG AUGAGGCCGA AAGGCCGAAA CAGCUG    36

( 2 ) INFORMATION FOR SEQ ID NO:331:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:331:

AAUUUGUCUG AUGAGGCCGA AAGGCCGAAA ACAGCU    36

( 2 ) INFORMATION FOR SEQ ID NO:332:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:332:

GAGAUGACUG AUGAGGCCGA AAGGCCGAAA UUUGUG    36

( 2 ) INFORMATION FOR SEQ ID NO:333:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:333:

GGAGAUGCUG AUGAGGCCGA AAGGCCGAAA AUUUGU    36

( 2 ) INFORMATION FOR SEQ ID NO:334:

( i ) SEQUENCE CHARACTERISTICS:
            ( A ) LENGTH: 36 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:334:

AGGAGAUCUG AUGAGGCCGA AAGGCCGAAA AAUUUG    36

( 2 ) INFORMATION FOR SEQ ID NO:335:

( i ) SEQUENCE CHARACTERISTICS:
            ( A ) LENGTH: 36 base pairs
            ( B ) TYPE: nucleic acid ( C ) STRANDEDNESS: single
( D ) TOPOLOGY: linear ( x i ) SEQUENCE DESCRIPTION: SEQ ID NO:335:

UGAAGGACUG AUGAGGCCGA AAGGCCGAAA UGAAAU    36

( 2 ) INFORMATION FOR SEQ ID NO:336:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:336:

GGUGAAGCUG AUGAGGCCGA AAGGCCGAAA GAUGAA    36

( 2 ) INFORMATION FOR SEQ ID NO:337:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:337:

CAGGGUGCUG AUGAGGCCGA AAGGCCGAAA GGAGAU    36

( 2 ) INFORMATION FOR SEQ ID NO:338:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:338:

UCAGGGUCUG AUGAGGCCGA AAGGCCGAAA AGGAGA    36

( 2 ) INFORMATION FOR SEQ ID NO:339:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:339:

CCUUCAGCUG AUGAGGCCGA AAGGCCGAAA CCAGCU    36

( 2 ) INFORMATION FOR SEQ ID NO:340:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:340:

CUUUGCACUG AUGAGGCCGA AAGGCCGAAA UCUGUC    36

( 2 ) INFORMATION FOR SEQ ID NO:341:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:341:

UGACGUUCUG AUGAGGCCGA AAGGCCGAAA UCUCUU    36

( 2 ) INFORMATION FOR SEQ ID NO:342:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:342:

UAGAGAUCUG AUGAGGCCGA AAGGCCGAAA CGUUGA    36

( 2 ) INFORMATION FOR SEQ ID NO:343:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:343:

UGUUAGACUG AUGAGGCCGA AAGGCCGAAA UGACGU    36

( 2 ) INFORMATION FOR SEQ ID NO:344:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:344:

GAUGUUACUG AUGAGGCCGA AAGGCCGAAA GAUGAC    36

( 2 ) INFORMATION FOR SEQ ID NO:345:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:345:

AUGAUGUCUG AUGAGGCCGA AAGGCCGAAA GAGAUG    36

( 2 ) INFORMATION FOR SEQ ID NO:346:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:346:

CGGCCAUCUG AUGAGGCCGA AAGGCCGAAA UGUUAG    36

( 2 ) INFORMATION FOR SEQ ID NO:347:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:347:

UGGACAACUG AUGAGGCCGA AAGGCCGAAA UCGGCC 36

( 2 ) INFORMATION FOR SEQ ID NO:348:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:348:

CUGGACACUG AUGAGGCCGA AAGGCCGAAA AUCGGC 36

( 2 ) INFORMATION FOR SEQ ID NO:349:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:349:

UCUGGACCUG AUGAGGCCGA AAGGCCGAAA AAUCGG 36

( 2 ) INFORMATION FOR SEQ ID NO:350:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:350:

UUGUCUGCUG AUGAGGCCGA AAGGCCGAAA CAAAAU 36

( 2 ) INFORMATION FOR SEQ ID NO:351:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:351:

CUGAAAGCUG AUGAGGCCGA AAGGCCGAAA UGCUGG 36

( 2 ) INFORMATION FOR SEQ ID NO:352:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:352:

CAUCUGACUG AUGAGGCCGA AAGGCCGAAA GGAUGC 36

( 2 ) INFORMATION FOR SEQ ID NO:353:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:353:

CCAUCUGCUG AUGAGGCCGA AAGGCCGAAA AGGAUG 36

( 2 ) INFORMATION FOR SEQ ID NO:354:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:354:

UCCAUCUCUG AUGAGGCCGA AAGGCCGAAA AAGGAU    36

( 2 ) INFORMATION FOR SEQ ID NO:355:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:355:

CCACCCCCUG AUGAGGCCGA AAGGCCGAAA UGUCUC    36

( 2 ) INFORMATION FOR SEQ ID NO:356:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:356:

UCAGGGACUG AUGAGGCCGA AAGGCCGAAA UGUCCA    36

( 2 ) INFORMATION FOR SEQ ID NO:357:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:357:

GUCAGGGCUG AUGAGGCCGA AAGGCCGAAA AUGUCC    36

( 2 ) INFORMATION FOR SEQ ID NO:358:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:358:

UGUCAGGCUG AUGAGGCCGA AAGGCCGAAA AAUGUC    36

( 2 ) INFORMATION FOR SEQ ID NO:359:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:359:

AUGACGGCUG AUGAGGCCGA AAGGCCGAAA UCACCU    36

( 2 ) INFORMATION FOR SEQ ID NO:360:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:360:

CUGUGAUCUG AUGAGGCCGA AAGGCCGAAA CGGGAU            36

( 2 ) INFORMATION FOR SEQ ID NO:361:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:361:

AGGCUGUCUG AUGAGGCCGA AAGGCCGAAA UGACGG            36

( 2 ) INFORMATION FOR SEQ ID NO:362:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:362:

CAGGUAGCUG AUGAGGCCGA AAGGCCGAAA GGCUGU            36

( 2 ) INFORMATION FOR SEQ ID NO:363:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:363:

CUCCAGGCUG AUGAGGCCGA AAGGCCGAAA GGAGGC            36

( 2 ) INFORMATION FOR SEQ ID NO:364:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:364:

GUGAUGGCUG AUGAGGCCGA AAGGCCGAAA CUCCAG            36

( 2 ) INFORMATION FOR SEQ ID NO:365:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:365:

CCCUUGUCUG AUGAGGCCGA AAGGCCGAAA UGGGAC            36

( 2 ) INFORMATION FOR SEQ ID NO:366:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:366:

AUGAAAUCUG AUGAGGCCGA AAGGCCGAAA CCCUUG  36

( 2 ) INFORMATION FOR SEQ ID NO:367:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:367:

UAGAUGACUG AUGAGGCCGA AAGGCCGAAA UGACCC  36

( 2 ) INFORMATION FOR SEQ ID NO:368:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:368:

GUAGAUGCUG AUGAGGCCGA AAGGCCGAAA AUGACC  36

( 2 ) INFORMATION FOR SEQ ID NO:369:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:369:

UGUAGAUCUG AUGAGGCCGA AAGGCCGAAA AAUGAC  36

( 2 ) INFORMATION FOR SEQ ID NO:370:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:370:

UCUUGUACUG AUGAGGCCGA AAGGCCGAAA UGAAAU  36

( 2 ) INFORMATION FOR SEQ ID NO:371:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:371:

AUUCUUGCUG AUGAGGCCGA AAGGCCGAAA GAUGAA  36

( 2 ) INFORMATION FOR SEQ ID NO:372:

( i ) SEQUENCE CHARACTERISTICS:
      ( A ) LENGTH: 36 base pairs ( B ) TYPE: nucleic acid
           ( C ) STRANDEDNESS: single
           ( D ) TOPOLOGY: linear ( x i ) SEQUENCE DESCRIPTION: SEQ ID NO:372:

CCUCUGACUG AUGAGGCCGA AAGGCCGAAA CAUUCU                    36

( 2 ) INFORMATION FOR SEQ ID NO:373:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:373:

GUCCUCUCUG AUGAGGCCGA AAGGCCGAAA GACAUU                    36

( 2 ) INFORMATION FOR SEQ ID NO:374:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:374:

GGAGGGGCUG AUGAGGCCGA AAGGCCGAAA GGUCCU                    36

( 2 ) INFORMATION FOR SEQ ID NO:375:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:375:

AGGUGGGCUG AUGAGGCCGA AAGGCCGAAA GGGGGA                    36

( 2 ) INFORMATION FOR SEQ ID NO:376:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:376:

GGGCGAGCUG AUGAGGCCGA AAGGCCGAAA GGUGGG                    36

( 2 ) INFORMATION FOR SEQ ID NO:377:

( i ) SEQUENCE CHARACTERISTICS:
           ( A ) LENGTH: 36 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:377:

UGGGCGACUG AUGAGGCCGA AAGGCCGAAA AGGUGG                    36

( 2 ) INFORMATION FOR SEQ ID NO:378:

( i ) SEQUENCE CHARACTERISTICS:
           ( A ) LENGTH: 36 base pairs
           ( B ) TYPE: nucleic acid
           ( C ) STRANDEDNESS: single (D) TOPOLOGY: linear (xi) SEQUENCE DESCRIPTION: SEQ ID NO:378:

UGUGGGCCUG AUGAGGCCGA AAGGCCGAAA GAAGGU    36

(2) INFORMATION FOR SEQ ID NO:379:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:379:

CAUGCGGCUG AUGAGGCCGA AAGGCCGAAA GUCCCC    36

(2) INFORMATION FOR SEQ ID NO:380:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:380:

CCAGAAGCUG AUGAGGCCGA AAGGCCGAAA CAGCAU    36

(2) INFORMATION FOR SEQ ID NO:381:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:381:

GAACCAGCUG AUGAGGCCGA AAGGCCGAAA GUACAG    36

(2) INFORMATION FOR SEQ ID NO:382:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:382:

AGAACCACUG AUGAGGCCGA AAGGCCGAAA AGUACA    36

(2) INFORMATION FOR SEQ ID NO:383:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:383:

CUCAGAGCUG AUGAGGCCGA AAGGCCGAAA CCAGAA    36

(2) INFORMATION FOR SEQ ID NO:384:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:384:

GCUCAGACUG AUGAGGCCGA AAGGCCGAAA ACCAGA            36

( 2 ) INFORMATION FOR SEQ ID NO:385:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:385:

UCGCUCACUG AUGAGGCCGA AAGGCCGAAA GAACCA            36

( 2 ) INFORMATION FOR SEQ ID NO:386:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:386:

AGUGGAACUG AUGAGGCCGA AAGGCCGAAA CUCGCU            36

( 2 ) INFORMATION FOR SEQ ID NO:387:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:387:

CGAGUGGCUG AUGAGGCCGA AAGGCCGAAA GACUCG            36

( 2 ) INFORMATION FOR SEQ ID NO:388:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:388:

GCGAGUGCUG AUGAGGCCGA AAGGCCGAAA AGACUC            36

( 2 ) INFORMATION FOR SEQ ID NO:389:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:389:

GGCCAGCCUG AUGAGGCCGA AAGGCCGAAA GUGGAA            36

( 2 ) INFORMATION FOR SEQ ID NO:390:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:390:

```
GGAAAGCCUG AUGAGGCCGA AAGGCCGAAA CCUUGG                                    36
```

( 2 ) INFORMATION FOR SEQ ID NO:391:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:391:

```
UCCUGGACUG AUGAGGCCGA AAGGCCGAAA GCUACC                                    36
```

( 2 ) INFORMATION FOR SEQ ID NO:392:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:392:

```
AUCCUGGCUG AUGAGGCCGA AAGGCCGAAA AGCUAC                                    36
```

( 2 ) INFORMATION FOR SEQ ID NO:393:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:393:

```
CAUCCUGCUG AUGAGGCCGA AAGGCCGAAA AAGCUA                                    36
```

( 2 ) INFORMATION FOR SEQ ID NO:394:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:394:

```
UGAGCAUCUG AUGAGGCCGA AAGGCCGAAA GGCGGC                                    36
```

( 2 ) INFORMATION FOR SEQ ID NO:395:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:395:

```
UCAGGCUCUG AUGAGGCCGA AAGGCCGAAA GCAUGA                                    36
```

( 2 ) INFORMATION FOR SEQ ID NO:396:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:396:

```
UGCCUUGCUG AUGAGGCCGA AAGGCCGAAA CUCGUC                                    36
```

( 2 ) INFORMATION FOR SEQ ID NO:397:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:397:

CUGCCUUCUG AUGAGGCCGA AAGGCCGAAA ACUCGU 36

( 2 ) INFORMATION FOR SEQ ID NO:398:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:398:

GGUGUUGCUG AUGAGGCCGA AAGGCCGAAA GCCCCA 36

( 2 ) INFORMATION FOR SEQ ID NO:399:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:399:

UGGUGUUCUG AUGAGGCCGA AAGGCCGAAA AGCCCC 36

( 2 ) INFORMATION FOR SEQ ID NO:400:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:400:

CUUGGAACUG AUGAGGCCGA AAGGCCGAAA UUUCCU 36

( 2 ) INFORMATION FOR SEQ ID NO:401:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:401:

CUCUUGGCUG AUGAGGCCGA AAGGCCGAAA GAUUUC 36

( 2 ) INFORMATION FOR SEQ ID NO:402:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:402:

CCUCUUGCUG AUGAGGCCGA AAGGCCGAAA AGAUUU 36

( 2 ) INFORMATION FOR SEQ ID NO:403:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:403:

CGCCGACCUG AUGAGGCCGA AAGGCCGAAA CCUCUU 36

( 2 ) INFORMATION FOR SEQ ID NO:404:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:404:

AGCCGCCCUG AUGAGGCCGA AAGGCCGAAA CAACCU 36

( 2 ) INFORMATION FOR SEQ ID NO:405:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:405:

GCUGGGGCUG AUGAGGCCGA AAGGCCGAAA GCCGCC 36

( 2 ) INFORMATION FOR SEQ ID NO:406:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:406:

GGCUGGGCUG AUGAGGCCGA AAGGCCGAAA AGCCGC 36

( 2 ) INFORMATION FOR SEQ ID NO:407:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:407:

GGACGGUCUG AUGAGGCCGA AAGGCCGAAA CUUGGG 36

( 2 ) INFORMATION FOR SEQ ID NO:408:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:408:

GGCAGUGCUG AUGAGGCCGA AAGGCCGAAA CGGUGA 36

( 2 ) INFORMATION FOR SEQ ID NO:409:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:409:

GCAUCUUCUG AUGAGGCCGA AAGGCCGAAA GGCAGU       36

(2) INFORMATION FOR SEQ ID NO:410:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:410:

GGCAGGACUG AUGAGGCCGA AAGGCCGAAA UCUUGG       36

(2) INFORMATION FOR SEQ ID NO:411:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:411:

UUGGCAGCUG AUGAGGCCGA AAGGCCGAAA GAUCUU       36

(2) INFORMATION FOR SEQ ID NO:412:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:412:

UGACCACCUG AUGAGGCCGA AAGGCCGAAA CUCCCU       36

(2) INFORMATION FOR SEQ ID NO:413:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:413:

AAGAAUUCUG AUGAGGCCGA AAGGCCGAAA CCACGA       36

(2) INFORMATION FOR SEQ ID NO:414:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (xi) SEQUENCE DESCRIPTION: SEQ ID NO:414:

ACUGAAGCUG AUGAGGCCGA AAGGCCGAAA UUGACC       36

(2) INFORMATION FOR SEQ ID NO:415:

(i) SEQUENCE CHARACTERISTICS:
      (A) LENGTH: 36 base pairs
      (B) TYPE: nucleic acid (C) STRANDEDNESS: single
        (D) TOPOLOGY: linear (xi) SEQUENCE DESCRIPTION: SEQ ID NO:415:

CACUGAACUG AUGAGGCCGA AAGGCCGAAA AUUGAC  36

(2) INFORMATION FOR SEQ ID NO:416:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:416:

AUCACUGCUG AUGAGGCCGA AAGGCCGAAA GAAUUG  36

(2) INFORMATION FOR SEQ ID NO:417:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:417:

CAUCACUCUG AUGAGGCCGA AAGGCCGAAA AGAAUU  36

(2) INFORMATION FOR SEQ ID NO:418:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:418:

AAAGAGGCUG AUGAGGCCGA AAGGCCGAAA UUUCAC  36

(2) INFORMATION FOR SEQ ID NO:419:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:419:

GAAAGAGCUG AUGAGGCCGA AAGGCCGAAA AUUUCA  36

(2) INFORMATION FOR SEQ ID NO:420:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:420:

GUGGAAACUG AUGAGGCCGA AAGGCCGAAA GGAAUU  36

(2) INFORMATION FOR SEQ ID NO:421:

(i) SEQUENCE CHARACTERISTICS:
        (A) LENGTH: 36 base pairs
        (B) TYPE: nucleic acid
        (C) STRANDEDNESS: single
        (D) TOPOLOGY: linear ( x i ) SEQUENCE DESCRIPTION: SEQ ID NO:421:

GCGUGGACUG AUGAGGCCGA AAGGCCGAAA GAGGAA    36

( 2 ) INFORMATION FOR SEQ ID NO:422:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:422:

GGCGUGGCUG AUGAGGCCGA AAGGCCGAAA AGAGGA    36

( 2 ) INFORMATION FOR SEQ ID NO:423:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:423:

GGGCGUGCUG AUGAGGCCGA AAGGCCGAAA AAGAGG    36

( 2 ) INFORMATION FOR SEQ ID NO:424:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:424:

GCUACAGCUG AUGAGGCCGA AAGGCCGAAA UGUUGC    36

( 2 ) INFORMATION FOR SEQ ID NO:425:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:425:

AGCUACACUG AUGAGGCCGA AAGGCCGAAA AUGUUG    36

( 2 ) INFORMATION FOR SEQ ID NO:426:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:426:

UGUAAGCCUG AUGAGGCCGA AAGGCCGAAA CAGAAU    36

( 2 ) INFORMATION FOR SEQ ID NO:427:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:427:

AAUGUGUCUG AUGAGGCCGA AAGGCCGAAA GCUACA    36

(2) INFORMATION FOR SEQ ID NO:428:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:428:

AAAUGUGCUG AUGAGGCCGA AAGGCCGAAA AGCUAC    36

(2) INFORMATION FOR SEQ ID NO:429:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:429:

CUCUUCACUG AUGAGGCCGA AAGGCCGAAA UGUGUA    36

(2) INFORMATION FOR SEQ ID NO:430:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:430:

CCUCUUCCUG AUGAGGCCGA AAGGCCGAAA AUGUGU    36

(2) INFORMATION FOR SEQ ID NO:431:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:431:

GUCACGACUG AUGAGGCCGA AAGGCCGAAA UCCUCU    36

(2) INFORMATION FOR SEQ ID NO:432:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:432:

UAGUCACCUG AUGAGGCCGA AAGGCCGAAA UAUCCU    36

(2) INFORMATION FOR SEQ ID NO:433:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:433:

UGGACGGCUG AUGAGGCCGA AAGGCCGAAA GUCACG    36

( 2 ) INFORMATION FOR SEQ ID NO:434:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:434:

AGGCCUGCUG AUGAGGCCGA AAGGCCGAAA CGGUAG                      36

( 2 ) INFORMATION FOR SEQ ID NO:435:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:435:

AGAAUAGCUG AUGAGGCCGA AAGGCCGAAA GGCCUG                      36

( 2 ) INFORMATION FOR SEQ ID NO:436:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:436:

CUUAGAACUG AUGAGGCCGA AAGGCCGAAA GGAGGC                      36

( 2 ) INFORMATION FOR SEQ ID NO:437:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:437:

UUCUUAGCUG AUGAGGCCGA AAGGCCGAAA UAGGAG                      36

( 2 ) INFORMATION FOR SEQ ID NO:438:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:438:

UUUCUUACUG AUGAGGCCGA AAGGCCGAAA AUAGGA                      36

( 2 ) INFORMATION FOR SEQ ID NO:439:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:439:

UUUUUCUCUG AUGAGGCCGA AAGGCCGAAA GAAUAG                      36

( 2 ) INFORMATION FOR SEQ ID NO:440:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:440:

UUAAGAACUG AUGAGGCCGA AAGGCCGAAA GCUUUU         36

( 2 ) INFORMATION FOR SEQ ID NO:441:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:441:

GCUUAAGCUG AUGAGGCCGA AAGGCCGAAA GAGCUU         36

( 2 ) INFORMATION FOR SEQ ID NO:442:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:442:

GGCUUAACUG AUGAGGCCGA AAGGCCGAAA AGAGCU         36

( 2 ) INFORMATION FOR SEQ ID NO:443:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:443:

GAGGCUUCUG AUGAGGCCGA AAGGCCGAAA GAAGAG         36

( 2 ) INFORMATION FOR SEQ ID NO:444:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:444:

AGAGGCUCUG AUGAGGCCGA AAGGCCGAAA AGAAGA         36

( 2 ) INFORMATION FOR SEQ ID NO:445:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:445:

AAUCCAACUG AUGAGGCCGA AAGGCCGAAA GGCUUA         36

( 2 ) INFORMATION FOR SEQ ID NO:446:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:446:

GAAAUCCCUG AUGAGGCCGA AAGGCCGAAA GAGGCU  36

( 2 ) INFORMATION FOR SEQ ID NO:447:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:447:

AUCUGGACUG AUGAGGCCGA AAGGCCGAAA UCCAAG  36

( 2 ) INFORMATION FOR SEQ ID NO:448:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:448:

AAUCUGGCUG AUGAGGCCGA AAGGCCGAAA AUCCAA  36

( 2 ) INFORMATION FOR SEQ ID NO:449:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:449:

UAAUCUGCUG AUGAGGCCGA AAGGCCGAAA AAUCCA  36

( 2 ) INFORMATION FOR SEQ ID NO:450:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:450:

UUGGUGUCUG AUGAGGCCGA AAGGCCGAAA UCUGGA  36

( 2 ) INFORMATION FOR SEQ ID NO:451:

( i ) SEQUENCE CHARACTERISTICS:
   ( A ) LENGTH: 36 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:451:

UUUGGUGCUG AUGAGGCCGA AAGGCCGAAA AUCUGG  36

( 2 ) INFORMATION FOR SEQ ID NO:452:

( i ) SEQUENCE CHARACTERISTICS:
   ( A ) LENGTH: 36 base pairs (B) TYPE: nucleic acid
        (C) STRANDEDNESS: single
        (D) TOPOLOGY: linear (x i) SEQUENCE DESCRIPTION: SEQ ID NO:452:

AGUUGGACUG AUGAGGCCGA AAGGCCGAAA CAGUCU                                              36

(2) INFORMATION FOR SEQ ID NO:453:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:453:

AAGUUGGCUG AUGAGGCCGA AAGGCCGAAA ACAGUC                                              36

(2) INFORMATION FOR SEQ ID NO:454:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:454:

CAAGUUGCUG AUGAGGCCGA AAGGCCGAAA AACAGU                                              36

(2) INFORMATION FOR SEQ ID NO:455:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:455:

CUCAGUCCUG AUGAGGCCGA AAGGCCGAAA GUUGGA                                              36

(2) INFORMATION FOR SEQ ID NO:456:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:456:

GGACUCGCUG AUGAGGCCGA AAGGCCGAAA GCUGCU                                              36

(2) INFORMATION FOR SEQ ID NO:457:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:457:

CUGGAUGCUG AUGAGGCCGA AAGGCCGAAA CUCGGA                                              36

(2) INFORMATION FOR SEQ ID NO:458:

(i) SEQUENCE CHARACTERISTICS:
        (A) LENGTH: 36 base pairs
        (B) TYPE: nucleic acid
        (C) STRANDEDNESS: single ( D ) TOPOLOGY: linear ( x i ) SEQUENCE DESCRIPTION: SEQ ID NO:458:

AGCUCUGCUG AUGAGGCCGA AAGGCCGAAA UGGACU　　　　　　　　　　　　36

( 2 ) INFORMATION FOR SEQ ID NO:459:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:459:

CUGCAGGCUG AUGAGGCCGA AAGGCCGAAA GCUCUG　　　　　　　　　　　　36

( 2 ) INFORMATION FOR SEQ ID NO:460:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:460:

ACUGCAGCUG AUGAGGCCGA AAGGCCGAAA AGCUCU　　　　　　　　　　　　36

( 2 ) INFORMATION FOR SEQ ID NO:461:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:461:

GAUCAUUCUG AUGAGGCCGA AAGGCCGAAA CUGCAG　　　　　　　　　　　　36

( 2 ) INFORMATION FOR SEQ ID NO:462:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:462:

CAGCGGUCUG AUGAGGCCGA AAGGCCGAAA UCAUUG　　　　　　　　　　　　36

( 2 ) INFORMATION FOR SEQ ID NO:463:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:463:

CCUCAGGCUG AUGAGGCCGA AAGGCCGAAA UGCCCA　　　　　　　　　　　　36

( 2 ) INFORMATION FOR SEQ ID NO:464:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:464:

GAGACAUCUG AUGAGGCCGA AAGGCCGAAA CCUCAG   36

( 2 ) INFORMATION FOR SEQ ID NO:465:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:465:

GAGCCGACUG AUGAGGCCGA AAGGCCGAAA CAUGAC   36

( 2 ) INFORMATION FOR SEQ ID NO:466:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:466:

UCGAGCCCUG AUGAGGCCGA AAGGCCGAAA GACAUG   36

( 2 ) INFORMATION FOR SEQ ID NO:467:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:467:

CUACCUCCUG AUGAGGCCGA AAGGCCGAAA GCCGAG   36

( 2 ) INFORMATION FOR SEQ ID NO:468:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:468:

UAAACACCUG AUGAGGCCGA AAGGCCGAAA CCUCGA   36

( 2 ) INFORMATION FOR SEQ ID NO:469:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:469:

GGCUGUACUG AUGAGGCCGA AAGGCCGAAA CACUAC   36

( 2 ) INFORMATION FOR SEQ ID NO:470:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:470:

GGGCUGUCUG AUGAGGCCGA AAGGCCGAAA ACACUA    36

( 2 ) INFORMATION FOR SEQ ID NO:471:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:471:

AGGGCUGCUG AUGAGGCCGA AAGGCCGAAA AACACU    36

( 2 ) INFORMATION FOR SEQ ID NO:472:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:472:

UGUUCAUCUG AUGAGGCCGA AAGGCCGAAA GGGCUG    36

( 2 ) INFORMATION FOR SEQ ID NO:473:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:473:

UGUCGAACUG AUGAGGCCGA AAGGCCGAAA GGCUCA    36

( 2 ) INFORMATION FOR SEQ ID NO:474:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:474:

GAUGUCGCUG AUGAGGCCGA AAGGCCGAAA GAGGCU    36

( 2 ) INFORMATION FOR SEQ ID NO:475:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:475:

UGAUGUCCUG AUGAGGCCGA AAGGCCGAAA AGAGGC    36

( 2 ) INFORMATION FOR SEQ ID NO:476:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:476:

GGUUGAUCUG AUGAGGCCGA AAGGCCGAAA UGUCGA    36

( 2 ) INFORMATION FOR SEQ ID NO:477:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:477:

CAGGGUUCUG AUGAGGCCGA AAGGCCGAAA UGAUGU    36

( 2 ) INFORMATION FOR SEQ ID NO:478:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:478:

GAGUGAUCUG AUGAGGCCGA AAGGCCGAAA UCUCAG    36

( 2 ) INFORMATION FOR SEQ ID NO:479:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:479:

CGAGUGACUG AUGAGGCCGA AAGGCCGAAA AUCUCA    36

( 2 ) INFORMATION FOR SEQ ID NO:480:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:480:

CUCGAGUCUG AUGAGGCCGA AAGGCCGAAA UAAUCU    36

( 2 ) INFORMATION FOR SEQ ID NO:481:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:481:

CCAUCUCCUG AUGAGGCCGA AAGGCCGAAA GUGAUA    36

( 2 ) INFORMATION FOR SEQ ID NO:482:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:482:

CAGCAGGCUG AUGAGGCCGA AAGGCCGAAA GCCAUC    36

( 2 ) INFORMATION FOR SEQ ID NO:483:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:483:

GCAGCAGCUG AUGAGGCCGA AAGGCCGAAA AGCCAU    36

( 2 ) INFORMATION FOR SEQ ID NO:484:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:484:

GAAGCCACUG AUGAGGCCGA AAGGCCGAAA GUCCAU    36

( 2 ) INFORMATION FOR SEQ ID NO:485:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:485:

GGAAGCCCUG AUGAGGCCGA AAGGCCGAAA AGUCCA    36

( 2 ) INFORMATION FOR SEQ ID NO:486:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:486:

CUCAGGGCUG AUGAGGCCGA AAGGCCGAAA GCCAAA    36

( 2 ) INFORMATION FOR SEQ ID NO:487:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:487:

GCUCAGGCUG AUGAGGCCGA AAGGCCGAAA AGCCAA    36

( 2 ) INFORMATION FOR SEQ ID NO:488:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:488:

UGGAGGACUG AUGAGGCCGA AAGGCCGAAA UCCACC    36

( 2 ) INFORMATION FOR SEQ ID NO:489:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:489:

CUGGAGGCUG AUGAGGCCGA AAGGCCGAAA AUCCAC    36

(2) INFORMATION FOR SEQ ID NO:490:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:490:

UCUGGAGCUG AUGAGGCCGA AAGGCCGAAA AAUCCA    36

(2) INFORMATION FOR SEQ ID NO:491:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:491:

AGCUCUGCUG AUGAGGCCGA AAGGCCGAAA GGAAAU    36

(2) INFORMATION FOR SEQ ID NO:492:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:492:

CUAGCUCCUG AUGAGGCCGA AAGGCCGAAA GCUCUG    36

(2) INFORMATION FOR SEQ ID NO:493:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:493:

AGACUUCCUG AUGAGGCCGA AAGGCCGAAA GCUCAA    36

(2) INFORMATION FOR SEQ ID NO:494:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:494:

CCUUGGACUG AUGAGGCCGA AAGGCCGAAA CUUCUA    36

(2) INFORMATION FOR SEQ ID NO:495:

(i) SEQUENCE CHARACTERISTICS:
        (A) LENGTH: 36 base pairs
        (B) TYPE: nucleic acid ( C ) STRANDEDNESS: single
        ( D ) TOPOLOGY: linear ( x i ) SEQUENCE DESCRIPTION: SEQ ID NO:495:

CUCCUUGCUG AUGAGGCCGA AAGGCCGAAA GACUUC                36

( 2 ) INFORMATION FOR SEQ ID NO:496:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:496:

CCAUCCCUG AUGAGGCCGA AAGGCCGAAA CCUCCU                 36

( 2 ) INFORMATION FOR SEQ ID NO:497:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:497:

CUGCUACCUG AUGAGGCCGA AAGGCCGAAA GCCCCA                36

( 2 ) INFORMATION FOR SEQ ID NO:498:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:498:

CUUCUGCCUG AUGAGGCCGA AAGGCCGAAA CAAGCC                36

( 2 ) INFORMATION FOR SEQ ID NO:499:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:499:

CAGCUGUCUG AUGAGGCCGA AAGGCCGAAA GCCUGG                36

( 2 ) INFORMATION FOR SEQ ID NO:500:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:500:

UGGAGGACUG AUGAGGCCGA AAGGCCGAAA CACCAG                36

( 2 ) INFORMATION FOR SEQ ID NO:501:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:501:

GCUGGAGCUG AUGAGGCCGA AAGGCCGAAA GACACC    36

( 2 ) INFORMATION FOR SEQ ID NO:502:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:502:

CACGCUGCUG AUGAGGCCGA AAGGCCGAAA GGAGAC    36

( 2 ) INFORMATION FOR SEQ ID NO:503:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:503:

CUAACCCCUG AUGAGGCCGA AAGGCCGAAA CUUCCA    36

( 2 ) INFORMATION FOR SEQ ID NO:504:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:504:

UACUCCUCUG AUGAGGCCGA AAGGCCGAAA CCCAAC    36

( 2 ) INFORMATION FOR SEQ ID NO:505:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:505:

GUACUCCCUG AUGAGGCCGA AAGGCCGAAA ACCCAA    36

( 2 ) INFORMATION FOR SEQ ID NO:506:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:506:

AUCUCCGCUG AUGAGGCCGA AAGGCCGAAA CUCCUA    36

( 2 ) INFORMATION FOR SEQ ID NO:507:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:507:

GGGAGCCCUG AUGAGGCCGA AAGGCCGAAA UCUCCA 36

( 2 ) INFORMATION FOR SEQ ID NO:508:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:508:

GAGUUGGCUG AUGAGGCCGA AAGGCCGAAA GCCAAU 36

( 2 ) INFORMATION FOR SEQ ID NO:509:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:509:

UAGGGAGCUG AUGAGGCCGA AAGGCCGAAA GUUGGG 36

( 2 ) INFORMATION FOR SEQ ID NO:510:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:510:

GGAUAGGCUG AUGAGGCCGA AAGGCCGAAA GGAGUU 36

( 2 ) INFORMATION FOR SEQ ID NO:511:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:511:

UUUAGGACUG AUGAGGCCGA AAGGCCGAAA GGGAGG 36

( 2 ) INFORMATION FOR SEQ ID NO:512:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:512:

CCUUUAGCUG AUGAGGCCGA AAGGCCGAAA UAGGGA 36

( 2 ) INFORMATION FOR SEQ ID NO:513:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:513:

GGGCCUUCUG AUGAGGCCGA AAGGCCGAAA GGAUAG 36

( 2 ) INFORMATION FOR SEQ ID NO:514:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:514:

GCACUUUCUG AUGAGGCCGA AAGGCCGAAA UGCCAG　　　　　　　　　　36

( 2 ) INFORMATION FOR SEQ ID NO:515:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:515:

AGCACUUCUG AUGAGGCCGA AAGGCCGAAA AUGCCA　　　　　　　　　　36

( 2 ) INFORMATION FOR SEQ ID NO:516:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:516:

GGCGCCUCCU ACGAG　　　　　　　　　　15

( 2 ) INFORMATION FOR SEQ ID NO:517:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:517:

GCCUCCUACG AGGCU　　　　　　　　　　15

( 2 ) INFORMATION FOR SEQ ID NO:518:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:518:

GCCUCCUACG AGGCU　　　　　　　　　　15

( 2 ) INFORMATION FOR SEQ ID NO:519:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:519:

CUGGCAUCGU GUGUC　　　　　　　　　　15

( 2 ) INFORMATION FOR SEQ ID NO:520:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:520:

CGUGUGUCGC AUCAC         15

( 2 ) INFORMATION FOR SEQ ID NO:521:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:521:

CGUGUGUCGC AUCAC         15

( 2 ) INFORMATION FOR SEQ ID NO:522:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:522:

GUCGCAUCAC CAAGC         15

( 2 ) INFORMATION FOR SEQ ID NO:523:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:523:

CCGCCCUCUU GGUGU         15

( 2 ) INFORMATION FOR SEQ ID NO:524:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:524:

UUGGUGUUGA ACCAA         15

( 2 ) INFORMATION FOR SEQ ID NO:525:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:525:

AGGUGGUCCA GACGG         15

( 2 ) INFORMATION FOR SEQ ID NO:526:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:526:

AGGUGGUCCA GACGG 15

( 2 ) INFORMATION FOR SEQ ID NO:527:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:527:

AGGUGGUCCA GACGG 15

( 2 ) INFORMATION FOR SEQ ID NO:528:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:528:

ACGGCCUUCC AGCGC 15

( 2 ) INFORMATION FOR SEQ ID NO:529:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:529:

CGGCCUUCCA GCGCG 15

( 2 ) INFORMATION FOR SEQ ID NO:530:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:530:

GCCGGCUAUC CGGAC 15

( 2 ) INFORMATION FOR SEQ ID NO:531:

( i ) SEQUENCE CHARACTERISTICS:
  ( A ) LENGTH: 15 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:531:

CGGACGUCAG CGGCG 15

( 2 ) INFORMATION FOR SEQ ID NO:532:

( i ) SEQUENCE CHARACTERISTICS:
  ( A ) LENGTH: 15 base pairs (B) TYPE: nucleic acid
(C) STRANDEDNESS: single
(D) TOPOLOGY: linear (xi) SEQUENCE DESCRIPTION: SEQ ID NO:532:

CGGACGUCAG CGGCG 15

(2) INFORMATION FOR SEQ ID NO:533:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:533:

CGGACGUCAG CGGCG 15

(2) INFORMATION FOR SEQ ID NO:534:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:534:

UGAUGCUCCU CGGCC 15

(2) INFORMATION FOR SEQ ID NO:535:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:535:

UGCUCCUCGG CCGGG 15

(2) INFORMATION FOR SEQ ID NO:536:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:536:

GCCGGGUCAA GUACG 15

(2) INFORMATION FOR SEQ ID NO:537:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:537:

GCCGGGUCAA GUACG 15

(2) INFORMATION FOR SEQ ID NO:538:

(i) SEQUENCE CHARACTERISTICS:
(A) LENGTH: 15 base pairs
(B) TYPE: nucleic acid
(C) STRANDEDNESS: single ( D ) TOPOLOGY: linear ( x i ) SEQUENCE DESCRIPTION: SEQ ID NO:538:

GUCAAGUACG GGCUG                                                                15

( 2 ) INFORMATION FOR SEQ ID NO:539:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:539:

ACAACCUCCA GAUCA                                                                15

( 2 ) INFORMATION FOR SEQ ID NO:540:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:540:

ACAACCUCCA GAUCA                                                                15

( 2 ) INFORMATION FOR SEQ ID NO:541:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:541:

UCCAGAUCAG CCACC                                                                15

( 2 ) INFORMATION FOR SEQ ID NO:542:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:542:

CACCUGUCCA UCGCC                                                                15

( 2 ) INFORMATION FOR SEQ ID NO:543:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:543:

UGUCCAUCGC CAGCA                                                                15

( 2 ) INFORMATION FOR SEQ ID NO:544:

( i ) SEQUENCE CHARACTERISTICS:
                ( A ) LENGTH: 15 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:544:

AGACCAUCGA CGUCG                                                                                          15

( 2 ) INFORMATION FOR SEQ ID NO:545:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:545:

UCGACGUCGC CAUCC                                                                                          15

( 2 ) INFORMATION FOR SEQ ID NO:546:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:546:

UCGCCAUCCA GAACG                                                                                          15

( 2 ) INFORMATION FOR SEQ ID NO:547:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:547:

UCGCCAUCCA GAACG                                                                                          15

( 2 ) INFORMATION FOR SEQ ID NO:548:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:548:

AACGUGUCCG UGGUC                                                                                          15

( 2 ) INFORMATION FOR SEQ ID NO:549:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:549:

AACGUGUCCG UGGUC                                                                                          15

( 2 ) INFORMATION FOR SEQ ID NO:550:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:550:

CCGUGGUCUU CAAGG    15

( 2 ) INFORMATION FOR SEQ ID NO:551:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:551:

CCGUGGUCUU CAAGG    15

( 2 ) INFORMATION FOR SEQ ID NO:552:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:552:

GUGGUCUUCA AGGGG    15

( 2 ) INFORMATION FOR SEQ ID NO:553:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:553:

UGGUCUUCAA GGGGA    15

( 2 ) INFORMATION FOR SEQ ID NO:554:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:554:

CUGAACUACA GCUAC    15

( 2 ) INFORMATION FOR SEQ ID NO:555:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:555:

CUGAACUACA GCUAC    15

( 2 ) INFORMATION FOR SEQ ID NO:556:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:556:

UACAGCUACA CGAGU    15

(2) INFORMATION FOR SEQ ID NO:557:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:557:

UACAGCUACA CGAGU 15

(2) INFORMATION FOR SEQ ID NO:558:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:558:

UACAGCUACA CGAGU 15

(2) INFORMATION FOR SEQ ID NO:559:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:559:

UGGGGGUUGG GCAUC 15

(2) INFORMATION FOR SEQ ID NO:560:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:560:

UGGGCAUCAA UCAGU 15

(2) INFORMATION FOR SEQ ID NO:561:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:561:

CAUCAAUCAG UCUGU 15

(2) INFORMATION FOR SEQ ID NO:562:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:562:

CAUCAAUCAG UCUGU 15

(2) INFORMATION FOR SEQ ID NO:563:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:563:

AAUCAGUCUG UCGAC      15

( 2 ) INFORMATION FOR SEQ ID NO:564:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:564:

AGUCUGUCGA CUUCG      15

( 2 ) INFORMATION FOR SEQ ID NO:565:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:565:

AGUCUGUCGA CUUCG      15

( 2 ) INFORMATION FOR SEQ ID NO:566:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:566:

GUCGACUUCG AGAUC      15

( 2 ) INFORMATION FOR SEQ ID NO:567:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:567:

UCGACUUCGA GAUCG      15

( 2 ) INFORMATION FOR SEQ ID NO:568:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:568:

UCGAGAUCGA CUCUG      15

( 2 ) INFORMATION FOR SEQ ID NO:569:

( i ) SEQUENCE CHARACTERISTICS:

(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:569:

UCGAGAUCGA CUCUG 15

(2) INFORMATION FOR SEQ ID NO:570:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:570:

UCGAGAUCGA CUCUG 15

(2) INFORMATION FOR SEQ ID NO:571:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:571:

UCGAGAUCGA CUCUG 15

(2) INFORMATION FOR SEQ ID NO:572:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:572:

AUCGACUCUG CCAUU 15

(2) INFORMATION FOR SEQ ID NO:573:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:573:

AUCGACUCUG CCAUU 15

(2) INFORMATION FOR SEQ ID NO:574:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:574:

AUCGACUCUG CCAUU 15

(2) INFORMATION FOR SEQ ID NO:575:

(i) SEQUENCE CHARACTERISTICS:
(A) LENGTH: 15 base pairs
(B) TYPE: nucleic acid (C) STRANDEDNESS: single
(D) TOPOLOGY: linear (xi) SEQUENCE DESCRIPTION: SEQ ID NO:575:

CUGCCAUUGA CCUCC    15

(2) INFORMATION FOR SEQ ID NO:576:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:576:

UUGACCUCCA GAUCA    15

(2) INFORMATION FOR SEQ ID NO:577:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:577:

UUGACCUCCA GAUCA    15

(2) INFORMATION FOR SEQ ID NO:578:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:578:

UUGACCUCCA GAUCA    15

(2) INFORMATION FOR SEQ ID NO:579:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:579:

UCCAGAUCAA CACAG    15

(2) INFORMATION FOR SEQ ID NO:580:

(i) SEQUENCE CHARACTERISTICS:
(A) LENGTH: 15 base pairs
(B) TYPE: nucleic acid
(C) STRANDEDNESS: single
(D) TOPOLOGY: linear (xi) SEQUENCE DESCRIPTION: SEQ ID NO:580:

UCCAGAUCAA CACAG    15

(2) INFORMATION FOR SEQ ID NO:581:

(i) SEQUENCE CHARACTERISTICS:
(A) LENGTH: 15 base pairs
(B) TYPE: nucleic acid
(C) STRANDEDNESS: single
(D) TOPOLOGY: linear ( x i ) SEQUENCE DESCRIPTION: SEQ ID NO:581:

UCCAGAUCAA CACAG 15

( 2 ) INFORMATION FOR SEQ ID NO:582:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:582:

GACUGCUACC UGGCU 15

( 2 ) INFORMATION FOR SEQ ID NO:583:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:583:

GACUGCUACC UGGCU 15

( 2 ) INFORMATION FOR SEQ ID NO:584:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:584:

CCUGGCUUUC CAUAA 15

( 2 ) INFORMATION FOR SEQ ID NO:585:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:585:

CCUGGCUUUC CAUAA 15

( 2 ) INFORMATION FOR SEQ ID NO:586:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:586:

CCUGGCUUUC CAUAA 15

( 2 ) INFORMATION FOR SEQ ID NO:587:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:587:

CUGGCUUUCC AUAAA 15

( 2 ) INFORMATION FOR SEQ ID NO:588:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:588:

CUGGCUUUCC AUAAA 15

( 2 ) INFORMATION FOR SEQ ID NO:589:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:589:

UGGCUUUCCA UAAAC 15

( 2 ) INFORMATION FOR SEQ ID NO:590:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:590:

UGGCUUUCCA UAAAC 15

( 2 ) INFORMATION FOR SEQ ID NO:591:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:591:

UUUCCAUAAA CUGCU 15

( 2 ) INFORMATION FOR SEQ ID NO:592:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:592:

AACUGCUCCU GCACC 15

( 2 ) INFORMATION FOR SEQ ID NO:593:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:593:

UGCACCUCCA GGGGG 15

( 2 ) INFORMATION FOR SEQ ID NO:594:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:594:

GGUGGCUCAA GCAGC       15

( 2 ) INFORMATION FOR SEQ ID NO:595:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:595:

GGUGGCUCAA GCAGC       15

( 2 ) INFORMATION FOR SEQ ID NO:596:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:596:

GGUGGCUCAA GCAGC       15

( 2 ) INFORMATION FOR SEQ ID NO:597:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:597:

GGUGGCUCAA GCAGC       15

( 2 ) INFORMATION FOR SEQ ID NO:598:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:598:

CAGCUCUUCA CAAAC       15

( 2 ) INFORMATION FOR SEQ ID NO:599:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:599:

CAGCUCUUCA CAAAC       15

( 2 ) INFORMATION FOR SEQ ID NO:600:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:600:

AGCUCUUCAC AAACU         15

( 2 ) INFORMATION FOR SEQ ID NO:601:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:601:

AGCUCUUCAC AAACU         15

( 2 ) INFORMATION FOR SEQ ID NO:602:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:602:

ACAAACUUCA UCUCC         15

( 2 ) INFORMATION FOR SEQ ID NO:603:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:603:

CAAACUUCAU CUCCU         15

( 2 ) INFORMATION FOR SEQ ID NO:604:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:604:

ACUUCAUCUC CUUCA         15

( 2 ) INFORMATION FOR SEQ ID NO:605:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:605:

UUCAUCUCCU UCACC         15

( 2 ) INFORMATION FOR SEQ ID NO:606:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:606:

AUCUCCUUCA CCCUG 15

( 2 ) INFORMATION FOR SEQ ID NO:607:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:607:

AUCUCCUUCA CCCUG 15

( 2 ) INFORMATION FOR SEQ ID NO:608:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:608:

AUCUCCUUCA CCCUG 15

( 2 ) INFORMATION FOR SEQ ID NO:609:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:609:

UCUCCUUCAC CCUGA 15

( 2 ) INFORMATION FOR SEQ ID NO:610:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:610:

AGCUGAUUCU GAAGC 15

( 2 ) INFORMATION FOR SEQ ID NO:611:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:611:

GACAGGUCUG CAAUG 15

( 2 ) INFORMATION FOR SEQ ID NO:612:

( i ) SEQUENCE CHARACTERISTICS:
    ( A ) LENGTH: 15 base pairs (B) TYPE: nucleic acid
        (C) STRANDEDNESS: single
        (D) TOPOLOGY: linear (x i) SEQUENCE DESCRIPTION: SEQ ID NO:612:

GACAGGUCUG CAAUG        15

(2) INFORMATION FOR SEQ ID NO:613:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:613:

AUGAGAUCAA CACCA        15

(2) INFORMATION FOR SEQ ID NO:614:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:614:

ACACCAUCUC CAACA        15

(2) INFORMATION FOR SEQ ID NO:615:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:615:

ACACCAUCUC CAACA        15

(2) INFORMATION FOR SEQ ID NO:616:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:616:

ACCAUCUCCA ACAUC        15

(2) INFORMATION FOR SEQ ID NO:617:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (x i) SEQUENCE DESCRIPTION: SEQ ID NO:617:

CCAACAUCAU GGCUG        15

(2) INFORMATION FOR SEQ ID NO:618:

(i) SEQUENCE CHARACTERISTICS:
        (A) LENGTH: 15 base pairs
        (B) TYPE: nucleic acid
        (C) STRANDEDNESS: single ( D ) TOPOLOGY: linear ( x i ) SEQUENCE DESCRIPTION: SEQ ID NO:618:

CCAACAUCAU GGCUG                                                                                    15

( 2 ) INFORMATION FOR SEQ ID NO:619:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:619:

GCUGACUUUG UCCAG                                                                                    15

( 2 ) INFORMATION FOR SEQ ID NO:620:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:620:

CUGACUUUGU CCAGA                                                                                    15

( 2 ) INFORMATION FOR SEQ ID NO:621:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:621:

ACUUUGUCCA GACGA                                                                                    15

( 2 ) INFORMATION FOR SEQ ID NO:622:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:622:

CCAGCAUCCU CUCAG                                                                                    15

( 2 ) INFORMATION FOR SEQ ID NO:623:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:623:

GCAUCCUCUC AGAUG                                                                                    15

( 2 ) INFORMATION FOR SEQ ID NO:624:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:624:

AUCCUCUCAG AUGGA 15

( 2 ) INFORMATION FOR SEQ ID NO:625:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:625:

AUCCUCUCAG AUGGA 15

( 2 ) INFORMATION FOR SEQ ID NO:626:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:626:

GAGACAUCGG GGUGG 15

( 2 ) INFORMATION FOR SEQ ID NO:627:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:627:

UGGACAUUUC CGUGA 15

( 2 ) INFORMATION FOR SEQ ID NO:628:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:628:

GGACAUUUCC GUGAC 15

( 2 ) INFORMATION FOR SEQ ID NO:629:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:629:

GACAUUUCCG UGACG 15

( 2 ) INFORMATION FOR SEQ ID NO:630:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:630:

GACAUUUCCG UGACG 15

( 2 ) INFORMATION FOR SEQ ID NO:631:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:631:

CCCCUGUCAU CACAG 15

( 2 ) INFORMATION FOR SEQ ID NO:632:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:632:

CUGUCAUCAC AGCCA 15

( 2 ) INFORMATION FOR SEQ ID NO:633:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:633:

CUGUCAUCAC AGCCA 15

( 2 ) INFORMATION FOR SEQ ID NO:634:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:634:

GCCACCUACC UGGAG 15

( 2 ) INFORMATION FOR SEQ ID NO:635:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:635:

GCCACCUACC UGGAG 15

( 2 ) INFORMATION FOR SEQ ID NO:636:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:636:

CUGGAGUCCC AUCAC 15

( 2 ) INFORMATION FOR SEQ ID NO:637:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:637:

CUGGAGUCCC AUCAC　　　　　　　　　　　　　　　　　　　15

( 2 ) INFORMATION FOR SEQ ID NO:638:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:638:

GUCCCAUCAC AAGGG　　　　　　　　　　　　　　　　　　　15

( 2 ) INFORMATION FOR SEQ ID NO:639:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:639:

CAAGGGUCAC UUCAC　　　　　　　　　　　　　　　　　　　15

( 2 ) INFORMATION FOR SEQ ID NO:640:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:640:

GGUCACUUCA CGCAC　　　　　　　　　　　　　　　　　　　15

( 2 ) INFORMATION FOR SEQ ID NO:641:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:641:

GUCACUUCAC GCACA　　　　　　　　　　　　　　　　　　　15

( 2 ) INFORMATION FOR SEQ ID NO:642:

( i ) SEQUENCE CHARACTERISTICS:
　　　　( A ) LENGTH: 15 base pairs
　　　　( B ) TYPE: nucleic acid
　　　　( C ) STRANDEDNESS: single
　　　　( D ) TOPOLOGY: linear ( x i ) SEQUENCE DESCRIPTION: SEQ ID NO:642:

AGAACGUCUC CGAGG　　　　　　　　　　　　　　　　　　　15

( 2 ) INFORMATION FOR SEQ ID NO:643:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:643:

AACGUCUCCG AGGCC 15

( 2 ) INFORMATION FOR SEQ ID NO:644:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:644:

GAGGCCUUCC CCCUC 15

( 2 ) INFORMATION FOR SEQ ID NO:645:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:645:

AGGCCUUCCC CCUCC 15

( 2 ) INFORMATION FOR SEQ ID NO:646:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:646:

UCCCCCUCCG CGCCU 15

( 2 ) INFORMATION FOR SEQ ID NO:647:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:647:

CGCGCCUUCC CGCCC 15

( 2 ) INFORMATION FOR SEQ ID NO:648:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:648:

CGCGCCUUCC CGCCC 15

( 2 ) INFORMATION FOR SEQ ID NO:649:

( i ) SEQUENCE CHARACTERISTICS:

(A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:649:

GCGCCUUCCC GCCCG                15

(2) INFORMATION FOR SEQ ID NO:650:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:650:

GGGGACUCCC GCAUG                15

(2) INFORMATION FOR SEQ ID NO:651:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:651:

AUGCUCUACU UCUGG                15

(2) INFORMATION FOR SEQ ID NO:652:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:652:

CUCUACUUCU GGUUC                15

(2) INFORMATION FOR SEQ ID NO:653:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:653:

UCUACUUCUG GUUCU                15

(2) INFORMATION FOR SEQ ID NO:654:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (xi) SEQUENCE DESCRIPTION: SEQ ID NO:654:

UUCUGGUUCU CCGAU                15

(2) INFORMATION FOR SEQ ID NO:655:

(i) SEQUENCE CHARACTERISTICS:
            (A) LENGTH: 15 base pairs
            (B) TYPE: nucleic acid 5,705,388

257

258

-continued ( C ) STRANDEDNESS: single
    ( D ) TOPOLOGY: linear ( x i ) SEQUENCE DESCRIPTION: SEQ ID NO:655:

UCUGGUUCUC CGAUC 15

( 2 ) INFORMATION FOR SEQ ID NO:656:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:656:

UGGUUCUCCG AUCAA 15

( 2 ) INFORMATION FOR SEQ ID NO:657:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:657:

CUCCGAUCAA GUGCU 15

( 2 ) INFORMATION FOR SEQ ID NO:658:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:658:

CUCAACUCCC UGGCC 15

( 2 ) INFORMATION FOR SEQ ID NO:659:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:659:

GCCGCCUUCC AGGAG 15

( 2 ) INFORMATION FOR SEQ ID NO:660:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:660:

GCCGCCUUCC AGGAG 15

( 2 ) INFORMATION FOR SEQ ID NO:661:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:661:

CCGCCUUCCA GGAGG    15

( 2 ) INFORMATION FOR SEQ ID NO:662:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:662:

CCGCCUUCCA GGAGG    15

( 2 ) INFORMATION FOR SEQ ID NO:663:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:663:

GCCGUCUCGU GCUCA    15

( 2 ) INFORMATION FOR SEQ ID NO:664:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:664:

GCCGUCUCGU GCUCA    15

( 2 ) INFORMATION FOR SEQ ID NO:665:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:665:

UCGUGCUCAG CCUGA    15

( 2 ) INFORMATION FOR SEQ ID NO:666:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:666:

GAUGAGUUCA AGAAA    15

( 2 ) INFORMATION FOR SEQ ID NO:667:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:667:

AUGAGUUCAA GAAAG    15

( 2 ) INFORMATION FOR SEQ ID NO:668:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:668:

CAGGGUUUCG ACACC    15

( 2 ) INFORMATION FOR SEQ ID NO:669:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:669:

AGGGUUUCGA CACCA    15

( 2 ) INFORMATION FOR SEQ ID NO:670:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:670:

AGGAAAUCUU CCAGG    15

( 2 ) INFORMATION FOR SEQ ID NO:671:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:671:

GAAAUCUUCC AGGAG    15

( 2 ) INFORMATION FOR SEQ ID NO:672:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:672:

GAAAUCUUCC AGGAG    15

( 2 ) INFORMATION FOR SEQ ID NO:673:

( i ) SEQUENCE CHARACTERISTICS:
       ( A ) LENGTH: 15 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:673:

AAAUCUUCCA GGAGC    15

( 2 ) INFORMATION FOR SEQ ID NO:674:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:674:

AGGAGCUUUC CAGAG      15

( 2 ) INFORMATION FOR SEQ ID NO:675:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:675:

GGAGCUUUCC AGAGG      15

( 2 ) INFORMATION FOR SEQ ID NO:676:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:676:

CCCAGGUAGC CGUCC      15

( 2 ) INFORMATION FOR SEQ ID NO:677:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:677:

CCCAGGUAGC CGUCC      15

( 2 ) INFORMATION FOR SEQ ID NO:678:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:678:

UAGCCGUCCA CUGCC      15

( 2 ) INFORMATION FOR SEQ ID NO:679:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:679:

ACUGCCUUAA GGUGC      15

( 2 ) INFORMATION FOR SEQ ID NO:680:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:680:

CUGCCUUAAG GUGCC     15

( 2 ) INFORMATION FOR SEQ ID NO:681:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:681:

CCAAGAUCUC CUGCC     15

( 2 ) INFORMATION FOR SEQ ID NO:682:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:682:

AAGAUCUCCU GCCAG     15

( 2 ) INFORMATION FOR SEQ ID NO:683:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:683:

GGGGUGUCGU GGUGU     15

( 2 ) INFORMATION FOR SEQ ID NO:684:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:684:

GUGGUGUCUU CUUCC     15

( 2 ) INFORMATION FOR SEQ ID NO:685:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:685:

GGUGUCUUCU UCCGU     15

( 2 ) INFORMATION FOR SEQ ID NO:686:

(i) SEQUENCE CHARACTERISTICS:
   (A) LENGTH: 15 base pairs
   (B) TYPE: nucleic acid
   (C) STRANDEDNESS: single
   (D) TOPOLOGY: linear (xi) SEQUENCE DESCRIPTION: SEQ ID NO:686:

GGUGUCUUCU UCCGU  15

(2) INFORMATION FOR SEQ ID NO:687:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:687:

UCUUCUUCCG UCGCC  15

(2) INFORMATION FOR SEQ ID NO:688:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:688:

GUGACGUUCC GCUUC  15

(2) INFORMATION FOR SEQ ID NO:689:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:689:

GUGACGUUCC GCUUC  15

(2) INFORMATION FOR SEQ ID NO:690:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:690:

UGACGUUCCG CUUCC  15

(2) INFORMATION FOR SEQ ID NO:691:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (xi) SEQUENCE DESCRIPTION: SEQ ID NO:691:

UUCCGCUUCC CCCGC  15

(2) INFORMATION FOR SEQ ID NO:692:

(i) SEQUENCE CHARACTERISTICS:
      (A) LENGTH: 15 base pairs ( B ) TYPE: nucleic acid
            ( C ) STRANDEDNESS: single
            ( D ) TOPOLOGY: linear ( x i ) SEQUENCE DESCRIPTION: SEQ ID NO:692:

UCCGCUUCCC CCGCC        15

( 2 ) INFORMATION FOR SEQ ID NO:693:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:693:

GUGGCCUACA GGUUU        15

( 2 ) INFORMATION FOR SEQ ID NO:694:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:694:

UACAGGUUUG AGGAG        15

( 2 ) INFORMATION FOR SEQ ID NO:695:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:695:

ACAGGUUUGA GGAGG        15

( 2 ) INFORMATION FOR SEQ ID NO:696:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:696:

GGAGGAUAUC AUCAC        15

( 2 ) INFORMATION FOR SEQ ID NO:697:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:697:

AGGAUAUCAU CACCA        15

( 2 ) INFORMATION FOR SEQ ID NO:698:

( i ) SEQUENCE CHARACTERISTICS:
            ( A ) LENGTH: 15 base pairs
            ( B ) TYPE: nucleic acid
            ( C ) STRANDEDNESS: single ( D ) TOPOLOGY: linear ( x i ) SEQUENCE DESCRIPTION: SEQ ID NO:698:

AUAUCAUCAC CACCG    15

( 2 ) INFORMATION FOR SEQ ID NO:699:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:699:

CCACCGUCCA GGCCU    15

( 2 ) INFORMATION FOR SEQ ID NO:700:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:700:

CCACCGUCCA GGCCU    15

( 2 ) INFORMATION FOR SEQ ID NO:701:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:701:

CCACCGUCCA GGCCU    15

( 2 ) INFORMATION FOR SEQ ID NO:702:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:702:

CAGGCCUCCU ACUCC    15

( 2 ) INFORMATION FOR SEQ ID NO:703:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:703:

CAGGCCUCCU ACUCC    15

( 2 ) INFORMATION FOR SEQ ID NO:704:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:704:

GCCUCCUACU CCCAG 15

( 2 ) INFORMATION FOR SEQ ID NO:705:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:705:

UCCUACUCCC AGAAA 15

( 2 ) INFORMATION FOR SEQ ID NO:706:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:706:

AAAAGCUCUU CCUAC 15

( 2 ) INFORMATION FOR SEQ ID NO:707:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:707:

AAAAGCUCUU CCUAC 15

( 2 ) INFORMATION FOR SEQ ID NO:708:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:708:

AAGCUCUUCC UACAC 15

( 2 ) INFORMATION FOR SEQ ID NO:709:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:709:

AGCUCUUCCU ACACC 15

( 2 ) INFORMATION FOR SEQ ID NO:710:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:710:

UCUUCCUACA CCUCU 15

(2) INFORMATION FOR SEQ ID NO:711:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:711:

UACACCUCUU GGAUU 15

(2) INFORMATION FOR SEQ ID NO:712:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:712:

CACCUCUUGG AUUUC 15

(2) INFORMATION FOR SEQ ID NO:713:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:713:

CUUGGAUUUC CAGUG 15

(2) INFORMATION FOR SEQ ID NO:714:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:714:

CUUGGAUUUC CAGUG 15

(2) INFORMATION FOR SEQ ID NO:715:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:715:

UUGGAUUUCC AGUGC 15

(2) INFORMATION FOR SEQ ID NO:716:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:716:

UUGGAUUUCC AGUGC 15

( 2 ) INFORMATION FOR SEQ ID NO:717:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:717:

AGGCUGUUUC CAACC     15

( 2 ) INFORMATION FOR SEQ ID NO:718:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:718:

GGCUGUUUCC AACCU     15

( 2 ) INFORMATION FOR SEQ ID NO:719:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:719:

GCUGUUUCCA ACCUG     15

( 2 ) INFORMATION FOR SEQ ID NO:720:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:720:

GCUGUUUCCA ACCUG     15

( 2 ) INFORMATION FOR SEQ ID NO:721:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:721:

GCUGUUUCCA ACCUG     15

( 2 ) INFORMATION FOR SEQ ID NO:722:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:722:

AGCCGCUCCG AGUCC     15

( 2 ) INFORMATION FOR SEQ ID NO:723:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:723:

UCCGAGUCCC UGCAG                                                        15

( 2 ) INFORMATION FOR SEQ ID NO:724:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:724:

CAGAGCUCUC UCCGC                                                        15

( 2 ) INFORMATION FOR SEQ ID NO:725:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:725:

GCUCUCUCCG CUCCC                                                        15

( 2 ) INFORMATION FOR SEQ ID NO:726:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:726:

CCCUGAUCGC CACGG                                                        15

( 2 ) INFORMATION FOR SEQ ID NO:727:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:727:

UGGGCAUCCC GGAGG                                                        15

( 2 ) INFORMATION FOR SEQ ID NO:728:

( i ) SEQUENCE CHARACTERISTICS:
   ( A ) LENGTH: 15 base pairs
   ( B ) TYPE: nucleic acid
   ( C ) STRANDEDNESS: single
   ( D ) TOPOLOGY: linear ( x i ) SEQUENCE DESCRIPTION: SEQ ID NO:728:

CGGAGGUCAU GUCUC                                                        15

( 2 ) INFORMATION FOR SEQ ID NO:729:

( i ) SEQUENCE CHARACTERISTICS:

(A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:729:

GUCAUGUCUC GGCUC                                                                15

(2) INFORMATION FOR SEQ ID NO:730:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:730:

CAUGUCUCGG CUCGA                                                                15

(2) INFORMATION FOR SEQ ID NO:731:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:731:

CUCGGCUCGA GGUGG                                                                15

(2) INFORMATION FOR SEQ ID NO:732:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:732:

GUGGCGUUCA CAGCC                                                                15

(2) INFORMATION FOR SEQ ID NO:733:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:733:

GUGGCGUUCA CAGCC                                                                15

(2) INFORMATION FOR SEQ ID NO:734:

(i) SEQUENCE CHARACTERISTICS:
                (A) LENGTH: 15 base pairs
                (B) TYPE: nucleic acid
                (C) STRANDEDNESS: single
                (D) TOPOLOGY: linear (xi) SEQUENCE DESCRIPTION: SEQ ID NO:734:

UGGCGUUCAC AGCCC                                                                15

(2) INFORMATION FOR SEQ ID NO:735:

(i) SEQUENCE CHARACTERISTICS:
                (A) LENGTH: 15 base pairs
                (B) TYPE: nucleic acid (C) STRANDEDNESS: single
        (D) TOPOLOGY: linear (xi) SEQUENCE DESCRIPTION: SEQ ID NO:735:

UGGCGUUCAC AGCCC                                                                15

(2) INFORMATION FOR SEQ ID NO:736:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:736:

CAGCCCUCAU GAACA                                                                15

(2) INFORMATION FOR SEQ ID NO:737:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:737:

UGGACCUCUU CGAAA                                                                15

(2) INFORMATION FOR SEQ ID NO:738:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:738:

GACCUCUUCG AAAUC                                                                15

(2) INFORMATION FOR SEQ ID NO:739:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:739:

ACCUCUUCGA AAUCA                                                                15

(2) INFORMATION FOR SEQ ID NO:740:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:740:

UCGAAAUCAU CAACC                                                                15

(2) INFORMATION FOR SEQ ID NO:741:

(i) SEQUENCE CHARACTERISTICS:
        (A) LENGTH: 15 base pairs
        (B) TYPE: nucleic acid
        (C) STRANDEDNESS: single
        (D) TOPOLOGY: linear ( x i ) SEQUENCE DESCRIPTION: SEQ ID NO:741:

AAAUCAUCAA CCCCG                                                                                          15

( 2 ) INFORMATION FOR SEQ ID NO:742:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:742:

CCGAGAUUAU CACUC                                                                                          15

( 2 ) INFORMATION FOR SEQ ID NO:743:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:743:

CGAGAUUAUC ACUCU                                                                                          15

( 2 ) INFORMATION FOR SEQ ID NO:744:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:744:

CGAGAUUAUC ACUCU                                                                                          15

( 2 ) INFORMATION FOR SEQ ID NO:745:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:745:

AGAUUAUCAC UCUCG                                                                                          15

( 2 ) INFORMATION FOR SEQ ID NO:746:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:746:

UAUCACUCUC GAUGG                                                                                          15

( 2 ) INFORMATION FOR SEQ ID NO:747:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:747:

AUGGACUUCG GUUUU                                                                15

(2) INFORMATION FOR SEQ ID NO:748:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:748:

UGGACUUCGG UUUUC                                                                15

(2) INFORMATION FOR SEQ ID NO:749:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:749:

UUCGGUUUUC CCAAG                                                                15

(2) INFORMATION FOR SEQ ID NO:750:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:750:

UCGGUUUUCC CAAGC                                                                15

(2) INFORMATION FOR SEQ ID NO:751:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:751:

GGUGGAUUUC CUGCA                                                                15

(2) INFORMATION FOR SEQ ID NO:752:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:752:

GGUGGAUUUC CUGCA                                                                15

(2) INFORMATION FOR SEQ ID NO:753:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:753:

GUGGAUUUCC UGCAG                                                                15

( 2 ) INFORMATION FOR SEQ ID NO:754:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:754:

UGGAUUUCCU GCAGA     15

( 2 ) INFORMATION FOR SEQ ID NO:755:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:755:

GACGUCUCCG CCCAU     15

( 2 ) INFORMATION FOR SEQ ID NO:756:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:756:

GACGUCUCCG CCCAU     15

( 2 ) INFORMATION FOR SEQ ID NO:757:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:757:

UGGAGGUCAG GGAGU     15

( 2 ) INFORMATION FOR SEQ ID NO:758:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:758:

GAUGGCUCCC AACUC     15

( 2 ) INFORMATION FOR SEQ ID NO:759:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:759:

GAUGGCUCCC AACUC     15

( 2 ) INFORMATION FOR SEQ ID NO:760:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:760:

CCCAACUCCU UCUGU  15

( 2 ) INFORMATION FOR SEQ ID NO:761:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:761:

CUUCUGUCCU GAAGA  15

( 2 ) INFORMATION FOR SEQ ID NO:762:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:762:

CUUCUGUCCU GAAGA  15

( 2 ) INFORMATION FOR SEQ ID NO:763:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:763:

CUUCUGUCCU GAAGA  15

( 2 ) INFORMATION FOR SEQ ID NO:764:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:764:

GCAGCAUACC CUGGG  15

( 2 ) INFORMATION FOR SEQ ID NO:765:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:765:

UCCGGAUCCC AGCUG  15

( 2 ) INFORMATION FOR SEQ ID NO:766:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:766:

CCUGGCUUUA GCCUG      15

( 2 ) INFORMATION FOR SEQ ID NO:767:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:767:

CUGGCUUUAG CCUGC      15

( 2 ) INFORMATION FOR SEQ ID NO:768:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:768:

GCUAAAUCUC UCUGG      15

( 2 ) INFORMATION FOR SEQ ID NO:769:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:769:

UAAAUCUCUC UGGCU      15

( 2 ) INFORMATION FOR SEQ ID NO:770:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:770:

UAAAUCUCUC UGGCU      15

( 2 ) INFORMATION FOR SEQ ID NO:771:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:771:

UGGCUGUCUC UCUCU      15

( 2 ) INFORMATION FOR SEQ ID NO:772:

( i ) SEQUENCE CHARACTERISTICS:
    ( A ) LENGTH: 15 base pairs ( B ) TYPE: nucleic acid
                    ( C ) STRANDEDNESS: single
                    ( D ) TOPOLOGY: linear ( x i ) SEQUENCE DESCRIPTION: SEQ ID NO:772:

CUCAAGUAAA CGAAU                                                                15

( 2 ) INFORMATION FOR SEQ ID NO:773:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:773:

CUCGUAGCUG AUGAGGCCGA AAGGCCGAAA GGCGCC                                         36

( 2 ) INFORMATION FOR SEQ ID NO:774:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:774:

AGCCUCGCUG AUGAGGCCGA AAGGCCGAAA GGAGGC                                         36

( 2 ) INFORMATION FOR SEQ ID NO:775:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:775:

AGCCUCGCUG AUGAGGCCGA AAGGCCGAAA GGAGGC                                         36

( 2 ) INFORMATION FOR SEQ ID NO:776:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:776:

GACACACCUG AUGAGGCCGA AAGGCCGAAA UGCCAG                                         36

( 2 ) INFORMATION FOR SEQ ID NO:777:

( i ) SEQUENCE CHARACTERISTICS:
                    ( A ) LENGTH: 36 base pairs
                    ( B ) TYPE: nucleic acid
                    ( C ) STRANDEDNESS: single
                    ( D ) TOPOLOGY: linear ( x i ) SEQUENCE DESCRIPTION: SEQ ID NO:777:

GUGAUGCCUG AUGAGGCCGA AAGGCCGAAA CACACG                                         36

( 2 ) INFORMATION FOR SEQ ID NO:778:

( i ) SEQUENCE CHARACTERISTICS:
                    ( A ) LENGTH: 36 base pairs
                    ( B ) TYPE: nucleic acid
                    ( C ) STRANDEDNESS: single ( D ) TOPOLOGY: linear ( x i ) SEQUENCE DESCRIPTION: SEQ ID NO:778:

GUGAUGCCUG AUGAGGCCGA AAGGCCGAAA CACACG    36

( 2 ) INFORMATION FOR SEQ ID NO:779:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:779:

GCUUGGUCUG AUGAGGCCGA AAGGCCGAAA UGCGAC    36

( 2 ) INFORMATION FOR SEQ ID NO:780:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:780:

ACACCAACUG AUGAGGCCGA AAGGCCGAAA GGGCGG    36

( 2 ) INFORMATION FOR SEQ ID NO:781:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:781:

UUGGUUCCUG AUGAGGCCGA AAGGCCGAAA CACCAA    36

( 2 ) INFORMATION FOR SEQ ID NO:782:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:782:

CCGUCUGCUG AUGAGGCCGA AAGGCCGAAA CCACCU    36

( 2 ) INFORMATION FOR SEQ ID NO:783:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:783:

CCGUCUGCUG AUGAGGCCGA AAGGCCGAAA CCACCU    36

( 2 ) INFORMATION FOR SEQ ID NO:784:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear (x i) SEQUENCE DESCRIPTION: SEQ ID NO:784:

CCGUCUGCUG AUGAGGCCGA AAGGCGAAA CCACCU 36

(2) INFORMATION FOR SEQ ID NO:785:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:785:

GCGCUGGCUG AUGAGGCCGA AAGGCCGAAA GGCCGU 36

(2) INFORMATION FOR SEQ ID NO:786:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:786:

CGCGCUGCUG AUGAGGCCGA AAGGCCGAAA AGGCCG 36

(2) INFORMATION FOR SEQ ID NO:787:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:787:

GUCCGGACUG AUGAGGCCGA AAGGCCGAAA GCCGGC 36

(2) INFORMATION FOR SEQ ID NO:788:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:788:

CGCCGCUCUG AUGAGGCCGA AAGGCCGAAA CGUCCG 36

(2) INFORMATION FOR SEQ ID NO:789:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:789:

CGCCGCUCUG AUGAGGCCGA AAGGCCGAAA CGUCCG 36

(2) INFORMATION FOR SEQ ID NO:790:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (x i) SEQUENCE DESCRIPTION: SEQ ID NO:790:

CGCCGCUCUG AUGAGGCCGA AAGGCCGAAA CGUCCG                   36

( 2 ) INFORMATION FOR SEQ ID NO:791:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:791:

GGCCGAGCUG AUGAGGCCGA AAGGCCGAAA GCAUCA                   36

( 2 ) INFORMATION FOR SEQ ID NO:792:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:792:

CCCGGCCCUG AUGAGGCCGA AAGGCCGAAA GGAGCA                   36

( 2 ) INFORMATION FOR SEQ ID NO:793:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:793:

CGUACUUCUG AUGAGGCCGA AAGGCCGAAA CCCGGC                   36

( 2 ) INFORMATION FOR SEQ ID NO:794:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:794:

CGUACUUCUG AUGAGGCCGA AAGGCCGAAA CCCGGC                   36

( 2 ) INFORMATION FOR SEQ ID NO:795:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:795:

CAGCCCGCUG AUGAGGCCGA AAGGCCGAAA CUUGAC                   36

( 2 ) INFORMATION FOR SEQ ID NO:796:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:796:

UGAUCUGCUG AUGAGGCCGA AAGGCCGAAA GGUUGU                   36

( 2 ) INFORMATION FOR SEQ ID NO:797:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:797:

UGAUCUGCUG AUGAGGCCGA AAGGCCGAAA GGUUGU    36

( 2 ) INFORMATION FOR SEQ ID NO:798:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:798:

GGUGGCUCUG AUGAGGCCGA AAGGCCGAAA UCUGGA    36

( 2 ) INFORMATION FOR SEQ ID NO:799:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:799:

GGCGAUGCUG AUGAGGCCGA AAGGCCGAAA CAGGUG    36

( 2 ) INFORMATION FOR SEQ ID NO:800:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:800:

UGCUGGCCUG AUGAGGCCGA AAGGCCGAAA UGGACA    36

( 2 ) INFORMATION FOR SEQ ID NO:801:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:801:

CGACGUCCUG AUGAGGCCGA AAGGCCGAAA UGGUCU    36

( 2 ) INFORMATION FOR SEQ ID NO:802:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:802:

GGAUGGCCUG AUGAGGCCGA AAGGCCGAAA CGUCGA    36

( 2 ) INFORMATION FOR SEQ ID NO:803:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:803:

CGUUCUGCUG AUGAGGCCGA AAGGCCGAAA UGGCGA				36

( 2 ) INFORMATION FOR SEQ ID NO:804:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:804:

CGUUCUGCUG AUGAGGCCGA AAGGCCGAAA UGGCGA				36

( 2 ) INFORMATION FOR SEQ ID NO:805:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:805:

GACCACGCUG AUGAGGCCGA AAGGCCGAAA CACGUU				36

( 2 ) INFORMATION FOR SEQ ID NO:806:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:806:

GACCACGCUG AUGAGGCCGA AAGGCCGAAA CACGUU				36

( 2 ) INFORMATION FOR SEQ ID NO:807:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:807:

CCUUGAACUG AUGAGGCCGA AAGGCCGAAA CCACGG				36

( 2 ) INFORMATION FOR SEQ ID NO:808:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:808:

CCUUGAACUG AUGAGGCCGA AAGGCCGAAA CCACGG				36

( 2 ) INFORMATION FOR SEQ ID NO:809:

( i ) SEQUENCE CHARACTERISTICS:

(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:809:

CCCCUUGCUG AUGAGGCCGA AAGGCCGAAA GACCAC    36

(2) INFORMATION FOR SEQ ID NO:810:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:810:

UCCCCUUCUG AUGAGGCCGA AAGGCCGAAA AGACCA    36

(2) INFORMATION FOR SEQ ID NO:811:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:811:

GUAGCUGCUG AUGAGGCCGA AAGGCCGAAA GUUCAG    36

(2) INFORMATION FOR SEQ ID NO:812:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:812:

GUAGCUGCUG AUGAGGCCGA AAGGCCGAAA GUUCAG    36

(2) INFORMATION FOR SEQ ID NO:813:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:813:

ACUCGUGCUG AUGAGGCCGA AAGGCCGAAA GCUGUA    36

(2) INFORMATION FOR SEQ ID NO:814:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:814:

ACUCGUGCUG AUGAGGCCGA AAGGCCGAAA GCUGUA    36

(2) INFORMATION FOR SEQ ID NO:815:

(i) SEQUENCE CHARACTERISTICS:
(A) LENGTH: 36 base pairs
(B) TYPE: nucleic acid ( C ) STRANDEDNESS: single
( D ) TOPOLOGY: linear ( x i ) SEQUENCE DESCRIPTION: SEQ ID NO:815:

ACUCGUGCUG AUGAGGCCGA AAGGCCGAAA GCUGUA        36

( 2 ) INFORMATION FOR SEQ ID NO:816:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:816:

GAUGCCCUG AUGAGGCCGA AAGGCCGAAA CCCCCA        36

( 2 ) INFORMATION FOR SEQ ID NO:817:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:817:

ACUGAUUCUG AUGAGGCCGA AAGGCCGAAA UGCCCA        36

( 2 ) INFORMATION FOR SEQ ID NO:818:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:818:

ACAGACUCUG AUGAGGCCGA AAGGCCGAAA UUGAUG        36

( 2 ) INFORMATION FOR SEQ ID NO:819:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:819:

ACAGACUCUG AUGAGGCCGA AAGGCCGAAA UUGAUG        36

( 2 ) INFORMATION FOR SEQ ID NO:820:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:820:

GUCGACACUG AUGAGGCCGA AAGGCCGAAA CUGAUU        36

( 2 ) INFORMATION FOR SEQ ID NO:821:

( i ) SEQUENCE CHARACTERISTICS:
      ( A ) LENGTH: 36 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:821:

CGAAGUCCUG AUGAGGCCGA AAGGCCGAAA CAGACU    36

( 2 ) INFORMATION FOR SEQ ID NO:822:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:822:

CGAAGUCCUG AUGAGGCCGA AAGGCCGAAA CAGACU    36

( 2 ) INFORMATION FOR SEQ ID NO:823:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:823:

GAUCUCGCUG AUGAGGCCGA AAGGCCGAAA GUCGAC    36

( 2 ) INFORMATION FOR SEQ ID NO:824:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:824:

CGAUCUCCUG AUGAGGCCGA AAGGCCGAAA AGUCGA    36

( 2 ) INFORMATION FOR SEQ ID NO:825:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:825:

CAGAGUCCUG AUGAGGCCGA AAGGCCGAAA UCUCGA    36

( 2 ) INFORMATION FOR SEQ ID NO:826:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:826:

CAGAGUCCUG AUGAGGCCGA AAGGCCGAAA UCUCGA    36

( 2 ) INFORMATION FOR SEQ ID NO:827:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:827:

CAGAGUCCUG AUGAGGCCGA AAGGCCGAAA UCUCGA                    36

( 2 ) INFORMATION FOR SEQ ID NO:828:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:828:

CAGAGUCCUG AUGAGGCCGA AAGGCCGAAA UCUCGA                    36

( 2 ) INFORMATION FOR SEQ ID NO:829:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:829:

AAUGGCACUG AUGAGGCCGA AAGGCCGAAA GUCGAU                    36

( 2 ) INFORMATION FOR SEQ ID NO:830:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:830:

AAUGGCACUG AUGAGGCCGA AAGGCCGAAA GUCGAU                    36

( 2 ) INFORMATION FOR SEQ ID NO:831:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:831:

AAUGGCACUG AUGAGGCCGA AAGGCCGAAA GUCGAU                    36

( 2 ) INFORMATION FOR SEQ ID NO:832:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:832:

GGAGGUCCUG AUGAGGCCGA AAGGCCGAAA UGGCAG                    36

( 2 ) INFORMATION FOR SEQ ID NO:833:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:833:

UGAUCUGCUG AUGAGGCCGA AAGGCCGAAA GGUCAA                    36

( 2 ) INFORMATION FOR SEQ ID NO:834:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:834:

UGAUCUGCUG AUGAGGCCGA AAGGCCGAAA GGUCAA     36

( 2 ) INFORMATION FOR SEQ ID NO:835:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:835:

UGAUCUGCUG AUGAGGCCGA AAGGCCGAAA GGUCAA     36

( 2 ) INFORMATION FOR SEQ ID NO:836:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:836:

CUGUGUUCUG AUGAGGCCGA AAGGCCGAAA UCUGGA     36

( 2 ) INFORMATION FOR SEQ ID NO:837:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:837:

CUGUGUUCUG AUGAGGCCGA AAGGCCGAAA UCUGGA     36

( 2 ) INFORMATION FOR SEQ ID NO:838:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:838:

CUGUGUUCUG AUGAGGCCGA AAGGCCGAAA UCUGGA     36

( 2 ) INFORMATION FOR SEQ ID NO:839:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:839:

AGCCAGGCUG AUGAGGCCGA AAGGCCGAAA GCAGUC     36

( 2 ) INFORMATION FOR SEQ ID NO:840:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:840:

AGCCAGGCUG AUGAGGCCGA AAGGCCGAAA GCAGUC        36

( 2 ) INFORMATION FOR SEQ ID NO:841:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:841:

UUAUGGACUG AUGAGGCCGA AAGGCCGAAA GCCAGG        36

( 2 ) INFORMATION FOR SEQ ID NO:842:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:842:

UUAUGGACUG AUGAGGCCGA AAGGCCGAAA GCCAGG        36

( 2 ) INFORMATION FOR SEQ ID NO:843:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:843:

UUAUGGACUG AUGAGGCCGA AAGGCCGAAA GCCAGG        36

( 2 ) INFORMATION FOR SEQ ID NO:844:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:844:

UUUAUGGCUG AUGAGGCCGA AAGGCCGAAA AGCCAG        36

( 2 ) INFORMATION FOR SEQ ID NO:845:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:845:

UUUAUGGCUG AUGAGGCCGA AAGGCCGAAA AGCCAG        36

( 2 ) INFORMATION FOR SEQ ID NO:846:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:846:

GUUUAUGCUG AUGAGGCCGA AAGGCCGAAA AAGCCA 36

( 2 ) INFORMATION FOR SEQ ID NO:847:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:847:

GUUUAUGCUG AUGAGGCCGA AAGGCCGAAA AAGCCA 36

( 2 ) INFORMATION FOR SEQ ID NO:848:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:848:

AGCAGUUCUG AUGAGGCCGA AAGGCCGAAA UGGAAA 36

( 2 ) INFORMATION FOR SEQ ID NO:849:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:849:

GGUGCAGCUG AUGAGGCCGA AAGGCCGAAA GCAGUU 36

( 2 ) INFORMATION FOR SEQ ID NO:850:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:850:

CCCCCUGCUG AUGAGGCCGA AAGGCCGAAA GGUGCA 36

( 2 ) INFORMATION FOR SEQ ID NO:851:

( i ) SEQUENCE CHARACTERISTICS:
 ( A ) LENGTH: 36 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:851:

GCUGCUUCUG AUGAGGCCGA AAGGCCGAAA GCCACC 36

( 2 ) INFORMATION FOR SEQ ID NO:852:

( i ) SEQUENCE CHARACTERISTICS:
 ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:852:

GCUGCUUCUG AUGAGGCCGA AAGGCCGAAA GCCACC    36

(2) INFORMATION FOR SEQ ID NO:853:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:853:

GCUGCUUCUG AUGAGGCCGA AAGGCCGAAA GCCACC    36

(2) INFORMATION FOR SEQ ID NO:854:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:854:

GCUGCUUCUG AUGAGGCCGA AAGGCCGAAA GCCACC    36

(2) INFORMATION FOR SEQ ID NO:855:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:855:

GUUUGUGCUG AUGAGGCCGA AAGGCCGAAA GAGCUG    36

(2) INFORMATION FOR SEQ ID NO:856:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:856:

GUUUGUGCUG AUGAGGCCGA AAGGCCGAAA GAGCUG    36

(2) INFORMATION FOR SEQ ID NO:857:

(i) SEQUENCE CHARACTERISTICS:
    (A) LENGTH: 36 base pairs
    (B) TYPE: nucleic acid
    (C) STRANDEDNESS: single
    (D) TOPOLOGY: linear (xi) SEQUENCE DESCRIPTION: SEQ ID NO:857:

AGUUUGUCUG AUGAGGCCGA AAGGCCGAAA AGAGCU    36

(2) INFORMATION FOR SEQ ID NO:858:

(i) SEQUENCE CHARACTERISTICS:
    (A) LENGTH: 36 base pairs
    (B) TYPE: nucleic acid
    (C) STRANDEDNESS: single ( D ) TOPOLOGY: linear ( x i ) SEQUENCE DESCRIPTION: SEQ ID NO:858:

AGUUUGUCUG AUGAGGCCGA AAGGCCGAAA AGAGCU 36

( 2 ) INFORMATION FOR SEQ ID NO:859:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:859:

GGAGAUGCUG AUGAGGCCGA AAGGCCGAAA GUUUGU 36

( 2 ) INFORMATION FOR SEQ ID NO:860:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:860:

AGGAGAUCUG AUGAGGCCGA AAGGCCGAAA AGUUUG 36

( 2 ) INFORMATION FOR SEQ ID NO:861:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:861:

UGAAGGACUG AUGAGGCCGA AAGGCCGAAA UGAAGU 36

( 2 ) INFORMATION FOR SEQ ID NO:862:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:862:

GGUGAAGCUG AUGAGGCCGA AAGGCCGAAA GAUGAA 36

( 2 ) INFORMATION FOR SEQ ID NO:863:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:863:

CAGGGUGCUG AUGAGGCCGA AAGGCCGAAA GGAGAU 36

( 2 ) INFORMATION FOR SEQ ID NO:864:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:864:

CAGGGUGCUG AUGAGGCCGA AAGGCCGAAA GGAGAU     36

( 2 ) INFORMATION FOR SEQ ID NO:865:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:865:

CAGGGUGCUG AUGAGGCCGA AAGGCCGAAA GGAGAU     36

( 2 ) INFORMATION FOR SEQ ID NO:866:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:866:

UCAGGGUCUG AUGAGGCCGA AAGGCCGAAA AGGAGA     36

( 2 ) INFORMATION FOR SEQ ID NO:867:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:867:

GCUUCAGCUG AUGAGGCCGA AAGGCCGAAA UCAGCU     36

( 2 ) INFORMATION FOR SEQ ID NO:868:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:868:

CAUUGCACUG AUGAGGCCGA AAGGCCGAAA CCUGUC     36

( 2 ) INFORMATION FOR SEQ ID NO:869:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:869:

CAUUGCACUG AUGAGGCCGA AAGGCCGAAA CCUGUC     36

( 2 ) INFORMATION FOR SEQ ID NO:870:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:870:

UGGUGUUCUG AUGAGGCCGA AAGGCCGAAA UCUCAU 36

( 2 ) INFORMATION FOR SEQ ID NO:871:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:871:

UGUUGGACUG AUGAGGCCGA AAGGCCGAAA UGGUGU 36

( 2 ) INFORMATION FOR SEQ ID NO:872:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:872:

UGUUGGACUG AUGAGGCCGA AAGGCCGAAA UGGUGU 36

( 2 ) INFORMATION FOR SEQ ID NO:873:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:873:

GAUGUUGCUG AUGAGGCCGA AAGGCCGAAA GAUGGU 36

( 2 ) INFORMATION FOR SEQ ID NO:874:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:874:

CAGCCAUCUG AUGAGGCCGA AAGGCCGAAA UGUUGG 36

( 2 ) INFORMATION FOR SEQ ID NO:875:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:875:

CAGCCAUCUG AUGAGGCCGA AAGGCCGAAA UGUUGG 36

( 2 ) INFORMATION FOR SEQ ID NO:876:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:876:

CUGGACACUG AUGAGGCCGA AAGGCCGAAA GUCAGC 36

( 2 ) INFORMATION FOR SEQ ID NO:877:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:877:

UCUGGACCUG AUGAGGCCGA AAGGCCGAAA AGUCAG    36

( 2 ) INFORMATION FOR SEQ ID NO:878:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:878:

UCGUCUGCUG AUGAGGCCGA AAGGCCGAAA CAAAGU    36

( 2 ) INFORMATION FOR SEQ ID NO:879:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:879:

CUGAGAGCUG AUGAGGCCGA AAGGCCGAAA UGCUGG    36

( 2 ) INFORMATION FOR SEQ ID NO:880:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:880:

CAUCUGACUG AUGAGGCCGA AAGGCCGAAA GGAUGC    36

( 2 ) INFORMATION FOR SEQ ID NO:881:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:881:

UCCAUCUCUG AUGAGGCCGA AAGGCCGAAA GAGGAU    36

( 2 ) INFORMATION FOR SEQ ID NO:882:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:882:

UCCAUCUCUG AUGAGGCCGA AAGGCCGAAA GAGGAU    36

( 2 ) INFORMATION FOR SEQ ID NO:883:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:883:

CCACCCCUG AUGAGGCCGA AAGGCCGAAA UGUCUC     36

( 2 ) INFORMATION FOR SEQ ID NO:884:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:884:

UCACGGACUG AUGAGGCCGA AAGGCCGAAA UGUCCA     36

( 2 ) INFORMATION FOR SEQ ID NO:885:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:885:

GUCACGGCUG AUGAGGCCGA AAGGCCGAAA AUGUCC     36

( 2 ) INFORMATION FOR SEQ ID NO:886:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:886:

CGUCACGCUG AUGAGGCCGA AAGGCCGAAA AAUGUC     36

( 2 ) INFORMATION FOR SEQ ID NO:887:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:887:

CGUCACGCUG AUGAGGCCGA AAGGCCGAAA AAUGUC     36

( 2 ) INFORMATION FOR SEQ ID NO:888:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:888:

CUGUGAUCUG AUGAGGCCGA AAGGCCGAAA CAGGGG     36

( 2 ) INFORMATION FOR SEQ ID NO:889:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:889:

UGGCUGUCUG AUGAGGCCGA AAGGCCGAAA UGACAG        36

(2) INFORMATION FOR SEQ ID NO:890:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:890:

UGGCUGUCUG AUGAGGCCGA AAGGCCGAAA UGACAG        36

(2) INFORMATION FOR SEQ ID NO:891:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:891:

CUCCAGGCUG AUGAGGCCGA AAGGCCGAAA GGUGGC        36

(2) INFORMATION FOR SEQ ID NO:892:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:892:

CUCCAGGCUG AUGAGGCCGA AAGGCCGAAA GGUGGC        36

(2) INFORMATION FOR SEQ ID NO:893:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:893:

GUGAUGGCUG AUGAGGCCGA AAGGCCGAAA CUCCAG        36

(2) INFORMATION FOR SEQ ID NO:894:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:894:

GUGAUGGCUG AUGAGGCCGA AAGGCCGAAA CUCCAG        36

(2) INFORMATION FOR SEQ ID NO:895:

(i) SEQUENCE CHARACTERISTICS:
        (A) LENGTH: 36 base pairs
        (B) TYPE: nucleic acid ( C ) STRANDEDNESS: single
( D ) TOPOLOGY: linear ( x i ) SEQUENCE DESCRIPTION: SEQ ID NO:895:

CCCUUGUCUG AUGAGGCCGA AAGGCCGAAA UGGGAC 36

( 2 ) INFORMATION FOR SEQ ID NO:896:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:896:

GUGAAGUCUG AUGAGGCCGA AAGGCCGAAA CCCUUG 36

( 2 ) INFORMATION FOR SEQ ID NO:897:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:897:

GUGCGUGCUG AUGAGGCCGA AAGGCCGAAA GUGACC 36

( 2 ) INFORMATION FOR SEQ ID NO:898:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:898:

UGUGCGUCUG AUGAGGCCGA AAGGCCGAAA AGUGAC 36

( 2 ) INFORMATION FOR SEQ ID NO:899:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:899:

CCUCGGACUG AUGAGGCCGA AAGGCCGAAA CGUUCU 36

( 2 ) INFORMATION FOR SEQ ID NO:900:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:900:

GGCCUCGCUG AUGAGGCCGA AAGGCCGAAA GACGUU 36

( 2 ) INFORMATION FOR SEQ ID NO:901:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear (xi) SEQUENCE DESCRIPTION: SEQ ID NO:901:

GAGGGGGCUG AUGAGGCCGA AAGGCCGAAA GGCCUC    36

(2) INFORMATION FOR SEQ ID NO:902:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:902:

GGAGGGGCUG AUGAGGCCGA AAGGCCGAAA AGGCCU    36

(2) INFORMATION FOR SEQ ID NO:903:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:903:

AGGCGCGCUG AUGAGGCCGA AAGGCCGAAA GGGGGA    36

(2) INFORMATION FOR SEQ ID NO:904:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:904:

GGGCGGGCUG AUGAGGCCGA AAGGCCGAAA GGCGCG    36

(2) INFORMATION FOR SEQ ID NO:905:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:905:

GGGCGGGCUG AUGAGGCCGA AAGGCCGAAA GGCGCG    36

(2) INFORMATION FOR SEQ ID NO:906:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:906:

CGGGCGGCUG AUGAGGCCGA AAGGCCGAAA AGGCGC    36

(2) INFORMATION FOR SEQ ID NO:907:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:907:

CAUGCGGCUG AUGAGGCCGA AAGGCCGAAA GUCCCC    36

( 2 ) INFORMATION FOR SEQ ID NO:908:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:908:

CCAGAAGCUG AUGAGGCCGA AAGGCCGAAA GAGCAU    36

( 2 ) INFORMATION FOR SEQ ID NO:909:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:909:

GAACCAGCUG AUGAGGCCGA AAGGCCGAAA GUAGAG    36

( 2 ) INFORMATION FOR SEQ ID NO:910:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:910:

AGAACCACUG AUGAGGCCGA AAGGCCGAAA AGUAGA    36

( 2 ) INFORMATION FOR SEQ ID NO:911:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:911:

AUCGGAGCUG AUGAGGCCGA AAGGCCGAAA CCAGAA    36

( 2 ) INFORMATION FOR SEQ ID NO:912:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:912:

GAUCGGACUG AUGAGGCCGA AAGGCCGAAA ACCAGA    36

( 2 ) INFORMATION FOR SEQ ID NO:913:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:913:

UUGAUCGCUG AUGAGGCCGA AAGGCCGAAA GAACCA    36

( 2 ) INFORMATION FOR SEQ ID NO:914:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:914:

AGCACUUCUG AUGAGGCCGA AAGGCCGAAA UCGGAG      36

( 2 ) INFORMATION FOR SEQ ID NO:915:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:915:

GGCCAGGCUG AUGAGGCCGA AAGGCCGAAA GUUGAG      36

( 2 ) INFORMATION FOR SEQ ID NO:916:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:916:

CUCCUGGCUG AUGAGGCCGA AAGGCCGAAA GGCGGC      36

( 2 ) INFORMATION FOR SEQ ID NO:917:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:917:

CUCCUGGCUG AUGAGGCCGA AAGGCCGAAA GGCGGC      36

( 2 ) INFORMATION FOR SEQ ID NO:918:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:918:

CCUCCUGCUG AUGAGGCCGA AAGGCCGAAA AGGCGG      36

( 2 ) INFORMATION FOR SEQ ID NO:919:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:919:

CCUCCUGCUG AUGAGGCCGA AAGGCCGAAA AGGCGG      36

( 2 ) INFORMATION FOR SEQ ID NO:920:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:920:

UGAGCACCUG AUGAGGCCGA AAGGCCGAAA GACGGC  36

( 2 ) INFORMATION FOR SEQ ID NO:921:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:921:

UGAGCACCUG AUGAGGCCGA AAGGCCGAAA GACGGC  36

( 2 ) INFORMATION FOR SEQ ID NO:922:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:922:

UCAGGCUCUG AUGAGGCCGA AAGGCCGAAA GCACGA  36

( 2 ) INFORMATION FOR SEQ ID NO:923:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:923:

UUUCUUGCUG AUGAGGCCGA AAGGCCGAAA CUCAUC  36

( 2 ) INFORMATION FOR SEQ ID NO:924:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:924:

CUUUCUUCUG AUGAGGCCGA AAGGCCGAAA ACUCAU  36

( 2 ) INFORMATION FOR SEQ ID NO:925:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:925:

GGUGUCGCUG AUGAGGCCGA AAGGCCGAAA ACCCUG  36

( 2 ) INFORMATION FOR SEQ ID NO:926:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:926:

UGGUGUCCUG AUGAGGCCGA AAGGCCGAAA AACCCU 36

( 2 ) INFORMATION FOR SEQ ID NO:927:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:927:

CCUGGAACUG AUGAGGCCGA AAGGCCGAAA UUUCCU 36

( 2 ) INFORMATION FOR SEQ ID NO:928:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:928:

CUCCUGGCUG AUGAGGCCGA AAGGCCGAAA GAUUUC 36

( 2 ) INFORMATION FOR SEQ ID NO:929:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:929:

CUCCUGGCUG AUGAGGCCGA AAGGCCGAAA GAUUUC 36

( 2 ) INFORMATION FOR SEQ ID NO:930:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:930:

GCUCCUGCUG AUGAGGCCGA AAGGCCGAAA AGAUUU 36

( 2 ) INFORMATION FOR SEQ ID NO:931:

( i ) SEQUENCE CHARACTERISTICS:
  ( A ) LENGTH: 36 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:931:

CUCUGGACUG AUGAGGCCGA AAGGCCGAAA GCUCCU 36

( 2 ) INFORMATION FOR SEQ ID NO:932:

( i ) SEQUENCE CHARACTERISTICS:
  ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:932:

CCUCUGGCUG AUGAGGCCGA AAGGCCGAAA AGCUCC    36

(2) INFORMATION FOR SEQ ID NO:933:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:933:

GGACGGCCUG AUGAGGCCGA AAGGCCGAAA CCUGGG    36

(2) INFORMATION FOR SEQ ID NO:934:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:934:

GGACGGCCUG AUGAGGCCGA AAGGCCGAAA CCUGGG    36

(2) INFORMATION FOR SEQ ID NO:935:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:935:

GGCAGUGCUG AUGAGGCCGA AAGGCCGAAA CGGCUA    36

(2) INFORMATION FOR SEQ ID NO:936:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:936:

GCACCUUCUG AUGAGGCCGA AAGGCCGAAA GGCAGU    36

(2) INFORMATION FOR SEQ ID NO:937:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:937:

GGCACCUCUG AUGAGGCCGA AAGGCCGAAA AGGCAG    36

(2) INFORMATION FOR SEQ ID NO:938:

(i) SEQUENCE CHARACTERISTICS:
        (A) LENGTH: 36 base pairs
        (B) TYPE: nucleic acid
        (C) STRANDEDNESS: single (D) TOPOLOGY: linear (x i) SEQUENCE DESCRIPTION: SEQ ID NO:938:

GGCAGGACUG AUGAGGCCGA AAGGCCGAAA UCUUGG    36

(2) INFORMATION FOR SEQ ID NO:939:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:939:

CUGGCAGCUG AUGAGGCCGA AAGGCCGAAA GAUCUU    36

(2) INFORMATION FOR SEQ ID NO:940:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:940:

ACACCACCUG AUGAGGCCGA AAGGCCGAAA CACCCC    36

(2) INFORMATION FOR SEQ ID NO:941:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:941:

GGAAGAACUG AUGAGGCCGA AAGGCCGAAA CACCAC    36

(2) INFORMATION FOR SEQ ID NO:942:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:942:

ACGGAAGCUG AUGAGGCCGA AAGGCCGAAA GACACC    36

(2) INFORMATION FOR SEQ ID NO:943:

(i) SEQUENCE CHARACTERISTICS:
      (A) LENGTH: 36 base pairs
      (B) TYPE: nucleic acid
      (C) STRANDEDNESS: single
      (D) TOPOLOGY: linear (x i) SEQUENCE DESCRIPTION: SEQ ID NO:943:

ACGGAAGCUG AUGAGGCCGA AAGGCCGAAA GACACC    36

(2) INFORMATION FOR SEQ ID NO:944:

(i) SEQUENCE CHARACTERISTICS:
      (A) LENGTH: 36 base pairs
      (B) TYPE: nucleic acid
      (C) STRANDEDNESS: single
      (D) TOPOLOGY: linear ( x i ) SEQUENCE DESCRIPTION: SEQ ID NO:944:

GGCGACGCUG AUGAGGCCGA AAGGCCGAAA AGAAGA    36

( 2 ) INFORMATION FOR SEQ ID NO:945:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:945:

GAAGCGGCUG AUGAGGCCGA AAGGCCGAAA CGUCAC    36

( 2 ) INFORMATION FOR SEQ ID NO:946:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:946:

GAAGCGGCUG AUGAGGCCGA AAGGCCGAAA CGUCAC    36

( 2 ) INFORMATION FOR SEQ ID NO:947:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:947:

GGAAGCGCUG AUGAGGCCGA AAGGCCGAAA ACGUCA    36

( 2 ) INFORMATION FOR SEQ ID NO:948:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:948:

GCGGGGGCUG AUGAGGCCGA AAGGCCGAAA GCGGAA    36

( 2 ) INFORMATION FOR SEQ ID NO:949:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:949:

GGCGGGGCUG AUGAGGCCGA AAGGCCGAAA AGCGGA    36

( 2 ) INFORMATION FOR SEQ ID NO:950:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:950:

```
AAACCUGCUG AUGAGGCCGA AAGGCCGAAA GGCCAC                                   36
```

(2) INFORMATION FOR SEQ ID NO:951:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:951:

```
CUCCUCACUG AUGAGGCCGA AAGGCCGAAA CCUGUA                                   36
```

(2) INFORMATION FOR SEQ ID NO:952:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:952:

```
CCUCCUCCUG AUGAGGCCGA AAGGCCGAAA ACCUGU                                   36
```

(2) INFORMATION FOR SEQ ID NO:953:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:953:

```
GUGAUGACUG AUGAGGCCGA AAGGCCGAAA UCCUCC                                   36
```

(2) INFORMATION FOR SEQ ID NO:954:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:954:

```
UGGUGAUCUG AUGAGGCCGA AAGGCCGAAA UAUCCU                                   36
```

(2) INFORMATION FOR SEQ ID NO:955:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:955:

```
CGGUGGUCUG AUGAGGCCGA AAGGCCGAAA UGAUAU                                   36
```

(2) INFORMATION FOR SEQ ID NO:956:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:956:

```
AGGCCUGCUG AUGAGGCCGA AAGGCCGAAA CGGUGG                                   36
```

( 2 ) INFORMATION FOR SEQ ID NO:957:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:957:

AGGCCUGCUG AUGAGGCCGA AAGGCCGAAA CGGUGG      36

( 2 ) INFORMATION FOR SEQ ID NO:958:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:958:

AGGCCUGCUG AUGAGGCCGA AAGGCCGAAA CGGUGG      36

( 2 ) INFORMATION FOR SEQ ID NO:959:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:959:

GGAGUAGCUG AUGAGGCCGA AAGGCCGAAA GGCCUG      36

( 2 ) INFORMATION FOR SEQ ID NO:960:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:960:

GGAGUAGCUG AUGAGGCCGA AAGGCCGAAA GGCCUG      36

( 2 ) INFORMATION FOR SEQ ID NO:961:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:961:

CUGGGAGCUG AUGAGGCCGA AAGGCCGAAA GGAGGC      36

( 2 ) INFORMATION FOR SEQ ID NO:962:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:962:

UUUCUGGCUG AUGAGGCCGA AAGGCCGAAA GUAGGA      36

( 2 ) INFORMATION FOR SEQ ID NO:963:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:963:

GUAGGAACUG AUGAGGCCGA AAGGCCGAAA GCUUUU     36

( 2 ) INFORMATION FOR SEQ ID NO:964:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:964:

GUAGGAACUG AUGAGGCCGA AAGGCCGAAA GCUUUU     36

( 2 ) INFORMATION FOR SEQ ID NO:965:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:965:

GUGUAGGCUG AUGAGGCCGA AAGGCCGAAA GAGCUU     36

( 2 ) INFORMATION FOR SEQ ID NO:966:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:966:

GGUGUAGCUG AUGAGGCCGA AAGGCCGAAA AGAGCU     36

( 2 ) INFORMATION FOR SEQ ID NO:967:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:967:

AGAGGUGCUG AUGAGGCCGA AAGGCCGAAA GGAAGA     36

( 2 ) INFORMATION FOR SEQ ID NO:968:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:968:

AAUCCAACUG AUGAGGCCGA AAGGCCGAAA GGUGUA     36

( 2 ) INFORMATION FOR SEQ ID NO:969:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:969:

GAAAUCCCUG AUGAGGCCGA AAGGCCGAAA GAGGUG    36

(2) INFORMATION FOR SEQ ID NO:970:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:970:

CACUGGACUG AUGAGGCCGA AAGGCCGAAA UCCAAG    36

(2) INFORMATION FOR SEQ ID NO:971:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:971:

CACUGGACUG AUGAGGCCGA AAGGCCGAAA UCCAAG    36

(2) INFORMATION FOR SEQ ID NO:972:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:972:

GCACUGGCUG AUGAGGCCGA AAGGCCGAAA AUCCAA    36

(2) INFORMATION FOR SEQ ID NO:973:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:973:

GCACUGGCUG AUGAGGCCGA AAGGCCGAAA AUCCAA    36

(2) INFORMATION FOR SEQ ID NO:974:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (xi) SEQUENCE DESCRIPTION: SEQ ID NO:974:

GGUUGGACUG AUGAGGCCGA AAGGCCGAAA CAGCCU    36

(2) INFORMATION FOR SEQ ID NO:975:

(i) SEQUENCE CHARACTERISTICS:
        (A) LENGTH: 36 base pairs
        (B) TYPE: nucleic acid ( C ) STRANDEDNESS: single
( D ) TOPOLOGY: linear ( x i ) SEQUENCE DESCRIPTION: SEQ ID NO:975:

AGGUUGGCUG AUGAGGCCGA AAGGCCGAAA ACAGCC 36

( 2 ) INFORMATION FOR SEQ ID NO:976:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:976:

CAGGUUGCUG AUGAGGCCGA AAGGCCGAAA AACAGC 36

( 2 ) INFORMATION FOR SEQ ID NO:977:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:977:

CAGGUUGCUG AUGAGGCCGA AAGGCCGAAA AACAGC 36

( 2 ) INFORMATION FOR SEQ ID NO:978:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:978:

CAGGUUGCUG AUGAGGCCGA AAGGCCGAAA AACAGC 36

( 2 ) INFORMATION FOR SEQ ID NO:979:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:979:

GGACUCGCUG AUGAGGCCGA AAGGCCGAAA GCGGCU 36

( 2 ) INFORMATION FOR SEQ ID NO:980:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:980:

CUGCAGGCUG AUGAGGCCGA AAGGCCGAAA CUCGGA 36

( 2 ) INFORMATION FOR SEQ ID NO:981:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:981:

GCGGAGACUG AUGAGGCCGA AAGGCCGAAA GCUCUG    36

( 2 ) INFORMATION FOR SEQ ID NO:982:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:982:

GGGAGCGCUG AUGAGGCCGA AAGGCCGAAA GAGAGC    36

( 2 ) INFORMATION FOR SEQ ID NO:983:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:983:

CCGUGGCCUG AUGAGGCCGA AAGGCCGAAA UCAGGG    36

( 2 ) INFORMATION FOR SEQ ID NO:984:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:984:

CCUCCGGCUG AUGAGGCCGA AAGGCCGAAA UGCCCA    36

( 2 ) INFORMATION FOR SEQ ID NO:985:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:985:

GAGACAUCUG AUGAGGCCGA AAGGCCGAAA CCUCCG    36

( 2 ) INFORMATION FOR SEQ ID NO:986:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:986:

GAGCCGACUG AUGAGGCCGA AAGGCCGAAA CAUGAC    36

( 2 ) INFORMATION FOR SEQ ID NO:987:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:987:

```
UCGAGCCCUG AUGAGGCCGA AAGGCCGAAA GACAUG                                    36
```

( 2 ) INFORMATION FOR SEQ ID NO:988:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:988:

```
CCACCUCCUG AUGAGGCCGA AAGGCCGAAA GCCGAG                                    36
```

( 2 ) INFORMATION FOR SEQ ID NO:989:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:989:

```
GGCUGUGCUG AUGAGGCCGA AAGGCCGAAA CGCCAC                                    36
```

( 2 ) INFORMATION FOR SEQ ID NO:990:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:990:

```
GGCUGUGCUG AUGAGGCCGA AAGGCCGAAA CGCCAC                                    36
```

( 2 ) INFORMATION FOR SEQ ID NO:991:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:991:

```
GGGCUGUCUG AUGAGGCCGA AAGGCCGAAA ACGCCA                                    36
```

( 2 ) INFORMATION FOR SEQ ID NO:992:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:992:

```
GGGCUGUCUG AUGAGGCCGA AAGGCCGAAA ACGCCA                                    36
```

( 2 ) INFORMATION FOR SEQ ID NO:993:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:993:

```
UGUUCAUCUG AUGAGGCCGA AAGGCCGAAA GGGCUG                                    36
```

( 2 ) INFORMATION FOR SEQ ID NO:994:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:994:

UUUCGAACUG AUGAGGCCGA AAGGCCGAAA GGUCCA     36

( 2 ) INFORMATION FOR SEQ ID NO:995:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:995:

GAUUUCGCUG AUGAGGCCGA AAGGCCGAAA GAGGUC     36

( 2 ) INFORMATION FOR SEQ ID NO:996:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:996:

UGAUUUCCUG AUGAGGCCGA AAGGCCGAAA AGAGGU     36

( 2 ) INFORMATION FOR SEQ ID NO:997:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:997:

GGUUGAUCUG AUGAGGCCGA AAGGCCGAAA UUUCGA     36

( 2 ) INFORMATION FOR SEQ ID NO:998:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:998:

CGGGGUUCUG AUGAGGCCGA AAGGCCGAAA UGAUUU     36

( 2 ) INFORMATION FOR SEQ ID NO:999:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:999:

GAGUGAUCUG AUGAGGCCGA AAGGCCGAAA UCUCGG     36

( 2 ) INFORMATION FOR SEQ ID NO:1000:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1000:

AGAGUGACUG AUGAGGCCGA AAGGCCGAAA AUCUCG     36

( 2 ) INFORMATION FOR SEQ ID NO:1001:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1001:

AGAGUGACUG AUGAGGCCGA AAGGCCGAAA AUCUCG     36

( 2 ) INFORMATION FOR SEQ ID NO:1002:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1002:

CGAGAGUCUG AUGAGGCCGA AAGGCCGAAA UAAUCU     36

( 2 ) INFORMATION FOR SEQ ID NO:1003:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1003:

CCAUCGACUG AUGAGGCCGA AAGGCCGAAA GUGAUA     36

( 2 ) INFORMATION FOR SEQ ID NO:1004:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1004:

AAAACCGCUG AUGAGGCCGA AAGGCCGAAA GUCCAU     36

( 2 ) INFORMATION FOR SEQ ID NO:1005:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1005:

GAAAACCCUG AUGAGGCCGA AAGGCCGAAA AGUCCA     36

( 2 ) INFORMATION FOR SEQ ID NO:1006:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1006:

CUUGGGACUG AUGAGGCCGA AAGGCCGAAA ACCGAA    36

( 2 ) INFORMATION FOR SEQ ID NO:1007:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1007:

GCUUGGGCUG AUGAGGCCGA AAGGCCGAAA AACCGA    36

( 2 ) INFORMATION FOR SEQ ID NO:1008:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1008:

UGCAGGACUG AUGAGGCCGA AAGGCCGAAA UCCACC    36

( 2 ) INFORMATION FOR SEQ ID NO:1009:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1009:

UGCAGGACUG AUGAGGCCGA AAGGCCGAAA UCCACC    36

( 2 ) INFORMATION FOR SEQ ID NO:1010:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1010:

CUGCAGGCUG AUGAGGCCGA AAGGCCGAAA AUCCAC    36

( 2 ) INFORMATION FOR SEQ ID NO:1011:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1011:

UCUGCAGCUG AUGAGGCCGA AAGGCCGAAA AAUCCA    36

( 2 ) INFORMATION FOR SEQ ID NO:1012:

( i ) SEQUENCE CHARACTERISTICS:
        ( A ) LENGTH: 36 base pairs (B) TYPE: nucleic acid
(C) STRANDEDNESS: single
(D) TOPOLOGY: linear (xi) SEQUENCE DESCRIPTION: SEQ ID NO:1012:

AUGGGCGCUG AUGAGGCCGA AAGGCCGAAA GACGUC　　　　　　　　　　36

(2) INFORMATION FOR SEQ ID NO:1013:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1013:

AUGGGCGCUG AUGAGGCCGA AAGGCCGAAA GACGUC　　　　　　　　　　36

(2) INFORMATION FOR SEQ ID NO:1014:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1014:

ACUCCCUCUG AUGAGGCCGA AAGGCCGAAA CCUCCA　　　　　　　　　　36

(2) INFORMATION FOR SEQ ID NO:1015:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1015:

GAGUUGGCUG AUGAGGCCGA AAGGCCGAAA GCCAUC　　　　　　　　　　36

(2) INFORMATION FOR SEQ ID NO:1016:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1016:

GAGUUGGCUG AUGAGGCCGA AAGGCCGAAA GCCAUC　　　　　　　　　　36

(2) INFORMATION FOR SEQ ID NO:1017:

(i) SEQUENCE CHARACTERISTICS:
(A) LENGTH: 36 base pairs
(B) TYPE: nucleic acid
(C) STRANDEDNESS: single
(D) TOPOLOGY: linear (xi) SEQUENCE DESCRIPTION: SEQ ID NO:1017:

ACAGAAGCUG AUGAGGCCGA AAGGCCGAAA GUUGGG　　　　　　　　　　36

(2) INFORMATION FOR SEQ ID NO:1018:

(i) SEQUENCE CHARACTERISTICS:
(A) LENGTH: 36 base pairs
(B) TYPE: nucleic acid
(C) STRANDEDNESS: single ( D ) TOPOLOGY: linear ( x i ) SEQUENCE DESCRIPTION: SEQ ID NO:1018:

UCUUCAGCUG AUGAGGCCGA AAGGCCGAAA CAGAAG                    36

( 2 ) INFORMATION FOR SEQ ID NO:1019:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1019:

UCUUCAGCUG AUGAGGCCGA AAGGCCGAAA CAGAAG                    36

( 2 ) INFORMATION FOR SEQ ID NO:1020:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1020:

UCUUCAGCUG AUGAGGCCGA AAGGCCGAAA CAGAAG                    36

( 2 ) INFORMATION FOR SEQ ID NO:1021:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1021:

CCCAGGGCUG AUGAGGCCGA AAGGCCGAAA UGCUGC                    36

( 2 ) INFORMATION FOR SEQ ID NO:1022:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1022:

CAGCUGGCUG AUGAGGCCGA AAGGCCGAAA UCCGGA                    36

( 2 ) INFORMATION FOR SEQ ID NO:1023:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1023:

CAGGCUACUG AUGAGGCCGA AAGGCCGAAA GCCAGG                    36

( 2 ) INFORMATION FOR SEQ ID NO:1024:

( i ) SEQUENCE CHARACTERISTICS:
         ( A ) LENGTH: 36 base pairs
         ( B ) TYPE: nucleic acid
         ( C ) STRANDEDNESS: single
         ( D ) TOPOLOGY: linear ( x i ) SEQUENCE DESCRIPTION: SEQ ID NO:1024:

GCAGGCUCUG AUGAGGCCGA AAGGCCGAAA AGCCAG 36

( 2 ) INFORMATION FOR SEQ ID NO:1025:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1025:

CCAGAGACUG AUGAGGCCGA AAGGCCGAAA UUUAGC 36

( 2 ) INFORMATION FOR SEQ ID NO:1026:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1026:

AGCCAGACUG AUGAGGCCGA AAGGCCGAAA GAUUUA 36

( 2 ) INFORMATION FOR SEQ ID NO:1027:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1027:

AGCCAGACUG AUGAGGCCGA AAGGCCGAAA GAUUUA 36

( 2 ) INFORMATION FOR SEQ ID NO:1028:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1028:

AGAGAGACUG AUGAGGCCGA AAGGCCGAAA CAGCCA 36

( 2 ) INFORMATION FOR SEQ ID NO:1029:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1029:

AUUCGUUCUG AUGAGGCCGA AAGGCCGAAA CUUGAG 36

( 2 ) INFORMATION FOR SEQ ID NO:1030:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1030:

UUCCGGGCAG AAGGGUCUAC CAGAGAAACA CACGUUGUGG UACAUUACCU GGUA 54

( 2 ) INFORMATION FOR SEQ ID NO:1031:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1031:

CUCUUCCGAG AAGCAGGGAC CAGAGAAACA CACGUUGUGG UACAUUACCU GGUA 54

( 2 ) INFORMATION FOR SEQ ID NO:1032:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1032:

GUGGCCCGAG AAGUUCAGAC CAGAGAAACA CACGUUGUGG UACAUUACCU GGUA 54

( 2 ) INFORMATION FOR SEQ ID NO:1033:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1033:

GGUUAUCAAG AAGUGGUGAC CAGAGAAACA CACGUUGUGG UACAUUACCU GGUA 54

( 2 ) INFORMATION FOR SEQ ID NO:1034:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1034:

AGGGUCAGAG AAGUGGCAAC CAGAGAAACA CACGUUGUGG UACAUUACCU GGUA 54

( 2 ) INFORMATION FOR SEQ ID NO:1035:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1035:

GGGCCAGGAG AAGGACUGAC CAGAGAAACA CACGUUGUGG UACAUUACCU GGUA 54

( 2 ) INFORMATION FOR SEQ ID NO:1036:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1036:

CAUUGCCCAG AAGGGCCAAC CAGAGAAACA CACGUUGUGG UACAUUACCU GGUA 54

( 2 ) INFORMATION FOR SEQ ID NO:1037:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1037:

GCCUUUGGAG AAGGCAUGAC CAGAGAAACA CACGUUGUGG UACAUUACCU GGUA    54

( 2 ) INFORMATION FOR SEQ ID NO:1038:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1038:

ACCAGGAGAG AAGGCUUGAC CAGAGAAACA CACGUUGUGG UACAUUACCU GGUA    54

( 2 ) INFORMATION FOR SEQ ID NO:1039:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1039:

GGAAGGCGAG AAGGAUCAAC CAGAGAAACA CACGUUGUGG UACAUUACCU GGUA    54

( 2 ) INFORMATION FOR SEQ ID NO:1040:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1040:

CGCUGGAAAG AAGUCUGGAC CAGAGAAACA CACGUUGUGG UACAUUACCU GGUA    54

( 2 ) INFORMATION FOR SEQ ID NO:1041:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1041:

AGUGGCUGAG AAGGAUGUAC CAGAGAAACA CACGUUGUGG UACAUUACCU GGUA    54

( 2 ) INFORMATION FOR SEQ ID NO:1042:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1042:

AGCCACCAAG AAGUGGUGAC CAGAGAAACA CACGUUGUGG UACAUUACCU GGUA    54

( 2 ) INFORMATION FOR SEQ ID NO:1043:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1043:

AGUCAAUGAG AAGAUCAAAC CAGAGAAACA CACGUUGUGG UACAUUACCU GGUA      54

( 2 ) INFORMATION FOR SEQ ID NO:1044:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1044:

GUGUGUUGAG AAGGAGGUAC CAGAGAAACA CACGUUGUGG UACAUUACCU GGUA      54

( 2 ) INFORMATION FOR SEQ ID NO:1045:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1045:

CACAGGUCAG AAGUGUGUAC CAGAGAAACA CACGUUGUGG UACAUUACCU GGUA      54

( 2 ) INFORMATION FOR SEQ ID NO:1046:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1046:

AGUCACAGAG AAGCUGUGAC CAGAGAAACA CACGUUGUGG UACAUUACCU GGUA      54

( 2 ) INFORMATION FOR SEQ ID NO:1047:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1047:

GGGCAUCGAG AAGCACUCAC CAGAGAAACA CACGUUGUGG UACAUUACCU GGUA      54

( 2 ) INFORMATION FOR SEQ ID NO:1048:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1048:

UCAGGGGCAG AAGUCCGCAC CAGAGAAACA CACGUUGUGG UACAUUACCU GGUA      54

( 2 ) INFORMATION FOR SEQ ID NO:1049:

( i ) SEQUENCE CHARACTERISTICS:

(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1049:

AGGUAGCAAG AAGGGGCAAC CAGAGAAACA CACGUUGUGG UACAUUACCU GGUA    54

(2) INFORMATION FOR SEQ ID NO:1050:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1050:

UAUGGAAAAG AAGGUAGCAC CAGAGAAACA CACGUUGUGG UACAUUACCU GGUA    54

(2) INFORMATION FOR SEQ ID NO:1051:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1051:

GAUGCAGGAG AAGCUUAUAC CAGAGAAACA CACGUUGUGG UACAUUACCU GGUA    54

(2) INFORMATION FOR SEQ ID NO:1052:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1052:

UUGUGAACAG AAGCUUGAAC CAGAGAAACA CACGUUGUGG UACAUUACCU GGUA    54

(2) INFORMATION FOR SEQ ID NO:1053:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1053:

AAUUUGUGAG AAGCUGCUAC CAGAGAAACA CACGUUGUGG UACAUUACCU GGUA    54

(2) INFORMATION FOR SEQ ID NO:1054:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1054:

CUUUGCAGAG AAGUCCCUAC CAGAGAAACA CACGUUGUGG UACAUUACCU GGUA    54

(2) INFORMATION FOR SEQ ID NO:1055:

(i) SEQUENCE CHARACTERISTICS:
(A) LENGTH: 54 base pairs
(B) TYPE: nucleic acid ( C ) STRANDEDNESS: single
( D ) TOPOLOGY: linear ( x i ) SEQUENCE DESCRIPTION: SEQ ID NO:1055:

UGGACAAAAG AAGCCAUGAC CAGAGAAACA CACGUUGUGG UACAUUACCU GGUA    54

( 2 ) INFORMATION FOR SEQ ID NO:1056:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1056:

AUGUCUCCAG AAGAAGGAC CAGAGAAACA CACGUUGUGG UACAUUACCU GGUA    54

( 2 ) INFORMATION FOR SEQ ID NO:1057:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1057:

AGGUAGGAAG AAGUGAUGAC CAGAGAAACA CACGUUGUGG UACAUUACCU GGUA    54

( 2 ) INFORMATION FOR SEQ ID NO:1058:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1058:

AGUCCCCAG AAGUGUGGAC CAGAGAAACA CACGUUGUGG UACAUUACCU GGUA    54

( 2 ) INFORMATION FOR SEQ ID NO:1059:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1059:

GAGCAUGAAG AAGCCAUCAC CAGAGAAACA CACGUUGUGG UACAUUACCU GGUA    54

( 2 ) INFORMATION FOR SEQ ID NO:1060:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1060:

UCCCAUCAAG AAGAGCAUAC CAGAGAAACA CACGUUGUGG UACAUUACCU GGUA    54

( 2 ) INFORMATION FOR SEQ ID NO:1061:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1061:

CGUCUCCCAG AAGGCUGAAC CAGAGAAACA CACGUUGUGG UACAUUACCU GGUA 54

( 2 ) INFORMATION FOR SEQ ID NO:1062:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1062:

GCUGGGAAG AAGCCGACAC CAGAGAAACA CACGUUGUGG UACAUUACCU GGUA 54

( 2 ) INFORMATION FOR SEQ ID NO:1063:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1063:

AGGCAGUGAG AAGUGACUAC CAGAGAAACA CACGUUGUGG UACAUUACCU GGUA 54

( 2 ) INFORMATION FOR SEQ ID NO:1064:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1064:

CAUCUUGAAG AAGUGGACAC CAGAGAAACA CACGUUGUGG UACAUUACCU GGUA 54

( 2 ) INFORMATION FOR SEQ ID NO:1065:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1065:

UGUUGCUGAG AAGGGCGUAC CAGAGAAACA CACGUUGUGG UACAUUACCU GGUA 54

( 2 ) INFORMATION FOR SEQ ID NO:1066:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1066:

GAGGCCUGAG AAGUAGUCAC CAGAGAAACA CACGUUGUGG UACAUUACCU GGUA 54

( 2 ) INFORMATION FOR SEQ ID NO:1067:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1067:

UUGGUGUAAG AAGGAAAUAC CAGAGAAACA CACGUUGUGG UACAUUACCU GGUA    54

( 2 ) INFORMATION FOR SEQ ID NO:1068:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1068:

AAGUUGGAAG AAGUCUUUAC CAGAGAAACA CACGUUGUGG UACAUUACCU GGUA    54

( 2 ) INFORMATION FOR SEQ ID NO:1069:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1069:

GGACUCGGAG AAGCUCUCAC CAGAGAAACA CACGUUGUGG UACAUUACCU GGUA    54

( 2 ) INFORMATION FOR SEQ ID NO:1070:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1070:

AUGCCCACAG AAGUGAUCAC CAGAGAAACA CACGUUGUGG UACAUUACCU GGUA    54

( 2 ) INFORMATION FOR SEQ ID NO:1071:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1071:

CUACCUCGAG AAGAGACAAC CAGAGAAACA CACGUUGUGG UACAUUACCU GGUA    54

( 2 ) INFORMATION FOR SEQ ID NO:1072:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1072:

UUCAUGAGAG AAGUAAACAC CAGAGAAACA CACGUUGUGG UACAUUACCU GGUA    54

( 2 ) INFORMATION FOR SEQ ID NO:1073:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1073:

UCUGCAGCAG AAGGAAGCAC CAGAGAAACA CACGUUGUGG UACAUUACCU GGUA    54

( 2 ) INFORMATION FOR SEQ ID NO:1074:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1074:

CCAUCUGCAG AAGCAGGAAC CAGAGAAACA CACGUUGUGG UACAUUACCU GGUA    54

( 2 ) INFORMATION FOR SEQ ID NO:1075:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1075:

CAAAGUCCAG AAGCAGCAAC CAGAGAAACA CACGUUGUGG UACAUUACCU GGUA    54

( 2 ) INFORMATION FOR SEQ ID NO:1076:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1076:

AAUCCACCAG AAGGUGCUAC CAGAGAAACA CACGUUGUGG UACAUUACCU GGUA    54

( 2 ) INFORMATION FOR SEQ ID NO:1077:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1077:

AGGGUUCCAG AAGUGAGCAC CAGAGAAACA CACGUUGUGG UACAUUACCU GGUA    54

( 2 ) INFORMATION FOR SEQ ID NO:1078:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1078:

AGACCCUGCU GCCCGGAA    18

( 2 ) INFORMATION FOR SEQ ID NO:1079:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1079:

CCCUGCUGCC CGGAAGAG    18

( 2 ) INFORMATION FOR SEQ ID NO:1080:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1080:

CUGAACGGCU CGGGCCAC    18

( 2 ) INFORMATION FOR SEQ ID NO:1081:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1081:

CACCACUGCC UGAUAACC    18

( 2 ) INFORMATION FOR SEQ ID NO:1082:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1082:

UGCCACAGUC CUGACCCU    18

( 2 ) INFORMATION FOR SEQ ID NO:1083:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1083:

CAGUCCUGAC CCUGGCCC    18

( 2 ) INFORMATION FOR SEQ ID NO:1084:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1084:

UGGCCCUGCU GGGCAAUG    18

( 2 ) INFORMATION FOR SEQ ID NO:1085:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( x i ) SEQUENCE DESCRIPTION: SEQ ID NO:1085:

CAUGCCUGCU CCAAAGGC    18

( 2 ) INFORMATION FOR SEQ ID NO:1086:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1086:

CAAGCCUGCC CUCCUGGU      18

( 2 ) INFORMATION FOR SEQ ID NO:1087:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1087:

UGAUCCAGAC CGCCUUCC      18

( 2 ) INFORMATION FOR SEQ ID NO:1088:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1088:

CCAGACCGCC UUCCAGCG      18

( 2 ) INFORMATION FOR SEQ ID NO:1089:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1089:

ACAUCCAGAU CAGCCACU      18

( 2 ) INFORMATION FOR SEQ ID NO:1090:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1090:

CACCACUGCC UGGUGGCU      18

( 2 ) INFORMATION FOR SEQ ID NO:1091:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1091:

UUGAUCAGUC CAUUGACU      18

( 2 ) INFORMATION FOR SEQ ID NO:1092:

( i ) SEQUENCE CHARACTERISTICS:
    ( A ) LENGTH: 18 base pairs (B) TYPE: nucleic acid
(C) STRANDEDNESS: single
(D) TOPOLOGY: linear (xi) SEQUENCE DESCRIPTION: SEQ ID NO:1092:

ACCUCCAGAU CAACACAC 18

(2) INFORMATION FOR SEQ ID NO:1093:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1093:

ACACACAGCU GACCUGUG 18

(2) INFORMATION FOR SEQ ID NO:1094:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1094:

CACAGCUGAC CUGUGACU 18

(2) INFORMATION FOR SEQ ID NO:1095:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1095:

GAGUGCGGAC CGAUGCCC 18

(2) INFORMATION FOR SEQ ID NO:1096:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1096:

GCGGACCGAU GCCCCUGA 18

(2) INFORMATION FOR SEQ ID NO:1097:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1097:

UGCCCCUGAC UGCUACCU 18

(2) INFORMATION FOR SEQ ID NO:1098:

(i) SEQUENCE CHARACTERISTICS:
(A) LENGTH: 18 base pairs
(B) TYPE: nucleic acid
(C) STRANDEDNESS: single ( D ) TOPOLOGY: linear ( x i ) SEQUENCE DESCRIPTION: SEQ ID NO:1098:

GCUACCUGUC UUUCCAUA					18

( 2 ) INFORMATION FOR SEQ ID NO:1099:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1099:

AUAAGCUGCU CCUGCAUC					18

( 2 ) INFORMATION FOR SEQ ID NO:1100:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1100:

UCAAGCAGCU GUUCACAA					18

( 2 ) INFORMATION FOR SEQ ID NO:1101:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1101:

AGCAGCUGUU CACAAAUU					18

( 2 ) INFORMATION FOR SEQ ID NO:1102:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1102:

AGGGACAGAU CUGCAAAG					18

( 2 ) INFORMATION FOR SEQ ID NO:1103:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1103:

CAUGGCCGAU UUUGUCCA					18

( 2 ) INFORMATION FOR SEQ ID NO:1104:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1104:

CCUUUCAGAU GGAGACAU 18

( 2 ) INFORMATION FOR SEQ ID NO:1105:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1105:

CAUCACAGCC UCCUACCU 18

( 2 ) INFORMATION FOR SEQ ID NO:1106:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1106:

CCACACUGCU GGGGGACU 18

( 2 ) INFORMATION FOR SEQ ID NO:1107:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1107:

GAUGGCCGCC UCAUGCUC 18

( 2 ) INFORMATION FOR SEQ ID NO:1108:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1108:

AUGCUCAGCC UGAUGGGA 18

( 2 ) INFORMATION FOR SEQ ID NO:1109:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1109:

UCAGCCUGAU GGGAGACG 18

( 2 ) INFORMATION FOR SEQ ID NO:1110:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1110:

```
    GUCGGCGGCU UCCCCAGC                                                      18
```

( 2 ) INFORMATION FOR SEQ ID NO:1111:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1111:

```
    AGUCACCGUC CACUGCCU                                                      18
```

( 2 ) INFORMATION FOR SEQ ID NO:1112:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1112:

```
    GUCCACUGCC UCAAGAUG                                                      18
```

( 2 ) INFORMATION FOR SEQ ID NO:1113:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1113:

```
    ACGCCCAGAC CAGCAACA                                                      18
```

( 2 ) INFORMATION FOR SEQ ID NO:1114:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1114:

```
    GACUACCGUC CAGGCCUC                                                      18
```

( 2 ) INFORMATION FOR SEQ ID NO:1115:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1115:

```
    AUUUCCAGAU UACACCAA                                                      18
```

( 2 ) INFORMATION FOR SEQ ID NO:1116:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1116:

```
    AAAGACUGUU UCCAACUU                                                      18
```

(2) INFORMATION FOR SEQ ID NO:1117:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1117:

GAGAGCAGCU CCGAGUCC                    18

(2) INFORMATION FOR SEQ ID NO:1118:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1118:

GAUCACCGCU GUGGGCAU                    18

(2) INFORMATION FOR SEQ ID NO:1119:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1119:

UGUCUCGGCU CGAGGUAG                    18

(2) INFORMATION FOR SEQ ID NO:1120:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1120:

GUUUACAGCC CUCAUGAA                    18

(2) INFORMATION FOR SEQ ID NO:1121:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1121:

GCUUCCUGCU GCUGCAGA                    18

(2) INFORMATION FOR SEQ ID NO:1122:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1122:

UCCUGCUGCU GCAGAUGG                    18

(2) INFORMATION FOR SEQ ID NO:1123:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1123:

UGCUGCAGAU GGACUUUG                                                                              18

( 2 ) INFORMATION FOR SEQ ID NO:1124:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1124:

AGCACCUGCU GGUGGAUU                                                                              18

( 2 ) INFORMATION FOR SEQ ID NO:1125:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1125:

GCUCACAGCU GGAACCCU                                                                              18

( 2 ) INFORMATION FOR SEQ ID NO:1126:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1126:

ACCAAGAGAG AAGGCUUGAC CAGAGAAACA CACGUUGUGG UACAUUACCU GGUA                                       54

( 2 ) INFORMATION FOR SEQ ID NO:1127:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1127:

GGAAGGCCAG AAGGACCAAC CAGAGAAACA CACGUUGUGG UACAUUACCU GGUA                                       54

( 2 ) INFORMATION FOR SEQ ID NO:1128:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1128:

CGCUGGAAAG AAGUCUGGAC CAGAGAAACA CACGUUGUGG UACAUUACCU GGUA                                       54

( 2 ) INFORMATION FOR SEQ ID NO:1129:

( i ) SEQUENCE CHARACTERISTICS:

(A) LENGTH: 54 base pairs
            (B) TYPE: nucleic acid
            (C) STRANDEDNESS: single
            (D) TOPOLOGY: linear (xi) SEQUENCE DESCRIPTION: SEQ ID NO:1129:

CCGCUGACAG AAGGAUAGAC CAGAGAAACA CACGUUGUGG UACAUUACCU GGUA        54

(2) INFORMATION FOR SEQ ID NO:1130:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (xi) SEQUENCE DESCRIPTION: SEQ ID NO:1130:

CUUGACCCAG AAGAGGAGAC CAGAGAAACA CACGUUGUGG UACAUUACCU GGUA        54

(2) INFORMATION FOR SEQ ID NO:1131:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (xi) SEQUENCE DESCRIPTION: SEQ ID NO:1131:

GGUGGCUGAG AAGGAGGUAC CAGAGAAACA CACGUUGUGG UACAUUACCU GGUA        54

(2) INFORMATION FOR SEQ ID NO:1132:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (xi) SEQUENCE DESCRIPTION: SEQ ID NO:1132:

UGGCGAUGAG AAGGUGGCAC CAGAGAAACA CACGUUGUGG UACAUUACCU GGUA        54

(2) INFORMATION FOR SEQ ID NO:1133:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (xi) SEQUENCE DESCRIPTION: SEQ ID NO:1133:

AGUCGACAAG AAGAUUGAAC CAGAGAAACA CACGUUGUGG UACAUUACCU GGUA        54

(2) INFORMATION FOR SEQ ID NO:1134:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (xi) SEQUENCE DESCRIPTION: SEQ ID NO:1134:

UCGAAGUCAG AAGACUGAAC CAGAGAAACA CACGUUGUGG UACAUUACCU GGUA        54

(2) INFORMATION FOR SEQ ID NO:1135:

(i) SEQUENCE CHARACTERISTICS:
            (A) LENGTH: 54 base pairs
            (B) TYPE: nucleic acid (C) STRANDEDNESS: single
(D) TOPOLOGY: linear (xi) SEQUENCE DESCRIPTION: SEQ ID NO:1135:

CUGUGUUGAG AAGGAGGUAC CAGAGAAACA CACGUUGUGG UACAUUACCU GGUA  54

(2) INFORMATION FOR SEQ ID NO:1136:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1136:

CGUCGCAGAG AAGCUCGAC CAGAGAAACA CACGUUGUGG UACAUUACCU GGUA  54

(2) INFORMATION FOR SEQ ID NO:1137:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1137:

AGGUAGCAAG AAGGGGCAAC CAGAGAAACA CACGUUGUGG UACAUUACCU GGUA  54

(2) INFORMATION FOR SEQ ID NO:1138:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1138:

GGUGCAGGAG AAGUUUAUAC CAGAGAAACA CACGUUGUGG UACAUUACCU GGUA  54

(2) INFORMATION FOR SEQ ID NO:1139:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1139:

UUGUGAAGAG AAGCUUGAAC CAGAGAAACA CACGUUGUGG UACAUUACCU GGUA  54

(2) INFORMATION FOR SEQ ID NO:1140:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1140:

GCUUCAGAAG AAGCUUCAAC CAGAGAAACA CACGUUGUGG UACAUUACCU GGUA  54

(2) INFORMATION FOR SEQ ID NO:1141:

(i) SEQUENCE CHARACTERISTICS:
(A) LENGTH: 54 base pairs
(B) TYPE: nucleic acid
(C) STRANDEDNESS: single
(D) TOPOLOGY: linear ( x i ) SEQUENCE DESCRIPTION: SEQ ID NO:1141:

UGGACAAAAG AAGCCAUGAC CAGAGAAACA CACGUUGUGG UACAUUACCU GGUA    54

( 2 ) INFORMATION FOR SEQ ID NO:1142:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1142:

CGGCCCUCAG AAGGACAAAC CAGAGAAACA CACGUUGUGG UACAUUACCU GGUA    54

( 2 ) INFORMATION FOR SEQ ID NO:1143:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1143:

AUGUCUCCAG AAGAGAGGAC CAGAGAAACA CACGUUGUGG UACAUUACCU GGUA    54

( 2 ) INFORMATION FOR SEQ ID NO:1144:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1144:

GAAGACCGAG AAGGAAGGAC CAGAGAAACA CACGUUGUGG UACAUUACCU GGUA    54

( 2 ) INFORMATION FOR SEQ ID NO:1145:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1145:

CCCCAGAAAG AAGGGCGGAC CAGAGAAACA CACGUUGUGG UACAUUACCU GGUA    54

( 2 ) INFORMATION FOR SEQ ID NO:1146:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1146:

AGCACUUGAG AAGAGAACAC CAGAGAAACA CACGUUGUGG UACAUUACCU GGUA    54

( 2 ) INFORMATION FOR SEQ ID NO:1147:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1147:

UCCUGGAAAG AAGCCCUGAC CAGAGAAACA CACGUUGUGG UACAUUACCU GGUA 54

( 2 ) INFORMATION FOR SEQ ID NO:1148:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1148:

GAGCACGAAG AAGCCCUCAC CAGAGAAACA CACGUUGUGG UACAUUACCU GGUA 54

( 2 ) INFORMATION FOR SEQ ID NO:1149:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1149:

CCCUGUCAAG AAGAGCACAC CAGAGAAACA CACGUUGUGG UACAUUACCU GGUA 54

( 2 ) INFORMATION FOR SEQ ID NO:1150:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1150:

AGGCAGUGAG AAGCUACCAC CAGAGAAACA CACGUUGUGG UACAUUACCU GGUA 54

( 2 ) INFORMATION FOR SEQ ID NO:1151:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1151:

CACCUUAAAG AAGUGGACAC CAGAGAAACA CACGUUGUGG UACAUUACCU GGUA 54

( 2 ) INFORMATION FOR SEQ ID NO:1152:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1152:

GUCACGGCAG AAGAAGAAAC CAGAGAAACA CACGUUGUGG UACAUUACCU GGUA 54

( 2 ) INFORMATION FOR SEQ ID NO:1153:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1153:

GCGGGGGAAG AAGAACGUAC CAGAGAAACA CACGUUGUGG UACAUUACCU GGUA 54

( 2 ) INFORMATION FOR SEQ ID NO:1154:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1154:

GCCAUCUGAG AAGGGGAAAC CAGAGAAACA CACGUUGUGG UACAUUACCU GGUA     54

( 2 ) INFORMATION FOR SEQ ID NO:1155:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1155:

UCUCGGCCAG AAGGGCGGAC CAGAGAAACA CACGUUGUGG UACAUUACCU GGUA     54

( 2 ) INFORMATION FOR SEQ ID NO:1156:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1156:

GAGGCCUGAG AAGUGGUGAC CAGAGAAACA CACGUUGUGG UACAUUACCU GGUA     54

( 2 ) INFORMATION FOR SEQ ID NO:1157:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1157:

AUUUGCUGAG AAGCCUGCAC CAGAGAAACA CACGUUGUGG UACAUUACCU GGUA     54

( 2 ) INFORMATION FOR SEQ ID NO:1158:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1158:

AGGUUGGAAG AAGCCUUAAC CAGAGAAACA CACGUUGUGG UACAUUACCU GGUA     54

( 2 ) INFORMATION FOR SEQ ID NO:1159:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1159:

GGCUCUCAAG AAGGUUGGAC CAGAGAAACA CACGUUGUGG UACAUUACCU GGUA     54

( 2 ) INFORMATION FOR SEQ ID NO:1160:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1160:

GGACUCGGAG AAGCUCUCAC CAGAGAAACA CACGUUGUGG UACAUUACCU GGUA    54

( 2 ) INFORMATION FOR SEQ ID NO:1161:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1161:

GAUCAGGGAG AAGAGAGAAC CAGAGAAACA CACGUUGUGG UACAUUACCU GGUA    54

( 2 ) INFORMATION FOR SEQ ID NO:1162:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1162:

CCGUGGCGAG AAGGGAGCAC CAGAGAAACA CACGUUGUGG UACAUUACCU GGUA    54

( 2 ) INFORMATION FOR SEQ ID NO:1163:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1163:

CCACCUCGAG AAGAGACAAC CAGAGAAACA CACGUUGUGG UACAUUACCU GGUA    54

( 2 ) INFORMATION FOR SEQ ID NO:1164:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1164:

UUCAUGAGAG AAGUGAACAC CAGAGAAACA CACGUUGUGG UACAUUACCU GGUA    54

( 2 ) INFORMATION FOR SEQ ID NO:1165:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1165:

CAGCAGCAAG AAGCCAUCAC CAGAGAAACA CACGUUGUGG UACAUUACCU GGUA    54

( 2 ) INFORMATION FOR SEQ ID NO:1166:

( i ) SEQUENCE CHARACTERISTICS:
    ( A ) LENGTH: 54 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1166:

UCUGCAGCAG AAGGCAGCAC CAGAGAAACA CACGUUGUGG UACAUUACCU GGUA          54

( 2 ) INFORMATION FOR SEQ ID NO:1167:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1167:

CCAUCUGCAG AAGCAGGCAC CAGAGAAACA CACGUUGUGG UACAUUACCU GGUA          54

( 2 ) INFORMATION FOR SEQ ID NO:1168:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1168:

CGAAGUCCAG AAGCAGCAAC CAGAGAAACA CACGUUGUGG UACAUUACCU GGUA          54

( 2 ) INFORMATION FOR SEQ ID NO:1169:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1169:

CUUGGGAAAG AAGAAGUCAC CAGAGAAACA CACGUUGUGG UACAUUACCU GGUA          54

( 2 ) INFORMATION FOR SEQ ID NO:1170:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1170:

AAUCCACCAG AAGGUGCUAC CAGAGAAACA CACGUUGUGG UACAUUACCU GGUA          54

( 2 ) INFORMATION FOR SEQ ID NO:1171:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1171:

GCGGAGACAG AAGCGUGUAC CAGAGAAACA CACGUUGUGG UACAUUACCU GGUA          54

( 2 ) INFORMATION FOR SEQ ID NO:1172:

( i ) SEQUENCE CHARACTERISTICS:
        ( A ) LENGTH: 54 base pairs (B) TYPE: nucleic acid
(C) STRANDEDNESS: single
(D) TOPOLOGY: linear (xi) SEQUENCE DESCRIPTION: SEQ ID NO:1172:

CCCCGAUGAG AAGAGACGAC CAGAGAAACA CACGUUGUGG UACAUUACCU GGUA    54

(2) INFORMATION FOR SEQ ID NO:1173:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1173:

GUCUUCAGAG AAGAAGGAAC CAGAGAAACA CACGUUGUGG UACAUUACCU GGUA    54

(2) INFORMATION FOR SEQ ID NO:1174:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1174:

CAGCUGGGAG AAGGAGCAAC CAGAGAAACA CACGUUGUGG UACAUUACCU GGUA    54

(2) INFORMATION FOR SEQ ID NO:1175:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1175:

UAGCAGGCAG AAGGGAUCAC CAGAGAAACA CACGUUGUGG UACAUUACCU GGUA    54

(2) INFORMATION FOR SEQ ID NO:1176:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1176:

CGUUAGCAAG AAGCUGGGAC CAGAGAAACA CACGUUGUGG UACAUUACCU GGUA    54

(2) INFORMATION FOR SEQ ID NO:1177:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO:1177:

ACCAGCACAG AAGCUCCCAC CAGAGAAACA CACGUUGUGG UACAUUACCU GGUA    54

(2) INFORMATION FOR SEQ ID NO:1178:

(i) SEQUENCE CHARACTERISTICS:
(A) LENGTH: 54 base pairs
(B) TYPE: nucleic acid
(C) STRANDEDNESS: single (D) TOPOLOGY: linear (xi) SEQUENCE DESCRIPTION: SEQ ID NO:1178:

GGACCUCAAG AAGGGUCUAC CAGAGAAACA CACGUUGUGG UACAUUACCU GGUA  54

(2) INFORMATION FOR SEQ ID NO:1179:

(i) SEQUENCE CHARACTERISTICS:
       (A) LENGTH: 54 base pairs
       (B) TYPE: nucleic acid
       (C) STRANDEDNESS: single
       (D) TOPOLOGY: linear (xi) SEQUENCE DESCRIPTION: SEQ ID NO:1179:

ACUCACUGAG AAGGCUAAAC CAGAGAAACA CACGUUGUGG UACAUUACCU GGUA  54

(2) INFORMATION FOR SEQ ID NO:1180:

(i) SEQUENCE CHARACTERISTICS:
       (A) LENGTH: 54 base pairs
       (B) TYPE: nucleic acid
       (C) STRANDEDNESS: single
       (D) TOPOLOGY: linear (xi) SEQUENCE DESCRIPTION: SEQ ID NO:1180:

CAGAGAGAAG AAGCCAGAAC CAGAGAAACA CACGUUGUGG UACAUUACCU GGUA  54

(2) INFORMATION FOR SEQ ID NO:1181:

(i) SEQUENCE CHARACTERISTICS:
       (A) LENGTH: 54 base pairs
       (B) TYPE: nucleic acid
       (C) STRANDEDNESS: single
       (D) TOPOLOGY: linear (xi) SEQUENCE DESCRIPTION: SEQ ID NO:1181:

ACUUGAGAAG AAGAGAGAAC CAGAGAAACA CACGUUGUGG UACAUUACCU GGUA  54

(2) INFORMATION FOR SEQ ID NO:1182:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:1182:

CAAGCCCGCC CUCUUGGU  18

(2) INFORMATION FOR SEQ ID NO:1183:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (xi) SEQUENCE DESCRIPTION: SEQ ID NO:1183:

UGGUCCAGAC GGCCUUCC  18

(2) INFORMATION FOR SEQ ID NO:1184:

(i) SEQUENCE CHARACTERISTICS:
       (A) LENGTH: 18 base pairs
       (B) TYPE: nucleic acid
       (C) STRANDEDNESS: single
       (D) TOPOLOGY: linear ( x i ) SEQUENCE DESCRIPTION: SEQ ID NO:1184:

CCAGACGGCC UUCCAGCG   18

( 2 ) INFORMATION FOR SEQ ID NO:1185:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1185:

CUAUCCGGAC GUCAGCGG   18

( 2 ) INFORMATION FOR SEQ ID NO:1186:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1186:

CUCCUCGGCC GGGUCAAG   18

( 2 ) INFORMATION FOR SEQ ID NO:1187:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1187:

ACCUCCAGAU CAGCCACC   18

( 2 ) INFORMATION FOR SEQ ID NO:1188:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1188:

GCCACCUGUC CAUCGCCA   18

( 2 ) INFORMATION FOR SEQ ID NO:1189:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1189:

UCAAUCAGUC UGUCGACU   18

( 2 ) INFORMATION FOR SEQ ID NO:1190:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1190:

UCAGUCUGUC GACUUCGA    18

(2) INFORMATION FOR SEQ ID NO:1191:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1191:

ACCUCCAGAU CAACACAG    18

(2) INFORMATION FOR SEQ ID NO:1192:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1192:

CAGAGCUGAC CUGCGACG    18

(2) INFORMATION FOR SEQ ID NO:1193:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1193:

UGCCCCGAC UGCUACCU    18

(2) INFORMATION FOR SEQ ID NO:1194:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1194:

AUAAACUGCU CCUGCACC    18

(2) INFORMATION FOR SEQ ID NO:1195:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1195:

UCAAGCAGCU CUUCACAA    18

(2) INFORMATION FOR SEQ ID NO:1196:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1196:

UGAAGCUGAU UCUGAAGC    18

( 2 ) INFORMATION FOR SEQ ID NO:1197:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1197:

CAUGGCUGAC UUUGUCCA　　　　　　　　　　　　　　　　　　　　　　　　　　18

( 2 ) INFORMATION FOR SEQ ID NO:1198:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1198:

UUGUCCAGAC GAGGGCCG　　　　　　　　　　　　　　　　　　　　　　　　　　18

( 2 ) INFORMATION FOR SEQ ID NO:1199:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1199:

CCUCUCAGAU GGAGACAU　　　　　　　　　　　　　　　　　　　　　　　　　　18

( 2 ) INFORMATION FOR SEQ ID NO:1200:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1200:

CCUUCCCGCC CGGUCUUC　　　　　　　　　　　　　　　　　　　　　　　　　　18

( 2 ) INFORMATION FOR SEQ ID NO:1201:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1201:

CCGCCCGGUC UUCUGGGG　　　　　　　　　　　　　　　　　　　　　　　　　　18

( 2 ) INFORMATION FOR SEQ ID NO:1202:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1202:

GUUCUCCGAU CAAGUGCU　　　　　　　　　　　　　　　　　　　　　　　　　　18

( 2 ) INFORMATION FOR SEQ ID NO:1203:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:1203:

CAGGGCCGCC UUCCAGGA                                                                    18

( 2 ) INFORMATION FOR SEQ ID NO:1204:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1204:

GAGGGCCGUC UCGUGCUC                                                                    18

( 2 ) INFORMATION FOR SEQ ID NO:1205:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1205:

GUGCUCAGCC UGACAGGG                                                                    18

( 2 ) INFORMATION FOR SEQ ID NO:1206:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1206:

GGUAGCCGUC CACUGCCU                                                                    18

( 2 ) INFORMATION FOR SEQ ID NO:1207:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1207:

GUCCACUGCC UUAAGGUG                                                                    18

( 2 ) INFORMATION FOR SEQ ID NO:1208:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1208:

UUCUUCCGUC GCCGUGAC                                                                    18

( 2 ) INFORMATION FOR SEQ ID NO:1209:

( i ) SEQUENCE CHARACTERISTICS:

(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1209:

ACGUUCCGCU UCCCCCGC 18

(2) INFORMATION FOR SEQ ID NO:1210:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1210:

UUCCCCCGCC CAGAUGGC 18

(2) INFORMATION FOR SEQ ID NO:1211:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1211:

CCGCCCAGAU GGCCGAGA 18

(2) INFORMATION FOR SEQ ID NO:1212:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1212:

CACCACCGUC CAGGCCUC 18

(2) INFORMATION FOR SEQ ID NO:1213:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1213:

GCAGGCAGCU CAGCAAAU 18

(2) INFORMATION FOR SEQ ID NO:1214:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:1214:

UAAGGCUGUU UCCAACCU 18

(2) INFORMATION FOR SEQ ID NO:1215:

(i) SEQUENCE CHARACTERISTICS:
(A) LENGTH: 18 base pairs
(B) TYPE: nucleic acid ( C ) STRANDEDNESS: single
                ( D ) TOPOLOGY: linear ( x i ) SEQUENCE DESCRIPTION: SEQ ID NO:1215:

CCAACCUGAC UGAGAGCC        18

( 2 ) INFORMATION FOR SEQ ID NO:1216:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1216:

GAGAGCCGCU CCGAGUCC        18

( 2 ) INFORMATION FOR SEQ ID NO:1217:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1217:

UCUCUCCGCU CCCUGAUC        18

( 2 ) INFORMATION FOR SEQ ID NO:1218:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1218:

GCUCCCUGAU CGCCACGG        18

( 2 ) INFORMATION FOR SEQ ID NO:1219:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1219:

UGUCUCGGCU CGAGGUGG        18

( 2 ) INFORMATION FOR SEQ ID NO:1220:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:1220:

GUUCACAGCC CUCAUGAA        18

( 2 ) INFORMATION FOR SEQ ID NO:1221:

( i ) SEQUENCE CHARACTERISTICS:
                ( A ) LENGTH: 18 base pairs
                ( B ) TYPE: nucleic acid
                ( C ) STRANDEDNESS: single
                ( D ) TOPOLOGY: linear (xi) SEQUENCE DESCRIPTION: SEQ ID NO:1221:

GAUGGCUGCC UGCUGCUG  18

(2) INFORMATION FOR SEQ ID NO:1222:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1222:

GCUGCCUGCU GCUGCAGA  18

(2) INFORMATION FOR SEQ ID NO:1223:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1223:

GCCUGCUGCU GCAGAUGG  18

(2) INFORMATION FOR SEQ ID NO:1224:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1224:

UGCUGCAGAU GGACUUCG  18

(2) INFORMATION FOR SEQ ID NO:1225:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1225:

GACUUCGGUU UUCCCAAG  18

(2) INFORMATION FOR SEQ ID NO:1226:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1226:

AGCACCUGCU GGUGGAUU  18

(2) INFORMATION FOR SEQ ID NO:1227:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:1227:

ACACGCUGAC GUCUCCGC                                            18

( 2 ) INFORMATION FOR SEQ ID NO:1228:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1228:

CGUCUCCGCC CAUCGGGG                                            18

( 2 ) INFORMATION FOR SEQ ID NO:1229:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1229:

UCCUUCUGUC CUGAAGAC                                            18

( 2 ) INFORMATION FOR SEQ ID NO:1230:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1230:

UGCUCCGGAU CCCAGCUG                                            18

( 2 ) INFORMATION FOR SEQ ID NO:1231:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1231:

GAUCCCAGCU GCCUGCUA                                            18

( 2 ) INFORMATION FOR SEQ ID NO:1232:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1232:

CCCAGCUGCC UGCUAACG                                            18

( 2 ) INFORMATION FOR SEQ ID NO:1233:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:1233:

GGGAGCAGCC GUGCUGGU                                            18

( 2 ) INFORMATION FOR SEQ ID NO:1234:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1234:

AGACCCAGAC UGAGGUCC                                                  18

( 2 ) INFORMATION FOR SEQ ID NO:1235:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1235:

UUAGCCUGCC CAGUGAGU                                                  18

( 2 ) INFORMATION FOR SEQ ID NO:1236:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1236:

UCUGGCUGUC UCUCUCUG                                                   18

( 2 ) INFORMATION FOR SEQ ID NO:1237:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1237:

UCUCUCUGCC UCUCAAGU                                                  18

( 2 ) INFORMATION FOR SEQ ID NO:1238:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i x ) FEATURE:
        ( D ) OTHER INFORMATION: The letter "N"stands for any
            base. The letter "H"stands for
            A, U, or C.

( x i ) SEQUENCE DESCRIPTION: SEQ ID NO:1238:

NNNNUHNNNN N                                                                    11

( 2 ) INFORMATION FOR SEQ ID NO:1239:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i x ) FEATURE:
            ( D ) OTHER INFORMATION: The letter "N" stands for any
                base.

( x i ) SEQUENCE DESCRIPTION: SEQ ID NO:1239:

NNNNNCUGAN GAGNNNNNNC GAAANNNN                                                      28

( 2 ) INFORMATION FOR SEQ ID NO:1240:

( i ) SEQUENCE CHARACTERISTICS:
            ( A ) LENGTH: 15 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N" stands for any
                base. The letter "Y" stands for
                U or C. The letter "H" stands for
                A, U, or C.

( x i ) SEQUENCE DESCRIPTION: SEQ ID NO:1240:

NNNNNNNYNG HYNNN                                                                    15

( 2 ) INFORMATION FOR SEQ ID NO:1241:

( i ) SEQUENCE CHARACTERISTICS:
            ( A ) LENGTH: 47 base pairs
            ( B ) TYPE: nucleic acid
            ( C ) STRANDEDNESS: single
            ( D ) TOPOLOGY: linear ( i x ) FEATURE:
            ( D ) OTHER INFORMATION: The letter "N" stands for any
                base. The letter "H" stands for
                A, U, or C.

( x i ) SEQUENCE DESCRIPTION: SEQ ID NO:1241:

NNNNGAAGNN NNNNNNNNNA AAHANNNNN NACAUUACNN NNNNNNN                                  47

( 2 ) INFORMATION FOR SEQ ID NO:1242:

( i ) SEQUENCE CHARACTERISTICS:
            ( A ) LENGTH: 85 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1242:

UGGCCGGCAU GGUCCCAGCC UCCUCGCUGG CGCCGGCUGG GCAACAUUCC GAGGGGACCG                   60

UCCCCUCGGU AAUGGCGAAU GGGAC                                                         85

( 2 ) INFORMATION FOR SEQ ID NO:1243:

( i ) SEQUENCE CHARACTERISTICS:
            ( A ) LENGTH: 176 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:1243:

GGGAAAGCUU GCGAAGGGCG UCGUCGCCCC GAGCGGUAGU AAGCAGGGAA CUCACCUCCA                   60

AUUUCAGUAC UGAAAUUGUC GUAGCAGUUG ACUACUGUUA UGUGAUUGGU AGAGGCUAAG                   120

UGACGGUAUU GGCGUAAGUC AGUAUUGCAG CACAGCACAA GCCCGCUUGC GAGAAU                       176

CETP RIBOZYMES

BACKGROUND OF THE INVENTION

This invention relates to the methods for the prevention, inhibition of progression and regression of vascular diseases, in particular, inhibition of cholesterol ester transfer protein (CETP) inhibition.

The following is a discussion of relevant art, none of which is admitted to be prior art to the present invention.

Vascular diseases, which includes etiologies such as peripheral vascular disease, coronary heart disease (CHD), stroke and restenosis, remain the leading cause of death and disability in the United States and throughout the world. In 1990 alone, approximately 500,000 people died in the United States from CHD. Although, diet and life style can accelerate the rate of onset of vascular diseases, genetic predisposition leading to "dyslipidemia" is a major and significant factor attributing to vascular related deaths and disabilities(Anderson et al., 1987 JAMA 257, 2176). By "dyslipidemia" is meant abnormal levels of lipoproteins in plasma.

A variety of risk factors have been identified that are associated with increased risk of vascular disease (Barr et al., 1951 Am. J. Med. 11,480; Kannel et al., 1971 Ann. Intern. Med. 74, 1; Miller et al., 1975 Lancet 1, 16; Levy et al., 1984 Circulation 69, 325.; Lipid Research Clinics Program, 1984 JAMA 251, 351; Lipid Research Clinics Program, 1984 JAMA 251, 365; Anderson et al., 1987 JAMA 257, 2176; Blankenhorn et al., 1987 J. Am. Med. Assoc. 257, 3233.; Frick et al., 1987 N. Engl. J. Med. 317, 1237; Expert Panel, 1988 Arch. Intern. Med. 148, 36.; Grundy et al., 1989 Arch. Intern. Med. 149, 505.; La Rosa, 1990 Am. J. Cardiol. 65, 7F–10F). Among these are the dyslipidemias of high levels of low density lipoproteins (LDL) and low levels of high density lipoproteins (HDL), singly or in combination. Often the ratio of HDL cholesterol to that of LDL cholesterol is used to assess risk of vascular disease. Thus, a high ratio of HDL/LDL cholesterol is desirable, and intervention to increase the ratio by lowering LDL and elevating HDL, singly or in combination is desirable.

Familial hypercholesterolemia (FH), a genetic disorder caused by defective or deficient LDL receptors presents as a marked elevation in LDL and risk in vascular disease (Goldstein et al., 1989 "Familial hypercholesterolemia" In: The Metabolic Basis of Inherited Diseases, 6th Ed., Schiver, C. R., Beaudet, A. L., Sly, W. S., and Valle, D. editors, 1215). Homozygous FH is a relatively rare disorder (1 in 1,000, 000). Homozygous FH patients have extremely high levels of LDL with very short life expectancies. Therapy for these individuals include liver transplantation and LDL plasmaphoresis. Heterozygous FH is relatively common disorder (1 in 500). Heterozygous FH patients present with LDL levels approximately twice normal and are at risk for developing premature atherosclerosis followed by the common sequelae associated with vascular diseases, including myocardial infarction and stroke. Conventional therapy for heterozygous FH patients generally includes HMG CoA reductase inhibitors alone or in combination with bile acid sequestrants. Human prospective trials have demonstrated reduction in CHD related endpoints in hypercholesterolemic subjects treated with HMGCoA reductase inhibitors, bile acid sequestrants, Nicotinic acid, and gemfibrozil (La Rosa, 1990 Am. J. Cardiol. 65, 7F; Pedersen et al., 1994 Lancet 344, 1383).

Other conditions, such as apoE 3/4 and apoE4/4 genotype are also associated with increased LDL elevation and risk of CHD. However the direct causal relation between apoE4 polymorphism, elevated LDL and increased risk is unknown (Davignon et al., 1988 Arteriosclerosis 8, 1; Dallongeville et al., 1992 J. Lipid Res. 33, 447; Walden et al., 1994 Ann. Intern. Med. 120, 1026).

Low levels of HDL or hypoalphalipoproteinemia is a relatively common condition. The genetic basis for hypoalphalipoproteinemia is poorly understood, but likely results from multiple factors related to genetic predisposition and life style. Numerous prospective and retrospective studies have shown that HDL is inversely and strongly correlated with vascular disease. Therefore treatment to elevate HDL levels is warranted (Grundy et al., 1989 Arch. Intern. Med. 149, 505). It is also well recognized, that plasma triglyceride elevation is generally associated with low HDL levels, and insulin resistance (Reaven, 1988 Diabetes 37, 1595). Conventional therapies for elevated triglycerides and low HDL generally include treatment with fibrates. Gemfibrozil, a compound of this class, effectively lowers plasma triglycerides, and moderately elevates HDL (Frick, 1987 N. Engl. J. Med. 317, 1237). In a large human prospective trial, gemfibrozil has been shown to cause a significant reduction in vascular endpoints (Frick, 1987 supra).

The process termed reverse cholesterol transport (RCT; Bailey, 1965 Exp. Cell. Res. 37, 175; Glomset, 1968 J. Lipid Res. 9, 155) is a mechanism resulting in a net efflux of cholesterol present in peripheral tissues for disposal in bile. This multistep "hypothesized" pathway invokes removal of cholesteryl from peripheral tissues to HDL. Lecithin: cholesterol acyltransferase (LCAT), a circulating plasma enzyme, primarily mediates the esterification of HDL cholesterol to cholesteryl esters. CETP, also present in plasma, mediates HDL cholesteryl ester net transfer to apolipoprotein B (apoB)-containing lipoproteins including very low density lipoproteins (VLDL), intermediate density lipoproteins or remnants (IDL) and LDL. CETP-mediated cholesteryl ester enrichment of the LDL precursors, VLDL and IDL, ultimately contributes to the cholesterol content of LDL. Hepatic receptor-mediated LDL uptake, and a net flux of these delivered cholesteryl esters to the bile acid pool completes RCT. However, species that lack CETP (Oschry et al., 1982 J. Lipid Res. 23, 1099) or humans deficient in CETP (Koizumi et al., 1985 Atherosclerosis 58, 175) are unable to effectively transfer cholesteryl esters formed in HDL to the LDL precursor pool. Although the break in this link of the RCT pathway might predictably result in a marked deficiency in peripheral tissue cholesterol egress, surprisingly, this is not the case. In CETP deficient species, the HDL cholesteryl ester pool accumulates at the expense of the LDL pool. The HDL particles become enlarged and apoA-I, apoA-IV, and apoE-enriched (Brown et al., 1989 Nature 342, 448–451; Yamashita et al., 1990 J. Clin. Invest. 86, 688; Bisgaier et al., 1991 J. Lipid Res. 32, 21). Particles containing apoE can effectively be delivered to the liver as whole particles by facilitated mechanisms, including those utilizing the LDL receptor and the LDL receptor related protein (LRP) (Goldstein et al., 1985 Ann. Rev. Cell Biol. 1, 1; Mahley, 1988 Science 240, 622.; Beisiegel et al., 1989 Nature 341, 162; Bisgaier et al., 1989 J. Biol. Chem. 264, 862.). Thus, alternative mechanisms exist that facilitate tissue cholesterol egress and delivery of non-LDL cholesterol to liver in the absence of CETP.

Thus, CETP inhibition may inhibit or eliminate the RCT pathway thereby preventing the reduction in size and density of HDL, prolonging HDL half-life, and resulting in increased HDL levels. Additionally, the lack of transport of cholesteryl esters from HDL to apoB-containing lipoproteins may reduce LDL concentrations. Both these effects would result in an elevation of the HDL to LDL ratio. As high HDL/LDL ratios and HDL levels have been associated with anti-atherogenicity, diminishing CETP activity may prevent or inhibit progression and regression of vascular disease.

CETP is a 74 kDa glycoprotein that facilitates neutral lipid (cholesteryl esters and triglycerides) transfer between plasma lipoproteins (Zilversmit et al., 1975 Biochim. Biophys. Acta 409, 393; Ha et al., 1982 Comp. Biochem. Physiol. 71B, 265; Drayna et al., 1987 Nature 327, 632; Hesler et al., 1987 J. Biol. Chem. 262, 2275; Swenson et al., 1987 J. Biol. Chem. 262, 16271; Hesler et al., 1988 J. Biol. Chem. 263, 5020; Nagashima et al., 1988 J. Lipid Res. 29, 1643; Pape et al., 1991 Arterioscler. Thromb. 11, 1759). In non-human primates and rabbits, hepatic non-parenchymal cells are likely the major synthetic source of CETP (Pape et al., 1991 Arterioscler. Thromb. 11, 1759; Pape et al., 1991 J. Biol. Chem. 266, 12829; Rea et al., 1993 J. Lipid Res. 34, 1901), in that these cells have the highest cellular content of CETP mRNA relative to total RNA. Abundant amounts of CETP mRNA has also been shown in hepatic parenchymal cells, adipose, and spleen and to a lesser extent in the intestine and heart.

The level of CETP activity between species is highly variable (Ha et al., 1982 Comp. Biochem. Physiol. 71B, 265; Bisgaier et al., 1993 J. Lipid Res. 34, 1625). In general, species with high CETP activity (e.g., humans and rabbits) are susceptible to dietary induced atherosclerosis, while species with little or no CETP activity (e.g., mice, rats and dogs) are resistant (Koizumi et al., 1985 Atherosclerosis 58, 175; Inazu et al., 1990 N. Engl. J. Med. 323, 1234; Agellon et al., 1991 J. Biol. Chem. 260, 10796; Bisgaier et al., 1991 J. Lipid Res. 32, 21; Marotti et al., 1992 Arterioscler. Thrombosis 12, 736). Likewise, those species with little or no CETP activity have anti-atherosclerotic lipoprotein profiles: plasma HDL levels are elevated and LDL are reduced (Ha et al., 1982 Comp. Biochem. Physiol. 71B, 265). Infusions of inhibitory CETP monoclonal or polyclonal antibodies into rabbits or infusion of CETP into rats will invert the lipoprotein profiles (Ha et al., 1985 Biochim. Biophys. Acta. 833, 203; Abbey et al., 1989 Biochim. Biophys. Acta 1003, 20; Groener et al., 1989 Biochim. Biophys. Acta 1002, 93; Whitlock et al., 1989 J. Clin. Invest. 84, 129.). Unlike control mice of similar genetic background, CETP transgenic mice develop atherosclerotic lipoproteins and atherosclerosis (Marotti et al., 1992 Arterioscler. Thromb.12, 736).

Recent studies of a Japanese family have shown that a deficiency in plasma CETP associated with marked elevation of HDL, its associated apolipoproteins (apoA-I, apoE, apoA-IV) and a rarity of coronary artery disease (Koizumi et al., 1985 Atherosclerosis 58, 175; Brown et al., 1989 Nature 342, 448; Inazu et al., 1990 N. Engl. J. Med. 323, 1234; Bisgaier et al., 1991 J. Lipid Res. 32, 21.; Ikewaki et al., 1991 Arterioscler. Thromb. 11, 1400a; Koizumi et al., 1991 Atherosclerosis 90, 189). These individuals were identified through routine cholesterol screening and have no other hyperlipidemia related disease. The defect has been identified as a G to A substitution in the fourteenth intron of CETP pre-messenger ribonucleic acid (RNA) (Brown et al., 1989 Nature 342, 448). This splice donor defect is also the cause of the deficiency in additional Japanese families (Inazu et al., 1990 N. Engl. J. Med. 323, 1234; Koizumi et al., 1991 Atherosclerosis 90, 189; Hirano et al., 1993 Atherosclerosis 100, 85). In a more recent study, the deficiency (both homozygous and heterozygous) has been shown to be associated with a large proportion of Japanese with hyperalphalipoproteinemia (Inazu et al., 1992 Horm. Metab. Res. 24, 284; Hirano et al., 1993 Atherosclerosis 100, 85). A missense mutation at nucleotide 1506 (G for A) also has been identified in exon 15 of the CETP gene, resulting in a substation of a glycine for aspartic acid at amino acid 442 (Takahashi et al., 1993 J. Clin. Invest. 92, 2060). The two subjects heterozygous for the missense mutation had three times the normal HDL levels. Overall these studies suggest that even partial reduction in CETP levels, as found in heterozygous individuals, is associated with elevated HDL. This apparently benign condition (CETP deficiency) has been coined the "longevity syndrome" (Koizumi et al., 1985 Atherosclerosis 58, 175).

Although CETP facilitates an equimolar exchange of neutral lipids, net transfer of cholesteryl ester to LDL occurs due to (1) concentration and core lipid composition of exchange partners and (2) residence time of lipoproteins (Nichols et al., 1965 J. Lipid. Res. 206; Pattnaik et al., 1978 Biochim. Biophys. Acta 530, 428; Barter et al., 1979 Metabolism 28, 230). Under basal conditions (i.e., overnight fast), CETP facilitates transfer below maximal velocity, while postprandially CETP appears to facilitate transfer at or near maximal velocity (Tall et al., 1986 J. Clin. Invest. 77, 1163; Mann et al., 1991 J. Clin. Invest. 88, 2059; Bisgaier et al., 1993 J. Lipid Res. 34, 1625). It is also likely, but has not been systematically shown, that individuals with elevated triglycerides would have elevated CETP activity (but not necessarily increased CETP mass). In general, these subjects have reduced levels of HDL and elevated LDL. These consequences, in part may be the result of events facilitated by CETP.

The complete amino acid sequence of human, rabbit, cynomolgus monkey and hamster CETP are known (Drayna et al., 1987 Nature 327, 632; Nagashima et al., 1988 J. Lipid Res. 29, 1643; Jiang et al., 1991 J. Biol. Chem. 266, 4631; Pape et al., 1991 Arterioscler. Thromb. 11, 1759). Human plasma levels are approximately 1–2 μg/ml, while rabbit levels are approximately 4 μg/ml. Cholesterol feeding in rabbits elevates tissue CETP mRNA, plasma CETP, and maximal plasma activity approximately 4 fold (Quinet et al., 1990 J. Clin. Invest. 85, 357; McPherson et al., 1991 Arterioscler. Thromb. 11, 797). The protein is stable to heat, limited proteolysis, but not oxidation. CETP has been mapped with neutral and inhibitory monoclonal antibodies and by site-directed mutagenesis (Hesler et al., 1987 J. Biol. Chem. 262, 2275; Hesler et al., 1988 J. Biol. Chem. 263, 5020; Wang et al., 1991 Biochemistry 30, 3484). Stable transfection of the human gene in CHO cells has been accomplished (Wang et al., 1991 Biochemistry 30, 3484; Wang et al., 1992 J. Biol. Chem. 267, 17487). However, the protein has not been crystallized nor have the lipid binding domains been identified. Furthermore, the mechanisms by which CETP facilitates transfer are poorly understood.

Direct pharmacological inhibition of the existing protein in plasma or targeting CETP gene expression might lead to reduced plasma activity and result in a beneficial lipoprotein profile (i.e., HDL elevation and LDL diminution) and a reduced risk of coronary heart disease. However a synthetic compound approach for the direct inhibition of the plasma CETP has not yet been promising (Bisgaier et al., 1994 Lipids 29).

The gene encoding CETP is composed of 16 exons of various sizes (32–250 bp) and spans approximately 25 kb on the long arm (q12–21) of chromosome 16 (Lusis et al., 1987 Genomics 1,232; Agellon et al., 1990 Biochemistry 29, 1372). Cloning and sequencing of the human CETP cDNA has been reported and shown to contain an open reading frame and 3' untranslated region of 1656 nucleotides in length (Drayna et al., 1987 Nature 327, 632). Analysis of amino-acid and nucleic acid sequence has indicated a protein that is unique among eukaryotic species. A pentanucleotide amino acid stretch in the precursor protein signal peptide of CETP is conserved among the lipid metabolism associated proteins, for example apoA-IV, apoA-I, and lipoprotein lipase (Agellon et al., 1990 Biochemistry 29, 1372). This conservation occurs at both the nucleotide and the amino-acid level. This small but highly conserved region is found only in the precursor protein species and is removed before secretion of the mature protein into the blood stream. Other less conserved homologies have been noted with two lipopolysaccaride binding proteins, bacterial permeability increasing protein found in leukocyte granules and plasma lipopolysaccharide binding protein (Tall, 1993 J. Lipid Res. 34, 1255).

A single predominant splicing variant of the CETP message has been identified and characterized. This variant CETP mRNA lacks exon 9 and accounts for between 14–46% of total CETP mRNA with the highest percentage of this variant seen in the spleen. While the function of this abundant splice variant is not clearly understood, when coordinately expressed with full-length CETP in Chinese Hamster Ovary (CHO) cells, it was shown not to be secreted and capable of inhibiting secretion of the full length CETP protein (Quinet et al., 1993 J. Biol. Chem. 268, 16891).

A consequence of inhibiting CETP, besides that of favorably increasing the HDL/LDL cholesterol ratio, is a change in the distribution and level of apoE. In species lacking CETP (e.g., rats), during monoclonal antibody induced inhibition of CETP in hamsters, and in human CETP deficiency, plasma apoE levels are elevated (Yamashita et al., 1990 J. Clin. Invest. 86, 688; Eto et al., 1990 Artery 17, 202; Hirano et al., 1993 Atherosclerosis 100, 85; Takahashi et al., 1993 J. Clin. Invest. 92, 2060; Bisgaier et al., 1991 J. Lipid Res. 32, 21; Evans et al., 1994 J. Lipid Res. 35, 1634). Furthermore, HDL apoE-enrichment was observed (Evans et al., 1994 J. Lipid Res. 35, 1634). Recent in vitro studies have revealed mechanisms by which apoE-enriched HDL are protective (Yamada et al., 1992 J. Clin. Invest. 706; Saxena et al., 1993 J. Biol. Chem. 268, 14812). Additional studies have also demonstrated that apoE deficiency causes profound and accelerated rates of atherosclerosis in mice, a species not normally susceptible to atherosclerosis (Plump et al., 1992 Cell 71, 343; Zhang et al., 1992 Science 258, 468). Thus an expected and desirable consequence of CETP inhibition includes elevation of apoE-rich HDL. In apoE deficiency, overexpression of apoA-I can also afford protection against atherosclerosis (Plump et al., 1994 Proc. Natl. Acad. Sci. USA 91, 9607), and elevation of this protein is also an expected consequence of CETP inhibition (Koizumi et al., 1985 Atherosclerosis 58, 175; Eto et al., 1990 Artery 17, 202; Hirano et al., 1993 Atherosclerosis 100, 85; Takahashi et al., 1993 J. Clin. Invest. 92, 2060).

There currently exists no practical therapeutic treatment for interfering with or blocking CETP activity in humans. Although not practical, repetitive anti-CETP combined with anti-LDL plasmaphoreseis resulted in favorable changes in LDL and HDL levels and HDL/LDL ratios in a limited number of human studies (Davidson, U.S. Pat. No. 5,279, 540). Although plasma CETP levels markedly decreased with duration of plasmaphoresis treatments, neither anti-CETP plasmaphoresis alone nor control non-immune plasmaphoresis data were reported. Several potential inhibitors are being explored in various laboratories. These inhibitors include monoclonal antibodies and an inhibitor protein recently found in baboon plasma tentatively identified as the N-terminal fragment of apolipoprotein C-I (Kushwaha et al., 1993 J. Lipid Res. 1993, 1285; Kushwaha et al., WO 93/11782). In the current application, a ribozyme, antisense or 2–5A-antisense or triplex DNA approach is described. The advantage of these approaches is their ability to selectively target specific regions of the CETP mRNA.

SUMMARY OF THE INVENTION

The invention features novel nucleic acid-based techniques [e.g., enzymatic RNA molecules (ribozymes), antisense nucleic acids, 2–5A antisense chimeras, triplex DNA] and methods for their use for: (1) treatment of dyslipidemias by decreasing lipoproprotein risk factors, in particular, decreasing high levels of LDL or increasing low levels of HDL, or a combination of both and (2) for the prevention, inhibition of progression, and regression of vascular diseases, particularly, those diseases associated with (but not limited to) peripheral vascular disease, coronary heart disease, stroke, vascular complications of diabetes, transplant, atherectomy, and angloplastic restenosis.

The uniqueness of the CETP coding region and protein afford an increased safety margin when contemplating sequence-specific therapeutics targeting of the mRNA, such as ribozymes or antisense nucleic acids or 2–5A antisense chimeras, since there would be a reduced likelihood of non-specific activity from these therapeutics.

In a preferred embodiment, the invention features use of nucleic acid-based techniques to treat lipoprotein risk factors and/or prevent vascular diseases by inhibiting the synthesis of cholestryl ester transfer protein (CETP).

Those in the art will recognize the other potential targets, for e.g., apolipoprotein B, are also suitable for treatment with nucleic acid-based techniques described in the present invention.

By "inhibit" is meant that the activity of CETP or level of mRNAs encoded by CETP is reduced below that observed in the absence of the nucleic acid, particularly, inhibition with ribozymes and preferably is below that level observed in the presence of an inactive RNA molecule able to bind to the same site on the mRNA, but unable to cleave that RNA.

By "enzymatic nucleic acid (NA) molecule" it is meant a nucleic acid molecule which has complementarity in a substrate binding region to a specified gene target, and also has an enzymatic activity which is active to specifically cleave RNA in that target. That is, the enzymatic nucleic acid molecule is able to intermolecularly cleave RNA and thereby inactivate a target RNA molecule. This complementarity functions to allow sufficient hybridization of the enzymatic nucleic acid molecule to the target RNA to allow the cleavage to occur. One hundred percent complementarity is preferred, but complementarity as low as 50–75% may also be useful in this invention.

By "equivalent" RNA to CETP is meant to include those naturally occuring RNA molecules RNA molecules associated with cardiovascular diseases in various animals, including human, rabbit and monkey. Such a molecule will generally contain some ribonucleotides, but the other nucleotides may be substituted at the 2'-hydroxyl position and in other locations with other moieties as discussed below.

By "antisense nucleic acid" is meant a non-enzymatic nucleic acid molecule that binds to another RNA (target RNA) by means of RNA-RNA or RNA-DNA or RNA-PNA (protein nucleic acid; Egholm et al., 1993 Nature 365, 566)

interactions and alters the activity of the target RNA (for a review see Stein and Cheng, 1993 *Science* 261, 1004). By "2–5A antisense chimera" is meant, an antisense oligonucleotide containing a 5' phosphorylated 2'–5'-linked adenylate residues. These chimeras bind to target RNA in a sequence-specific manner and activate a cellular 2–5A-dependent ribonuclease which in turn cleaves the target RNA (Torrence et al., 1993 *Proc. Natl. Acad. Sci. USA* 90, 1300).

By "triplex DNA" is meant an oligonucleotide that can bind to a double-stranded DNA in a sequence-specific manner to form a triple-strand helix. Triple-helix formation has been shown to inhibit transcription of the targeted gene (Duval-Valentin et al., 1992 *Proc. Natl. Acad. Sci. USA* 89, 504).

By "gene" is meant a nucleic acid that encodes an RNA.

By "complementarity" is meant a nucleic acid that can form hydrogen bond(s) with other RNA sequence by either traditional Watson-Crick or other non-traditional types (for example, Hoogsteen type) of base-paired interactions.

Six basic varieties of naturally-occurring enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over other technologies, since the concentration of ribozyme necessary to affect a therapeutic treatment is lower. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

Ribozymes that cleave the specified sites in CETP mRNAs represent a novel therapeutic approach to vascular disease. Applicant indicates that ribozymes are able to inhibit the activity of CETP and that the catalytic activity of the ribozymes is required for their inhibitory effect. Those of ordinary skill in the art, will find that it is clear from the examples described that other ribozymes that cleave these sites in CETP mRNAs may be readily designed and are within the invention.

In preferred embodiments of this invention, the enzymatic nucleic acid molecule is formed in a hammerhead or hairpin motif, but may also be formed in the motif of a hepatitis delta virus, group I intron or RNaseP RNA (in association with an RNA guide sequence) or Neurospora VS RNA. Examples of such hammerhead motifs are described by Rossi et al., 1992, *Aids Research and Human Retroviruses* 8, 183, of hairpin motifs by Hampel et al., EP0360257, Hampel and Tritz, 1989 *Biochemistry* 28, 4929, and Hampel et al., 1990 *Nucleic Acids Res.* 18, 299, and an example of the hepatitis delta virus motif is described by Perrotta and Been, 1992 *Biochemistry* 31, 16; of the RNaseP motif by Guerrier-Takada et al., 1983 *Cell* 35, 849, *Neurospora* VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799) and of the Group I intron by Cech et al., U.S. Pat. No. 4,987,071. These specific motifs are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule.

In a preferred embodiment the invention provides a method for producing a class of enzymatic cleaving agents which exhibit a high degree of specificity for the RNA of a desired target. The enzymatic nucleic acid molecule is preferably targeted to a highly conserved sequence region of a target mRNAs encoding CETP proteins such that specific treatment of a disease or condition can be provided with either one or several enzymatic nucleic acids. Such enzymatic nucleic acid molecules can be delivered exogenously to specific cells as required. Alternatively, the ribozymes can be expressed from DNA/RNA vectors that are delivered to specific cells.

Synthesis of nucleic acids greater than 100 nucleotides in length is difficult using automated methods, and the therapeutic cost of such molecules is prohibitive. In this invention, small enzymatic nucleic acid motifs (e.g., of the hammerhead or the hairpin structure) are used for exogenous delivery. The simple structure of these molecules increases the ability of the enzymatic nucleic acid to invade targeted regions of the mRNA structure. However, these catalytic RNA molecules can also be expressed within cells from eukaryotic promoters (e.g., Scanlon et al., 1991, *Proc. Natl. Acad. Sci. USA*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 5531–4; Ojwang et al., 1992 *Proc. Natl. Acad. Sci. USA* 89, 10802–6; Chen et al., 1992 *Nucleic Acids Res.*, 20, 4581–9; Sarver et al., 1990 *Science* 247, 1222–1225). Those skilled in the art realize that any ribozyme can be expressed in eukaryotic cells from the appropriate DNA/RNA vector. The activity of such ribozymes can be augmented by their release from the primary transcript by a second ribozyme (Draper et al., PCT WO 93/23569, and Sullivan et al., PCT WO 94/02595, both hereby incorporated in their totality by reference herein; Ohkawa et al., 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25856).

Such ribozymes are useful for the prevention of the diseases and conditions discussed above, and any other diseases or conditions that are related to the level of CETP activity in a cell or tissue. By "related" is meant that the inhibition of CETP mRNAs and thus reduction in the level of protein activity will relieve to some extent the symptoms of the disease or condition.

Ribozymes are added directly, or can be complexed with cationic lipids, packaged within liposomes, or otherwise delivered to target cells. The nucleic acid or nucleic acid complexes can be locally administered to relevant tissues ex vivo, or in vivo through injection, infusion pump or stent, with or without their incorporation in biopolymers. In preferred embodiments, the ribozymes have binding arms which are complementary to the sequences in Tables II, IV, VI and VII. Examples of such ribozymes are shown in Tables III, V, VI and VII. Examples of such ribozymes consist essentially of sequences defined in these Tables. By "consists essentially of" is meant that the active ribozyme contains an enzymatic center equivalent to those in the examples, and binding arms able to bind mRNA such that cleavage at the target site occurs. Other sequences may be present which do not interfere with such cleavage.

In another aspect of the invention, ribozymes that cleave target molecules and inhibit CETP activity are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. Delivery of ribozyme expressing vectors could be systemic, such as by intravenous or intramuscular administration, by administration to target cells ex-planted from the patient followed by reintroduction into the patient, or by any other means that would allow for introduction into the desired target cell.

By "vectors" is meant any nucleic acid- and/or viral-based technique used to deliver a desired nucleic acid.

In a preferred embodiment nucleic acids targeted to Exon 9 of CETP gene is described. A single predominant alternate-splicing variant of the CETP message that lacks exon 9 has been identified and characterized (Inazu et al., 1991 *Biochemistry* 31, 2352; Quinet et al., 1993 *J. Biol. Chem.* 268, 16891). While the function of this abundant splice variant is not clearly understood, it is known to be not secreted and capable of inhibiting secretion of the full-length CETP protein. (Quinet et. al. 1993 J. Biol. Chem. 16891). Inhibition of full-length CETP secretion is believed to occur due to a heterodimeric complex formation between the full-length and the spliced variant of CETP. This suggests that the spliced variant of CETP might be beneficial in regulating the plasma level of CETP. Nucleic acid-based therapeutics of this invention, therefore, may be selectively targeted to block the expression of exon 9-containing CETP.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 is a diagrammatic representation of the hammerhead ribozyme domain known in the art. Stem II can be $\geq 2$ base-pair long.

FIG. 2a is a diagrammatic representation of the hammerhead ribozyme domain known in the art; FIG. 2b is a diagrammatic representation of the hammerhead ribozyme as divided by Uhlenbeck (1987, *Nature*, 327, 596–600) into a substrate and enzyme portion; FIG. 2c is a similar diagram showing the hammerhead divided by Haseloff and Gerlach (1988, *Nature*, 334, 585–591) into two portions; and FIG. 2d is a similar diagram showing the hammerhead divided by Jeffries and Symons (1989, *Nucl. Acids. Res.*, 17, 1371–1371) into two portions.

FIG. 3 is a diagrammatic representation of the general structure of a hairpin ribozyme. Helix 2 (H2) is provided with a least 4 base pairs (i.e., n is 1, 2, 3 or 4) and helix 5 can be optionally provided of length 2 or more bases (preferably 3–20 bases, i.e., m is from 1–20 or more). Helix 2 and helix 5 may be covalently linked by one or more bases (i.e., r is $\geq 1$ base). Helix 1, 4 or 5 may also be extended by 2 or more base pairs (e.g., 4–20 base pairs) to stabilize the ribozyme structure, and preferably is a protein binding site. In each instance, each N and N' independently is any normal or modified base and each dash represents a potential base-pairing interaction. These nucleotides may be modified at the sugar, base or phosphate. Complete base-pairing is not required in the helices, but is preferred. Helix 1 and 4 can be of any size (i.e., o and p is each independently from 0 to any number, e.g., 20) as long as some base-pairing is maintained. Essential bases are shown as specific bases in the structure, but those in the art will recognize that one or more may be modified chemically (abasic, base, sugar and/or phosphate modifications) or replaced with another base without significant effect. Helix 4 can be formed from two separate molecules, i.e., without a connecting loop. The connecting loop when present may be a ribonucleotide with or without modifications to its base, sugar or phosphate. "q" is $\geq 2$ bases. The connecting loop can also be replaced with a non-nucleotide linker molecule. H, refers to bases A, U or C. Y refers to pyrimidine bases.

Figure 6B:
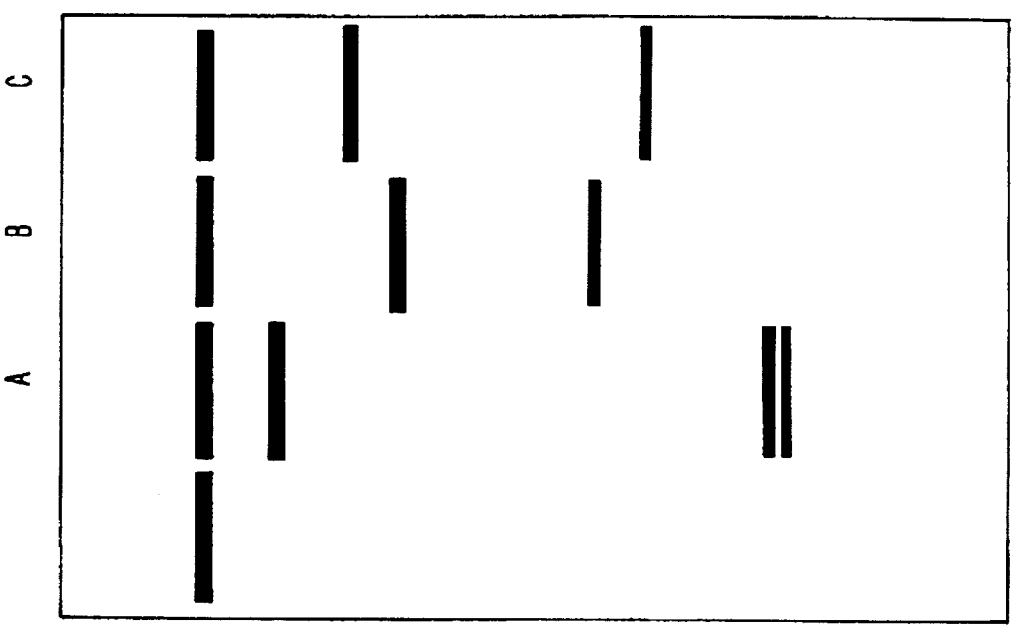
Figure 6A:
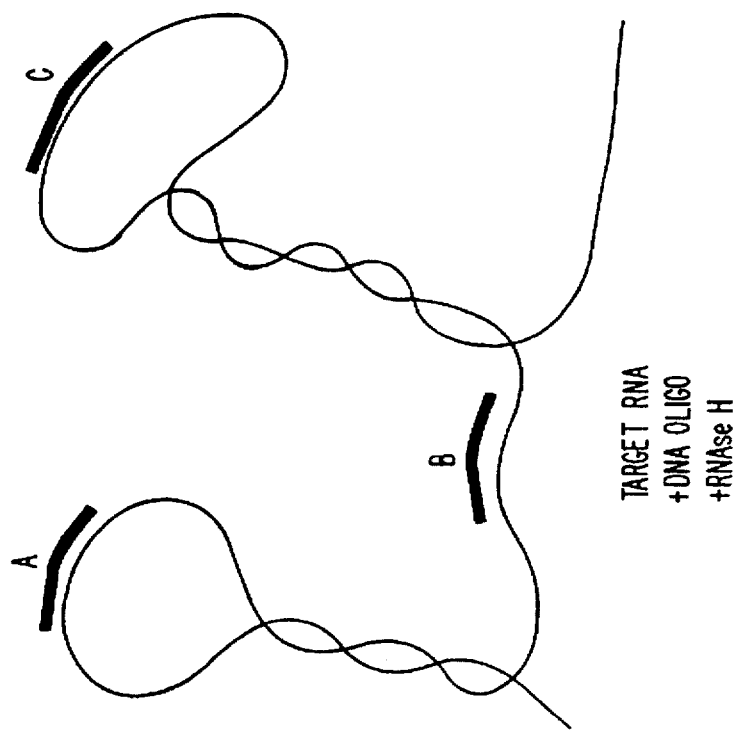

FIG. 6 is a schematic representation of an RNAseH accessibility assay. Specifically, the left side of FIG. 6 is a diagram of complementary DNA oligonucleotides bound to accessible sites on the target RNA. Complementary DNA oligonucleotides are represented by broad lines labeled A, B, and C. Target RNA is represented by the thin, twisted line. The right side of FIG. 6 is a schematic of a gel separation of uncut target RNA from a cleaved target RNA. Detection of target RNA is by autoradiography of body-labeled, T7 transcript. The bands common to each lane represent uncleaved target RNA; the bands unique to each lane represent the cleaved products.

RIBOZYMES

Ribozymes of this invention block to some extent CETP production and can be used to treat disease or diagnose such disease. Ribozymes will be delivered to cells in culture and to cells or tissues in animal models of cardiovascular disorders. Ribozyme cleavage of CETP encoded mRNAs in these systems may alleviate disease symptoms.

Target sites

Targets for useful ribozymes can be determined as disclosed in Draper et al., "Method and reagent for treatment of arthritic conditions U.S. Ser. No. 08/152,487, filed Nov. 12, 1993, and hereby incorporated by reference herein in totality. Rather than repeat the guidance provided in those documents here, below are provided specific examples of such methods, not limiting to those in the art. Ribozymes to such targets are designed as described in those applications and synthesized to be tested in vitro and in vivo, as also described.

The sequence of human and rabbit CETP mRNAs were screened for optimal ribozyme target sites using a computer folding algorithm. Hammerhead or hairpin ribozyme cleavage sites were identified. These sites are shown in Tables II, IV, VI and VII (All sequences are 5' to 3' in the tables) The nucleotide base position is noted in the Tables as that site to be cleaved by the designated type of ribozyme. While rabbit and human sequences can be screened and ribozymes thereafter designed, the human targeted sequences are of most utility. However, as discussed in Stinchcomb et al., "Method and Composition for Treatment of Restenosis and Cancer Using Ribozymes," filed May 18, 1994, U.S. Ser. No. 08/245,466, rabbit targeted ribozymes may be useful to test efficacy of action of the ribozyme prior to testing in humans. The nucleotide base position is noted in the Tables as that site to be cleaved by the designated type of ribozyme.

Hammerhead or hairpin ribozymes are designed that could bind and were individually analyzed by computer folding (Jaeger et al., 1989 *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 bases on each arm are able to bind to, or otherwise interact with, the target RNA.

Referring to FIG. 6, mRNA were screened for accessible cleavage sites by the method described generally in McSwiggen, U.S. patent application Ser. No. 07/883,849 filed on May 1, 1992, entitled "Assay for ribozyme target site", hereby incorporated by reference herein. Briefly, DNA oligonucleotides representing potential hammerhead or hairpin ribozyme cleavage sites were synthesized. A polymerase chain reaction is used to generate substrates for T7 RNA polymerase transcription from human and rabbit CETP cDNA clones. Labeled RNA transcripts are synthesized in vitro from the templates. The oligonucleotides and the labeled transcripts are annealed, RNAseH is added and the mixtures are incubated for the designated times at 37° C. Reactions are stopped and RNA separated on sequencing polyacrylamide gels. The percentage of the substrate cleaved is determined by autoradiographic quantitation using a PhosphorImaging system. From these data, hammerhead or hairpin ribozyme sites are chosen as the most accessible.

Ribozymes of the hammerhead or hairpin motif are designed to anneal to various sites in the mRNA message. The binding arms are complementary to the target site sequences described above. The ribozymes are chemically synthesized. The method of synthesis used follows the procedure for normal RNA synthesis as described in Usman et al., 1987 *J. Am. Chem. Soc.*, 109, 7845 and in Scaringe et al., 1990 *Nucleic Acids Res.*, 18, 5433 and made use of common nucleic acid protecting and coupling groups, such as dimethoxytrityl at the 5'-end, and phosphoramidites at the 3'-end. The average stepwise coupling yields are >98%. Inactive ribozymes are synthesized by substituting a U for $G_5$ and a U for $A_{14}$ (numbering from Hertel et al., 1992 *Nucleic Acids Res.*, 20, 3252). Hairpin ribozymes are synthesized in two parts and annealed to reconstruct the active ribozyme (Chowrira and Burke, 1992 *Nucleic Acids Res.*, 20, 2835–2840). Ribozymes are also synthesized from DNA templates using bacteriophage T7 RNA polymerase (Milligan and Uhlenbeck, 1989, *Methods Enzymol.* 180, 51). All ribozymes are modified extensively to enhance stability by modification with nuclease resistant groups, for example, 2'-amino, 2'-C-allyl, 2'-flouro, 2'-O-methyl, 2'-H (for a review see Usman and Cedergren, 1992 TIBS 17, 34). Ribozymes are purified by gel electrophoresis using general methods or are purified by high pressure liquid chromatography (HPLC; See Usman et al., Synthesis, deprotection, analysis and purification of RNA and ribozymes, filed May, 18, 1994, U.S. Ser. No. 08/245,736 the totality of which is hereby incorporated herein by reference) and are resuspended in water.

The sequences of the ribozymes that are chemically synthesized, useful in this study, are shown in Tables III, V, VI and VII. Those in the art will recognize that these sequences are representative only of many more such sequences where the enzymatic portion of the ribozyme (all but the binding arms) is altered to affect activity. For example, stem-loop II sequence of hammerhead ribozymes listed in Tables III and V (5'-GGCCGAAAGGCC-3') can be altered (substitution, deletion, and/or insertion) to contain any sequences provided a minimum of two base-paired stem structure can form. Similarly, stem-loop IV sequence of hairpin ribozymes listed in Tables VI and VII (5'-CACGUUGUG-3') can be altered (substitution, deletion, and/or insertion) to contain any sequence, provided a minimum of two base-paired stem structure can form. The sequences listed in Tables III, V, VI and VII may be formed of ribonucleotides or other nucleotides or non-nucleotides. Such ribozymes are equivalent to the ribozymes described specifically in the Tables.

Optimizing Ribozyme Activity

Ribozyme activity can be optimized as described by Stinchcomb et al., supra. The details will not be repeated here, but include altering the length of the ribozyme binding arms (stems I and III, see FIG. 2c), or chemically synthesizing ribozymes with modifications that prevent their degradation by serum ribonucleases (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162, as well as Usman, N. et al. U.S. patent application Ser. No. 07/829,729, and Sproat, European Patent Application 92110298.4 which describe various chemical modifications that can be made to the sugar moieties of enzymatic RNA molecules, modifications which enhance their efficacy in cells, and removal of stem II bases to shorten RNA synthesis times and reduce chemical requirements. (All these publications are hereby incorporated by reference herein.), Sullivan, et al., supra, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al; supra and Draper et al., supra which have been incorporated by reference herein.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Lisziewicz et al., 1993 *Proc. Natl. Acad. Sci. U.S.A.*, 90, 8000–4). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors).

In a preferred embodiment of the invention, a transcription unit expressing a ribozyme that cleaves mRNAs encoded by CETP is inserted into a plasmid DNA vector or an adenovirus or adeno-associated virus DNA viral vector or a retroviral RNA vector. Viral vectors have been used to transfer genes and lead to either transient or long term gene expression (Zabner et al., 1993 *Cell* 75, 207; Carter, 1992 *Curr. Opi. Biotech.* 3, 533). The adenovirus vector is delivered as recombinant adenoviral particles. The DNA may be delivered alone or complexed with vehicles (as described for RNA above). The recombinant adenovirus or AAV particles are locally administered to the site of treatment, e.g., through incubation or inhalation in vivo or by direct application to cells or tissues ex vivo.

In another preferred embodiments, the ribozyme is administered to the site of CETP expression (e.g., liver cells) in an appropriate liposomal vesicle.

EXAMPLE 1

CETP Hammerhead ribozymes

By engineering ribozyme motifs we have designed several ribozymes directed against CETP encoded mRNA sequences. These ribozymes are synthesized with modifications that improve their nuclease resistance. The ability of ribozymes to cleave target sequences in vitro was evaluated.

Several common human cell lines, such as HepG2, are available that can be induced to express endogenous CETP for experimental purposes. Alternatively, non-human cell lines have been developed which constitutively express a cDNA encoding for human CETP (Wang et al., 1991 Biochemistry 30, 3484; Wang et al., 1992 J. Biol. Chem. 267, 17487). Additional lines expressing human or rabbit full length or exon 9 deleted cDNA under the control of inducible or constitutive promoters could readily be developed by those skilled in the art. Several rabbit animal models of experimental hypercholesterolemia are available. New Zealand white rabbits fed with high cholesterol diets have been shown to develop atherosclerotic disease (Clarkson et al., 1988 in Use of Animal Models For Research in Human Nutrition, Comparative Animal Nutrition vol. 6, Bexnen and West, eds.) and Watanabe rabbits are a model of homozygous FH (defective LDL receptor) and present with increased cholesterol levels and spontaneous development of atherosclerosis and tendinous xanthomas (Watanbe, 1980 Atherosclerosis 36, 261). CETP protein levels can be measured clinically or experimentally by ELISA, or radioimmuno assay. CETP enzyme activity can be measured in vitro or ex vivo by the use of a fluorescently labeled substrate (Bisgaier et al., 1993 J. Lipid Res. 34, 1625; Bisgaier et al., 1994 Lipids 29, in press). CETP encoded mRNA levels can be assessed by Northern analysis, RNAse protection, primer extension analysis or quantitative RT-PCR. Ribozymes that block the induction of CETP activity and/or CETP protein encoding mRNAs by more than 20% in vitro can be identified.

RNA ribozymes and/or genes encoding them will be delivered by either free delivery, liposome delivery, cationic lipid delivery, adeno-associated virus vector delivery, adenovirus vector delivery, retrovirus vector delivery or plasmid vector delivery in these animal model (e.g., transgenic mouse) experiments. One dose of a ribozyme vector that constitutively expresses the ribozyme or one or more doses of a stable anti-CETP ribozyme or a transiently expressing ribozyme vector may reduce the incidence or severity of atherosclerotic lesions or heart disease.

Diagnostic uses

Ribozymes of this invention may be used as diagnostic tools to examine genetic drift and mutations within diseased cells or to detect the presence of CETP RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with CETP related condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus each analysis will require two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., CETP) is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Other embodiments are within the following claims.

TABLE I

Characteristics of Ribozymes

Group I Introns

Size: ~200 to >1000 nucleotides
Requires a U in the target sequence immediately 5' of the cleavage site.
Binds 4-6 nucleotides at 5' side of cleavage site.
Over 75 known members of this class. Found in *Tetrahymena thermophila* rRNA, fungal mitochondria, chloroplasts, phage T4, RNAseP RNA (M1 RNA)

Size: ~290 to 400 nucleotides.
RNA portion of a ribonucleoprotein enzyme. Cleaves tRNA precursors to form mature tRNA.
Roughly 10 known members of this group all are bacterial in origin.

Hammerhead Ribozyme

Figure 1:
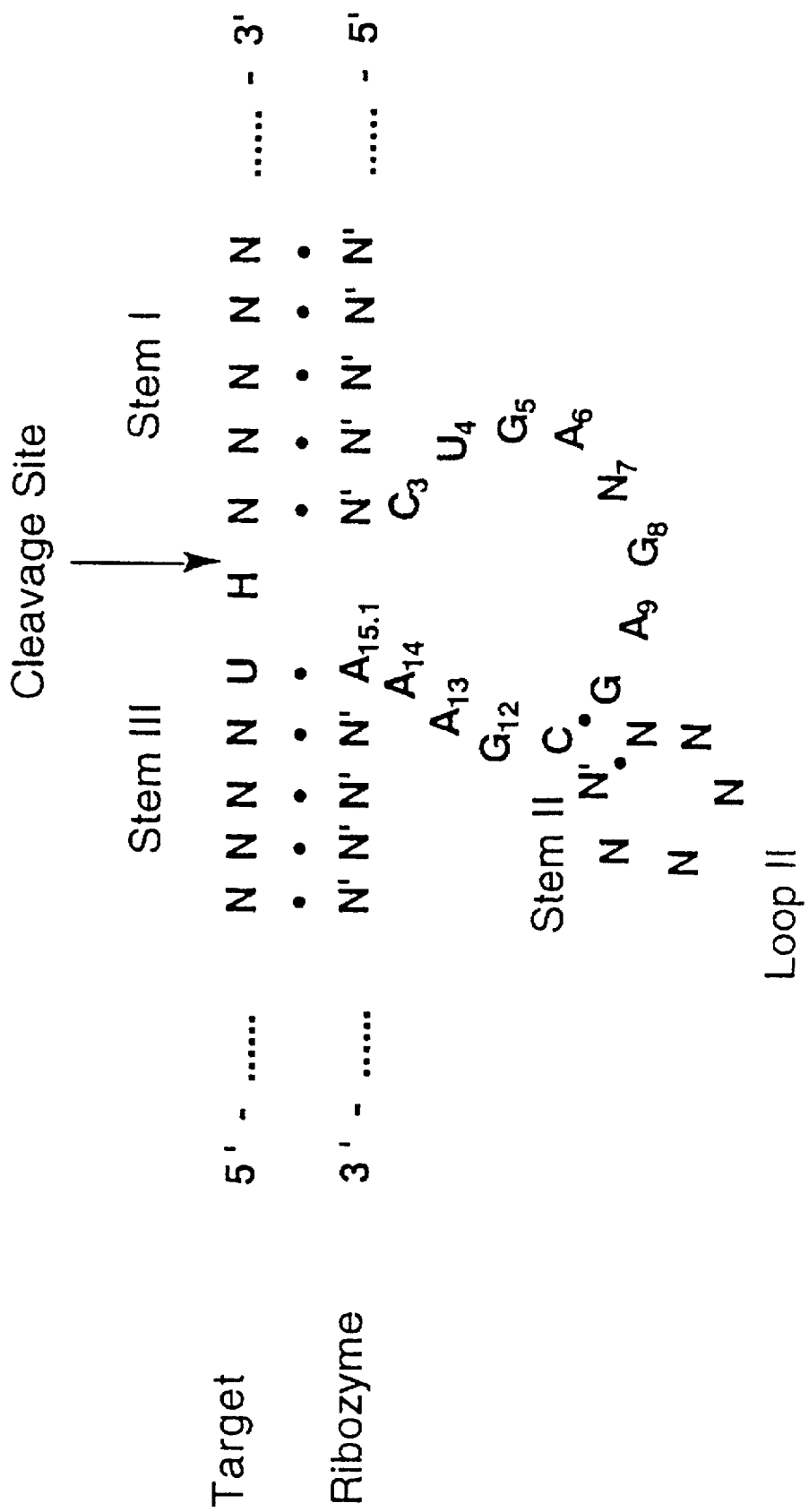

Size: ~13 to 40 nucleotides.
Requires the target sequence UH immediately 5' of the cleavage site.
Binds a variable number nucleotides on both sides of the cleavage site.
14 known members of this class. Found in a number of plant pathogens (virusoids) that use RNA as the infectious agent (FIG. 1)

Hairpin Ribozyme

Figure 3:
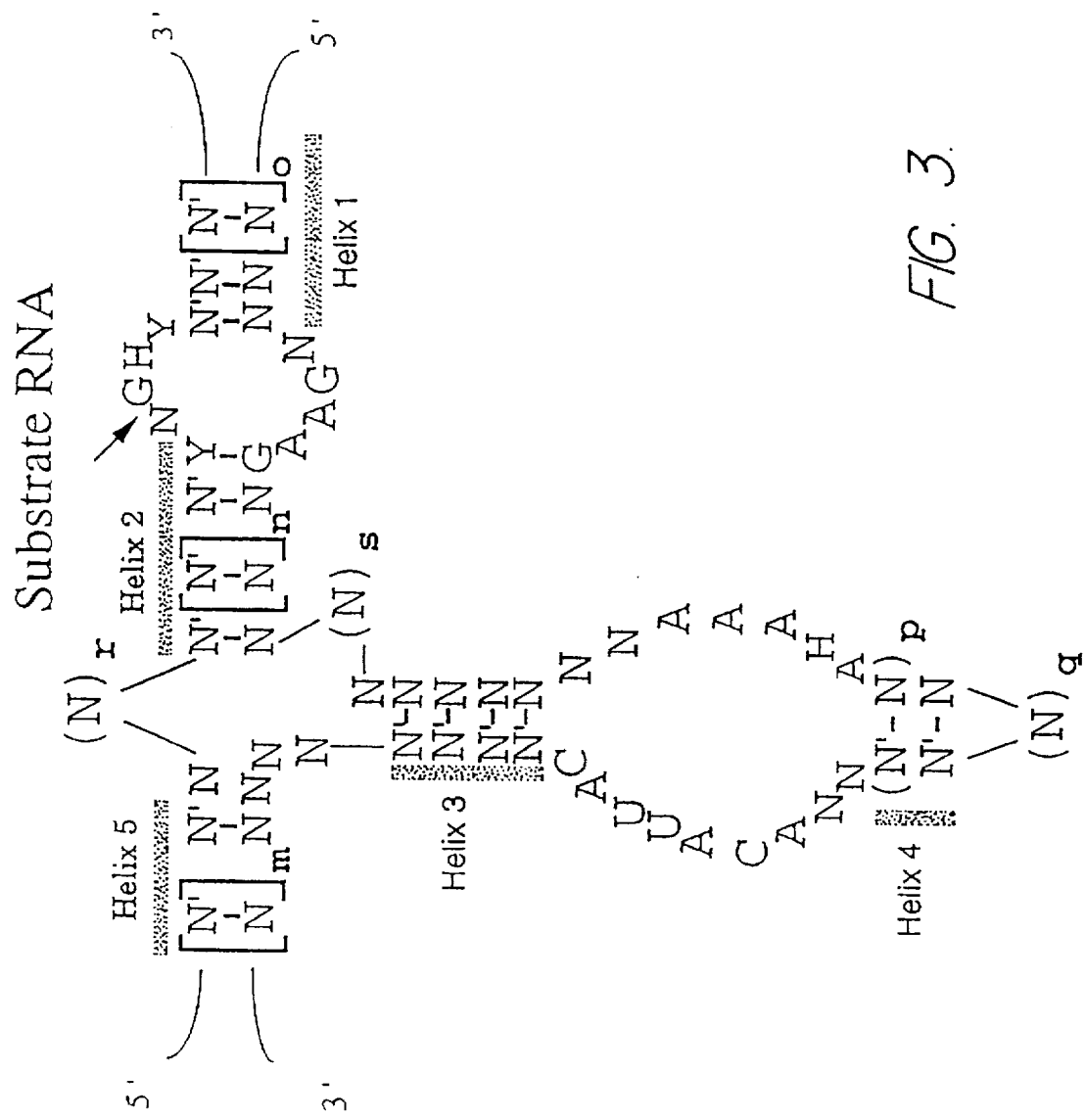

Size: ~50 nucleotides.
Requires the target sequence GUC immediately 3' of the cleavage site.
Binds 4-6 nucleotides at 5' side of the cleavage site and a variable number to the 3' side of the cleavage site.
Only 3 known member of this class. Found in three plant pathogen (satellite RNAs of the tobacco ringspot virus, arabis mosaic virus and chicory yellow mottle virus) which uses RNA as the infectious agent (FIG. 3).

Hepatitis Delta Virus (HDV) Riboxyme

Figure 4:
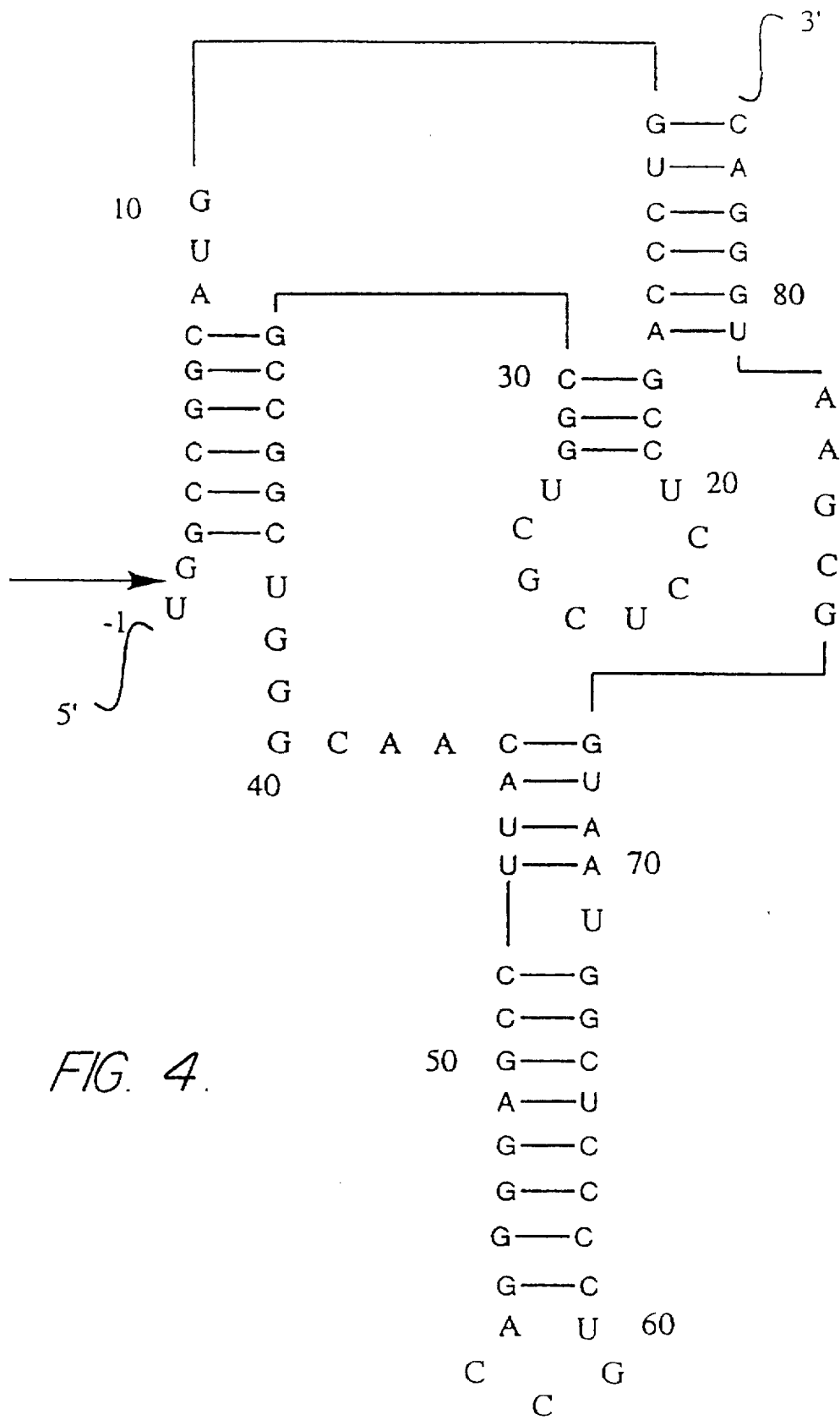
FIG. 4 is a representation of the general structure of the hepatitis delta virus ribozyme domain known in the art.

Size: 50-60 nucleotides (at present).
Cleavage of target RNAs recently demonstrated.
Sequence requirements not fully determined.
Binding sites and structural requirements not fully determined, although no sequence 5' of cleavage sit are required.
Only 1 known member of this class. Found in human HDV (FIG. 4).

Neurospora VS RNA Ribozyme

Figure 5:
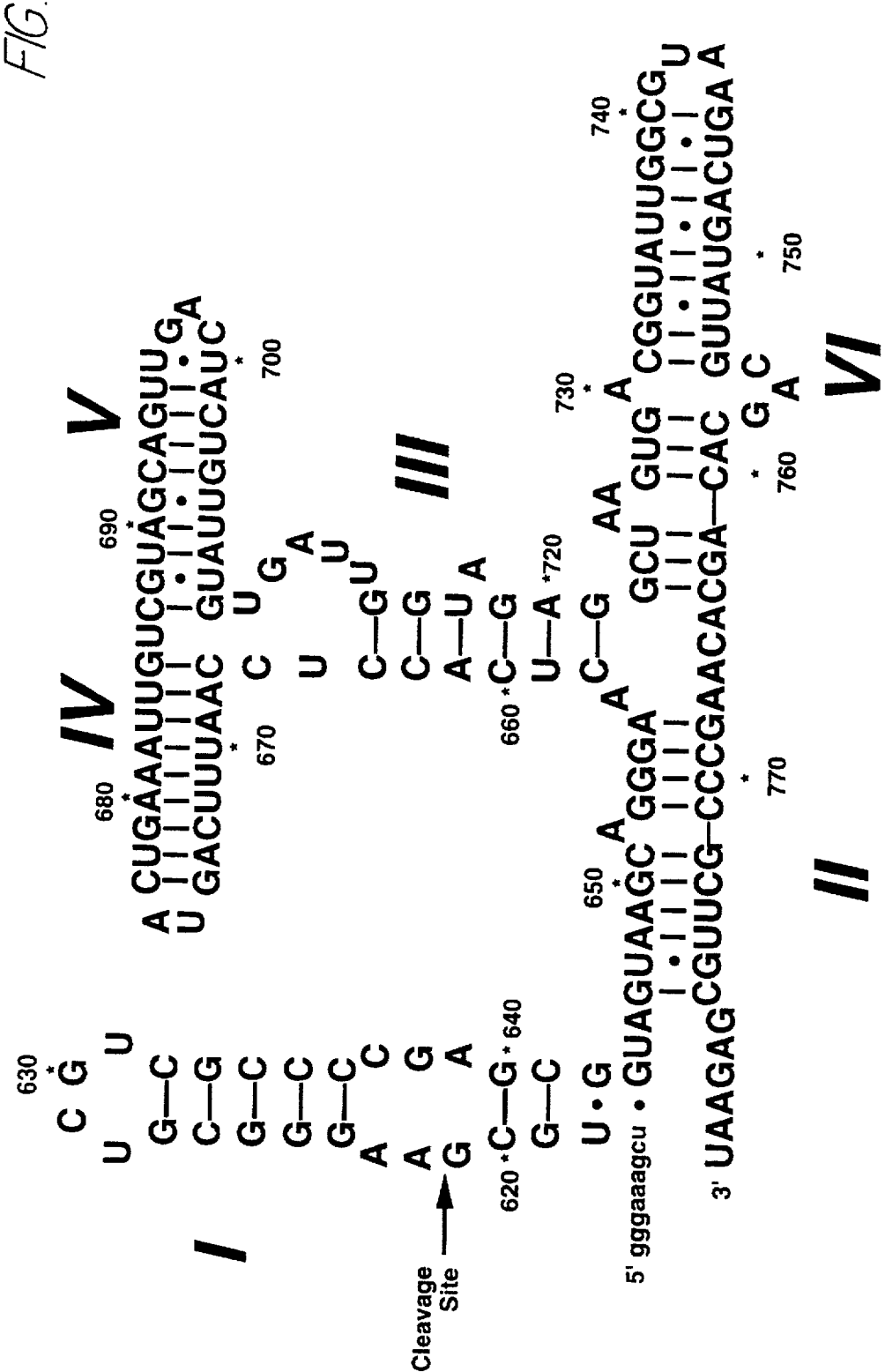
FIG. 5 is a representation of the general structure of the self-cleaving VS RNA ribozyme domain.

Size: ~144 nucleotides (at present)
Cleavage of target RNAs recently demonstrated.
Sequence requirements not fully determined.
Binding sites and structural requirements not fully determined. Only 1 known member of this class. Found in Neurospora VS RNA (FIG. 5).

TABLE II

Human CETP HH Target Sequence

| nt. Position | Target Sequence | Sequence ID No. |
|---|---|---|
| 9 | UGAAUCU C UGGGGCC | 2 |
| 45 | AGAGCCU C AUGUUCC | 3 |
| 50 | CUCAUGU U CCGUGGG | 4 |
| 51 | UCAUGUU C CGUGGGG | 5 |
| 72 | CGGACAU A CAUAUAC | 6 |
| 76 | CAUACAU A UACGGGC | 7 |
| 78 | UACAUAU A CGGGCUC | 8 |
| 85 | ACGGGCU C CAGGCUG | 9 |
| 100 | AACGGCU C GGGCCAC | 10 |
| 109 | GGCCACU U ACACACC | 11 |
| 110 | GCCACUU A CACACCA | 12 |
| 127 | GCCUGAU A ACCAUGC | 13 |
| 148 | CCACAGU C CUGACCC | 14 |
| 186 | GCCUGCU C CAAAGGC | 15 |
| 198 | GGCACCU C GCACGAG | 16 |
| 214 | CAGGCAU C GUGUGCC | 17 |
| 226 | GCCGCAU C ACCAAGC | 18 |
| 241 | CUGCCCU C CUGGUGU | 19 |
| 249 | CUGGUGU U GAACCAC | 20 |
| 274 | AGGUGAU C CAGACCG | 21 |
| 285 | ACCGCCU U CCAGCGA | 22 |
| 286 | CCGCCUU C CAGCGAG | 23 |
| 300 | GCCAGCU A CCCAGAU | 24 |
| 308 | CCCAGAU A UCACGGG | 25 |
| 310 | CAGAUAU C ACGGGCG | 26 |
| 334 | UGAUGCU C CUUGGCC | 27 |
| 337 | UGCUCCU U GGCCAAG | 28 |
| 346 | GCCAAGU C AAGUAUG | 29 |
| 351 | GUCAAGU A UGGGUUG | 30 |
| 357 | UAUGGGU U GCACAAC | 31 |
| 367 | ACAACAU C CAGAUCA | 32 |
| 373 | UCCAGAU C AGCCACU | 33 |
| 381 | AGCCACU U GUCCAUC | 34 |
| 384 | CACUUGU C CAUCGCC | 35 |
| 388 | UGUCCAU C GCCAGCA | 36 |
| 423 | GCCAAGU C CAUUGAU | 37 |
| 427 | AGUCCAU U GAUGUCU | 38 |
| 433 | UUGAUGU C UCCAUUC | 39 |
| 435 | GAUGUCU C CAUUCAG | 40 |
| 439 | UCUCCAU U CAGAACG | 41 |
| 440 | CUCCAUU C AGAACGU | 42 |
| 450 | AACGUGU C UGUGGUC | 43 |
| 457 | CUGUGGU U UUCAAGG | 44 |
| 459 | GUGGUCU U CAAGGGG | 45 |
| 460 | UGGUCUU C AAGGGGA | 46 |
| 477 | CUGAAGU A UGGCUAC | 47 |
| 483 | UAUGGCU A CACCACU | 48 |
| 506 | GCUGGGU A UUGAUCA | 49 |
| 508 | UGGGUAU U GAUCAGU | 50 |
| 512 | UAUUGAU C AGUCCAU | 51 |
| 516 | GAUCAGU C CAUUGAC | 52 |
| 520 | AGUCCAU U GACUUCG | 53 |
| 525 | AUUGACU U CGAGAUC | 54 |
| 526 | UUGACUU C GAGAUCG | 55 |
| 532 | UCGAGAU C GACUCUG | 56 |
| 537 | AUCGACU C UGCCAUU | 57 |
| 544 | CUGCCAU U GACCUCC | 58 |
| 550 | UUGACCU C CAGAUCA | 59 |
| 556 | UCCAGAU C AACACAC | 60 |
| 579 | UGUGACU C UGGUAGA | 61 |
| 584 | CUCUGGU A GAGUGCG | 62 |
| 612 | GACUGCU A CCUGUCU | 63 |
| 618 | UACCUGU C UUUCCAU | 64 |
| 620 | CCUGUCU U UCCAUAA | 65 |
| 621 | CUGUCUU U CCAUAAG | 66 |
| 622 | UGUCUUU C CAUAAGC | 67 |
| 626 | UUUCCAU A AGCUGCU | 68 |
| 634 | AGCUGCU C CUGCAUC | 69 |
| 641 | CCUGCAU C UCCAAGG | 70 |
| 643 | UGCAUCU C CAAGGGG | 71 |
| 670 | GGUGGAU C AAGCAGC | 72 |
| 681 | CAGCUGU U CACAAAU | 73 |
| 682 | AGCUGUU C ACAAAUU | 74 |
| 689 | CACAAAU U UCAUCUC | 75 |

TABLE II-continued

Human CETP HH Target Sequence

| nt. Position | Target Sequence | Sequence ID No. |
|---|---|---|
| 690 | ACAAAUU U CAUCUCC | 76 |
| 691 | CAAAUUU C AUCUCCU | 77 |
| 694 | AUUUCAU U UCCUUCA | 78 |
| 696 | UUCAUCU C CUUCACC | 79 |
| 699 | AUCUCCU U CACCCUG | 80 |
| 700 | UCUCCUU C ACCCUGA | 81 |
| 715 | AGCUGGU C CUGAAGG | 82 |
| 730 | GACAGAU C UGCAAAG | 83 |
| 742 | AAGAGAU C AACGUCA | 84 |
| 748 | UCAACGU C AUCUCUA | 85 |
| 751 | ACGUCAU C UCUAACA | 86 |
| 753 | GUCAUCU C UAACAUC | 87 |
| 755 | CAUCUCU A ACAUCAU | 88 |
| 760 | CUAACAU C AUGGCCG | 89 |
| 770 | GGCCGAU U UGUCCA | 90 |
| 771 | GCCGAUU U GUCCAG | 91 |
| 772 | CCGAUUU U GUCCAGA | 92 |
| 775 | AUUUGU C CAGACAA | 93 |
| 796 | CCAGCAU C CUUUCAG | 94 |
| 799 | GCAUCCU U UCAGAUG | 95 |
| 800 | CAUCCUU U CAGAUGG | 96 |
| 801 | AUCCUUU C AGAUGGA | 97 |
| 814 | GAGACAU U GGGGUGG | 98 |
| 826 | UGGACAU U UCCCUGA | 99 |
| 827 | GGACAUU U CCCUGAC | 100 |
| 828 | GACAUUU C CCUGACA | 101 |
| 842 | AGGUGAU C UCAGAGG | 102 |
| 847 | AUCCCGU C AUCACAG | 103 |
| 850 | CCGUCAU C ACAGCCU | 104 |
| 858 | ACAGCCU C CUACCUG | 105 |
| 861 | GCCUCCU A CCUGGAG | 106 |
| 870 | CUGGAGU C CCAUCAC | 107 |
| 875 | GUCCCAU C ACAAGGG | 108 |
| 884 | CAAGGGU C AUUUCAU | 109 |
| 887 | GGGUCAU U UCAUCUA | 110 |
| 888 | GGUCAUU U CAUCUAC | 111 |
| 889 | GUCAUUU C AUCUACA | 112 |
| 892 | AUUUCAU C UACAAGA | 113 |
| 894 | UUCAUCU A CAAGAAU | 114 |
| 904 | AGAAUGU C UCAGAGG | 115 |
| 906 | AAUGUCU C AGAGGAC | 116 |
| 916 | AGGACCU C CCCCUCC | 117 |
| 922 | UCCCCCU C CCCACCU | 118 |
| 930 | CCCACCU U CUCGCCC | 119 |
| 931 | CCACCUU C UCGCCCA | 120 |
| 933 | ACCUUCU C GCCCACA | 121 |
| 954 | GGGGACU C CCGCAUG | 122 |
| 966 | AUGCUGU A CUUCUGG | 123 |
| 969 | CUGUACU U CUGGUUC | 124 |
| 970 | UGUACUU C UGGUUCU | 125 |
| 975 | UUCUGGU U CUCUGAG | 126 |
| 976 | UCUGGUU C UCUGAGC | 127 |
| 978 | UGGUUCU C UGAGCGA | 128 |
| 988 | AGCGAGU C UUCCACU | 129 |
| 990 | CGAGUCU U CCACUCG | 130 |
| 991 | GAGUCUU C CACUCGC | 131 |
| 996 | UUCCACU C GCUGGCC | 132 |
| 1009 | CCAAGGU A GCUUUCC | 133 |
| 1013 | GGUAGCU U UCCAGGA | 134 |
| 1014 | GUAGCUU U CCAGGAU | 135 |
| 1015 | UAGCUUU C CAGGAUG | 136 |
| 1030 | GCCGCCU C AUGCUCA | 137 |
| 1036 | UCAUGCU C AGCCUGA | 138 |
| 1056 | GACGAGU U CAAGGCA | 139 |
| 1057 | ACGAGUU C AAGGCAG | 140 |
| 1083 | UGGGGCU U CAACACC | 141 |
| 1084 | GGGGCUU C AACACCA | 142 |
| 1102 | AGGAAAU C UUCCAAG | 143 |
| 1104 | GAAAUCU U CCAAGAG | 144 |
| 1105 | AAAUCUU C CAAGAGG | 145 |
| 1114 | AAGAGGU U GUCGGCG | 146 |
| 1117 | AGGUUGU C GGCGGCU | 147 |
| 1125 | GGCGGCU U CCCCAGC | 148 |
| 1126 | GCGGCUU C CCCAGCC | 149 |
| 1144 | CCCAAGU C ACCGUCC | 150 |
| 1150 | UCACCGU C CACUGCC | 151 |
| 1159 | ACUGCCU C AAGAUGC | 152 |
| 1174 | CCAAGAU C UCCUGCC | 153 |
| 1176 | AAGAUCU C CUGCCAA | 154 |
| 1195 | AGGGAGU C GUGGUCA | 155 |
| 1201 | UCGUGGU C AAUUCUU | 156 |
| 1205 | GGUCAAU U CUUCAGU | 157 |
| 1206 | GUCAAUU C UUCAGUG | 158 |
| 1208 | CAAUUCU U CAGUGAU | 159 |
| 1209 | AAUUCUU C AGUGAUG | 160 |
| 1224 | GUGAAAU U CCUCUUU | 161 |
| 1225 | UGAAAUU C CUCUUUC | 162 |
| 1228 | AAUUCCU C UUUCCAC | 163 |
| 1230 | UUCCUCU U UCCACGC | 164 |
| 1231 | UCCUCUU U CCACGCC | 165 |
| 1232 | CCUCUUU C CACGCCC | 166 |
| 1253 | GCAACAU U CUGUAGC | 167 |
| 1254 | CAACAUU C UGUAGCU | 168 |
| 1258 | AUUCUGU A GCUUACA | 169 |
| 1262 | UGUAGCU U ACACAUU | 170 |
| 1263 | GUAGCUU A CACAUUU | 171 |
| 1269 | UACACAU U UGAAGAG | 172 |
| 1270 | ACACAUU U GAAGAGG | 173 |
| 1280 | AGAGGAU A UCGUGAC | 174 |
| 1282 | AGGAUAU C GUGACUA | 175 |
| 1289 | CGUGACU A CCGUCCA | 176 |
| 1294 | CUACCGU C CAGGCCU | 177 |
| 1302 | CAGGCCU C CUAUUCU | 178 |
| 1305 | GCCUCCU A UUCUAAG | 179 |
| 1307 | CUCCUAU U CUAAGAA | 180 |
| 1308 | UCCUAUU C UAAGAAA | 181 |
| 1310 | CUAUUCU A AGAAAAA | 182 |
| 1321 | AAAAGCU C UUCUUAA | 183 |
| 1323 | AAGCUCU U CUUAAGC | 184 |
| 1324 | AGCUCUU C UUAAGCC | 185 |
| 1326 | CUCUUCU U AAGCCUC | 186 |
| 1327 | UCUUCUU A AGCCUCU | 187 |
| 1333 | UAAGCCU C UUGGAUU | 188 |
| 1335 | AGCCUCU U GGAUUUC | 189 |
| 1340 | CUUGGAU U UCCAGAU | 190 |
| 1341 | UUGGAUU U CCAGAUU | 191 |
| 1342 | UGGAUUU C CAGAUUA | 192 |
| 1348 | UCCAGAU U ACACCAA | 193 |
| 1349 | CCAGAUU A CACCAAA | 194 |
| 1363 | AGACUGU U UCCAACU | 195 |
| 1364 | GACUGUU U CCAACUU | 196 |
| 1365 | ACUGUUU C CAACUUG | 197 |
| 1371 | UCCAACU U GACUGAG | 198 |
| 1386 | AGCAGCU C CGAGUCC | 199 |
| 1392 | UCCGAGU C CAUCCAG | 200 |
| 1396 | AGUCCAU C CAGAGCU | 201 |
| 1404 | CAGAGCU U CCUGCAG | 202 |
| 1405 | AGAGCUU C CUGCAGU | 203 |
| 1413 | CUGCAGU C AAUGAUC | 204 |
| 1420 | CAAUGAU C ACCGCUG | 205 |
| 1435 | UGGGCAU U CCUGAGG | 206 |
| 1444 | CUGAGGU C AUGUCUC | 207 |
| 1449 | GUCAUGU C UCGGCUC | 208 |
| 1451 | CAUGUCU C GGCUCGA | 209 |
| 1456 | CUCGGCU C GAGGUAG | 210 |
| 1462 | UCGAGGU A GUGUUUA | 211 |
| 1467 | GUAGUGU U UACAGCC | 212 |
| 1468 | UAGUGUU U ACAGCCC | 213 |
| 1469 | AGUGUUU A CAGCCCU | 214 |
| 1477 | CAGCCCU C AUGAACA | 215 |
| 1501 | UGAGCCU C UUCGACA | 216 |
| 1503 | AGCCUCU U CGACAUC | 217 |
| 1504 | GCCUCUU C GACAUCA | 218 |
| 1510 | UCGACAU C AUCAACC | 219 |
| 1513 | ACAUCAU C AACCCUG | 220 |
| 1525 | CUGAGAU U AUCACUC | 221 |
| 1526 | UGAGAUU A UCACUCG | 222 |
| 1528 | AGAUUAU C ACUCGAG | 223 |

TABLE II-continued

Human CETP HH Target Sequence

| nt. Position | Target Sequence | Sequence ID No. |
|---|---|---|
| 1532 | UAUCACU C GAGAUGG | 224 |
| 1542 | GAUGGCU U CCUGCUG | 225 |
| 1543 | AUGGCUU C CUGCUGC | 226 |
| 1563 | AUGGACU U UGGCUUC | 227 |
| 1564 | UGGACUU U GGCUUCC | 228 |
| 1569 | UUUGGCU U CCCUGAG | 229 |
| 1570 | UUGGCUU C CCUGAGC | 230 |
| 1592 | GGUGGAU U UCCUCCA | 231 |
| 1593 | GUGGAUU U CCUCCAG | 232 |
| 1594 | UGGAUUU C CUCCAGA | 233 |
| 1597 | AUUUCCU C CAGAGCU | 234 |
| 1605 | CAGAGCU U GAGCUAG | 235 |
| 1611 | UUGAGCU A GAAGUCU | 236 |
| 1617 | UAGAAGU C UCCAAGG | 237 |
| 1619 | GAAGUCU C CAAGGAG | 238 |
| 1629 | AGGAGGU C GGGAUGG | 239 |
| 1641 | UGGGGCU U GUAGCAG | 240 |
| 1644 | GGCUUGU A GCAGAAG | 241 |
| 1666 | CCAGGCU C ACAGCUG | 242 |
| 1686 | CUGGUGU C UCCUCCA | 243 |
| 1688 | GGUGUCU C CUCCAGC | 244 |
| 1691 | GUCUCCU C CAGCGUG | 245 |
| 1707 | UGGAAGU U GGGUUAG | 246 |
| 1712 | GUUGGGU U AGGAGUA | 247 |
| 1713 | UUGGGUU A GGAGUAC | 248 |
| 1719 | UAGGAGU A CGGAGAU | 249 |
| 1733 | UGGAGAU U GGCUCCC | 250 |
| 1738 | AUUGGCU C CCAACUC | 251 |
| 1745 | CCCAACU C CUCCCUA | 252 |
| 1748 | AACUCCU C CCUAUCC | 253 |
| 1752 | CCUCCCU A UCCUAAA | 254 |
| 1754 | UCCCUAU C CUAAAGG | 255 |
| 1757 | CUAUCCU A AAGGCCC | 256 |
| 1773 | CUGGCAU U AAAGUGC | 257 |
| 1774 | UGGCAUU A AAGUGCU | 258 |

TABLE III

Human CETP HH Ribozyme Sequence

| nt. Position | HH Ribozyme Sequence | Sequence ID No. |
|---|---|---|
| 9 | GGCCCCA CUGAUGAGGCCGAAAGGCCGAA AGAUUCA | 259 |
| 45 | GGAACAU CUGAUGAGGCCGAAAGGCCGAA AGGCUCU | 260 |
| 50 | CCCACGG CUGAUGAGGCCGAAAGGCCGAA ACAUGAG | 261 |
| 51 | CCCCACG CUGAUGAGGCCGAAAGGCCGAA AACAUGA | 262 |
| 72 | GUAUAUG CUGAUGAGGCCGAAAGGCCGAA AUGUCCG | 263 |
| 76 | GCCCGUA CUGAUGAGGCCGAAAGGCCGAA AUGUAUG | 264 |
| 78 | GAGCCCG CUGAUGAGGCCGAAAGGCCGAA AUAUGUA | 265 |
| 85 | CAGCCUG CUGAUGAGGCCGAAAGGCCGAA AGCCCGU | 266 |
| 100 | GUGGCCC CUGAUGAGGCCGAAAGGCCGAA AGCCGUU | 267 |
| 109 | GGUGUGU CUGAUGAGGCCGAAAGGCCGAA AGUGGCC | 268 |
| 110 | UGGUGUG CUGAUGAGGCCGAAAGGCCGAA AAGUGGC | 269 |
| 127 | GCAUGGU CUGAUGAGGCCGAAAGGCCGAA AUCAGGC | 270 |
| 148 | GGGUCAG CUGAUGAGGCCGAAAGGCCGAA ACUGUGG | 271 |
| 186 | GCCUUUG CUGAUGAGGCCGAAAGGCCGAA AGCAGGC | 272 |
| 198 | CUCGUGC CUGAUGAGGCCGAAAGGCCGAA AGGUGCC | 273 |
| 214 | GGCACAC CUGAUGAGGCCGAAAGGCCGAA AUGCCUG | 274 |
| 226 | GCUUGGU CUGAUGAGGCCGAAAGGCCGAA AUGCGGC | 275 |
| 241 | ACACCAG CUGAUGAGGCCGAAAGGCCGAA AGGGCAG | 276 |
| 249 | GUGGUUC CUGAUGAGGCCGAAAGGCCGAA ACACCAG | 277 |
| 274 | CGGUCUG CUGAUGAGGCCGAAAGGCCGAA AUCACCU | 278 |
| 285 | UCGCUGG CUGAUGAGGCCGAAAGGCCGAA AGGCGGU | 279 |
| 286 | CUCGCUG CUGAUGAGGCCGAAAGGCCGAA AAGGCGG | 280 |
| 300 | AUCUGGG CUGAUGAGGCCGAAAGGCCGAA AGCUGGC | 281 |
| 308 | CCCGUGA CUGAUGAGGCCGAAAGGCCGAA AUCUGGG | 282 |
| 310 | CGCCCGU CUGAUGAGGCCGAAAGGCCGAA AUAUCUG | 283 |
| 334 | GGCCAAG CUGAUGAGGCCGAAAGGCCGAA AGCAUCA | 284 |
| 337 | CUUGGCC CUGAUGAGGCCGAAAGGCCGAA AGGAGCA | 285 |
| 346 | CAUACUU CUGAUGAGGCCGAAAGGCCGAA ACUUGGC | 286 |
| 351 | CAACCCA CUGAUGAGGCCGAAAGGCCGAA ACUUGAC | 287 |
| 357 | GUUGUGC CUGAUGAGGCCGAAAGGCCGAA ACCCAUA | 288 |
| 367 | UGAUCUG CUGAUGAGGCCGAAAGGCCGAA AUGUUGU | 289 |
| 373 | AGUGGCU CUGAUGAGGCCGAAAGGCCGAA AUCUGGA | 290 |

TABLE III-continued

Human CETP HH Ribozyme Sequence

| nt. Position | HH Ribozyme Sequence | Sequence ID No. |
|---|---|---|
| 381 | GAUGGAC CUGAUGAGGCCGAAAGGCCGAA AGUGGCU | 291 |
| 384 | GGCGAUG CUGAUGAGGCCGAAAGGCCGAA ACAAGUG | 292 |
| 388 | UGCUGGC CUGAUGAGGCCGAAAGGCCGAA AUGGACA | 293 |
| 423 | AUCAAUG CUGAUGAGGCCGAAAGGCCGAA ACUUGGC | 294 |
| 427 | AGACAUC CUGAUGAGGCCGAAAGGCCGAA AUGGACU | 295 |
| 433 | GAAUGGA CUGAUGAGGCCGAAAGGCCGAA ACAUCAA | 296 |
| 435 | CUGAAUG CUGAUGAGGCCGAAAGGCCGAA AGACAUC | 297 |
| 439 | CGUUCUG CUGAUGAGGCCGAAAGGCCGAA AUGGAGA | 298 |
| 440 | ACGUUCU CUGAUGAGGCCGAAAGGCCGAA AAUGGAG | 299 |
| 450 | GACCACA CUGAUGAGGCCGAAAGGCCGAA ACACGUU | 300 |
| 457 | CCUUGAA CUGAUGAGGCCGAAAGGCCGAA ACCACAG | 301 |
| 459 | CCCCUUG CUGAUGAGGCCGAAAGGCCGAA AGACCAC | 302 |
| 460 | UCCCCUU CUGAUGAGGCCGAAAGGCCGAA AAGACCA | 303 |
| 477 | GUAGCCA CUGAUGAGGCCGAAAGGCCGAA ACUUCAG | 304 |
| 483 | AGUGGUG CUGAUGAGGCCGAAAGGCCGAA AGCCAUA | 305 |
| 506 | UGAUCAA CUGAUGAGGCCGAAAGGCCGAA ACCCAGC | 306 |
| 508 | ACUGAUC CUGAUGAGGCCGAAAGGCCGAA AUACCCA | 307 |
| 512 | AUGGACU CUGAUGAGGCCGAAAGGCCGAA AUCAAUA | 308 |
| 516 | GUCAAUG CUGAUGAGGCCGAAAGGCCGAA ACUGAUC | 309 |
| 520 | CGAAGUC CUGAUGAGGCCGAAAGGCCGAA AUGGACU | 310 |
| 525 | GAUCUCG CUGAUGAGGCCGAAAGGCCGAA AGUCAAU | 311 |
| 526 | CGAUCUC CUGAUGAGGCCGAAAGGCCGAA AAGUCAA | 312 |
| 532 | CAGAGUC CUGAUGAGGCCGAAAGGCCGAA AUCUCGA | 313 |
| 537 | AAUGGCA CUGAUGAGGCCGAAAGGCCGAA AGUCGAU | 314 |
| 544 | GGAGGUC CUGAUGAGGCCGAAAGGCCGAA AUGGCAG | 315 |
| 550 | UGAUCUG CUGAUGAGGCCGAAAGGCCGAA AGGUCAA | 316 |
| 556 | GUGUGUU CUGAUGAGGCCGAAAGGCCGAA AUCUGGA | 317 |
| 579 | UCUACCA CUGAUGAGGCCGAAAGGCCGAA AGUCACA | 318 |
| 584 | CGCACUC CUGAUGAGGCCGAAAGGCCGAA ACCAGAG | 319 |
| 612 | AGACAGG CUGAUGAGGCCGAAAGGCCGAA AGCAGUC | 320 |
| 618 | AUGGAAA CUGAUGAGGCCGAAAGGCCGAA ACAGGUA | 321 |
| 620 | UUAUGGA CUGAUGAGGCCGAAAGGCCGAA AGACAGG | 322 |
| 621 | CUUAUGG CUGAUGAGGCCGAAAGGCCGAA AAGACAG | 323 |
| 622 | GCUUAUG CUGAUGAGGCCGAAAGGCCGAA AAAGACA | 324 |
| 626 | AGCAGCU CUGAUGAGGCCGAAAGGCCGAA AUGGAAA | 325 |
| 634 | GAUGCAG CUGAUGAGGCCGAAAGGCCGAA AGCAGCU | 326 |
| 641 | CCUUGGA CUGAUGAGGCCGAAAGGCCGAA AUGCAGG | 327 |
| 643 | CCCCUUG CUGAUGAGGCCGAAAGGCCGAA AGAUGCA | 328 |
| 670 | GCUGCUU CUGAUGAGGCCGAAAGGCCGAA AUCCACC | 329 |
| 681 | AUUUGUG CUGAUGAGGCCGAAAGGCCGAA ACAGCUG | 330 |
| 682 | AAUUUGU CUGAUGAGGCCGAAAGGCCGAA AACAGCU | 331 |
| 689 | GAGAUGA CUGAUGAGGCCGAAAGGCCGAA AUUUGUG | 332 |
| 690 | GGAGAUG CUGAUGAGGCCGAAAGGCCGAA AAUUUGU | 333 |
| 691 | AGGAGAU CUGAUGAGGCCGAAAGGCCGAA AAAUUUG | 334 |
| 694 | UGAAGGA CUGAUGAGGCCGAAAGGCCGAA AUGAAAU | 335 |
| 696 | GGUGAAG CUGAUGAGGCCGAAAGGCCGAA AGAUGAA | 336 |
| 699 | CAGGGUG CUGAUGAGGCCGAAAGGCCGAA AGGAGAU | 337 |
| 700 | UCAGGGU CUGAUGAGGCCGAAAGGCCGAA AAGGAGA | 338 |
| 715 | CCUUCAG CUGAUGAGGCCGAAAGGCCGAA ACCAGCU | 339 |
| 730 | CUUUGCA CUGAUGAGGCCGAAAGGCCGAA AUCUGUC | 340 |
| 742 | UGACGUU CUGAUGAGGCCGAAAGGCCGAA AUCUCUU | 341 |
| 748 | UAGAGAU CUGAUGAGGCCGAAAGGCCGAA ACGUUGA | 342 |
| 751 | UGUUAGA CUGAUGAGGCCGAAAGGCCGAA AUGACGU | 343 |
| 753 | GAUGUUA CUGAUGAGGCCGAAAGGCCGAA AGAUGAC | 344 |
| 755 | AUGAUGU CUGAUGAGGCCGAAAGGCCGAA AGAGAUG | 345 |
| 760 | CGGCCAU CUGAUGAGGCCGAAAGGCCGAA AUGUUAG | 346 |
| 770 | UGGACAA CUGAUGAGGCCGAAAGGCCGAA AUCGGCC | 347 |
| 771 | CUGGACA CUGAUGAGGCCGAAAGGCCGAA AAUCGGC | 348 |
| 772 | UCUGGAC CUGAUGAGGCCGAAAGGCCGAA AAAUCGG | 349 |
| 775 | UUGUCUG CUGAUGAGGCCGAAAGGCCGAA ACAAAAU | 350 |
| 796 | CUGAAAG CUGAUGAGGCCGAAAGGCCGAA AUGCUGG | 351 |
| 799 | CAUCUGA CUGAUGAGGCCGAAAGGCCGAA AGGAUGC | 352 |
| 800 | CCAUCUG CUGAUGAGGCCGAAAGGCCGAA AAGGAUG | 353 |
| 801 | UCCAUCU CUGAUGAGGCCGAAAGGCCGAA AAAGGAU | 354 |
| 814 | CCACCCC CUGAUGAGGCCGAAAGGCCGAA AUGUCUC | 355 |
| 826 | UCAGGGA CUGAUGAGGCCGAAAGGCCGAA AUGUCCA | 356 |
| 827 | GUCAGGG CUGAUGAGGCCGAAAGGCCGAA AAUGUCC | 357 |
| 828 | UGUCAGG CUGAUGAGGCCGAAAGGCCGAA AAAUGUC | 358 |
| 842 | AUGACGG CUGAUGAGGCCGAAAGGCCGAA AUCACCU | 359 |
| 847 | CUGUGAU CUGAUGAGGCCGAAAGGCCGAA ACGGGAU | 360 |
| 850 | AGGCUGU CUGAUGAGGCCGAAAGGCCGAA AUGACGG | 361 |
| 858 | CAGGUAG CUGAUGAGGCCGAAAGGCCGAA AGGCUGU | 362 |
| 861 | CUCCAGG CUGAUGAGGCCGAAAGGCCGAA AGGAGGC | 363 |
| 870 | GUGAUGG CUGAUGAGGCCGAAAGGCCGAA ACUCCAG | 364 |

TABLE III-continued

Human CETP HH Ribozyme Sequence

| nt. Position | HH Ribozyme Sequence | Sequence ID No. |
|---|---|---|
| 875 | CCCUUGU CUGAUGAGGCCGAAAGGCCGAA AUGGGAC | 365 |
| 884 | AUGAAAU CUGAUGAGGCCGAAAGGCCGAA ACCCUUG | 366 |
| 887 | UAGAUGA CUGAUGAGGCCGAAAGGCCGAA AUGACCC | 367 |
| 888 | GUAGAUG CUGAUGAGGCCGAAAGGCCGAA AAUGACC | 368 |
| 889 | UGUAGAU CUGAUGAGGCCGAAAGGCCGAA AAAUGAC | 369 |
| 892 | UCUUGUA CUGAUGAGGCCGAAAGGCCGAA AUGAAAU | 370 |
| 894 | AUUCUUG CUGAUGAGGCCGAAAGGCCGAA AGAUGAA | 371 |
| 904 | CCUCUGA CUGAUGAGGCCGAAAGGCCGAA ACAUUCU | 372 |
| 906 | GUCCUCU CUGAUGAGGCCGAAAGGCCGAA AGACAUU | 373 |
| 916 | GGAGGGG CUGAUGAGGCCGAAAGGCCGAA AGGUCCU | 374 |
| 922 | AGGUGGG CUGAUGAGGCCGAAAGGCCGAA AGGGGGA | 375 |
| 930 | GGGCGAG CUGAUGAGGCCGAAAGGCCGAA AGGUGGG | 376 |
| 931 | UGGGCGA CUGAUGAGGCCGAAAGGCCGAA AAGGUGG | 377 |
| 933 | UGUGGGC CUGAUGAGGCCGAAAGGCCGAA AGAAGGU | 378 |
| 954 | CAUGCGG CUGAUGAGGCCGAAAGGCCGAA AGUCCCC | 379 |
| 966 | CCAGAAG CUGAUGAGGCCGAAAGGCCGAA ACAGCAU | 380 |
| 969 | GAACCAG CUGAUGAGGCCGAAAGGCCGAA AGUACAG | 381 |
| 970 | AGAACCA CUGAUGAGGCCGAAAGGCCGAA AAGUACA | 382 |
| 975 | CUCAGAG CUGAUGAGGCCGAAAGGCCGAA ACCAGAA | 383 |
| 976 | GCUCAGA CUGAUGAGGCCGAAAGGCCGAA AACCAGA | 384 |
| 978 | UCGCUCA CUGAUGAGGCCGAAAGGCCGAA AGAACCA | 385 |
| 988 | AGUGGAA CUGAUGAGGCCGAAAGGCCGAA ACUCGCU | 386 |
| 990 | CGAGUGG CUGAUGAGGCCGAAAGGCCGAA AGACUCG | 387 |
| 991 | GCGAGUG CUGAUGAGGCCGAAAGGCCGAA AAGACUC | 388 |
| 996 | GGCCAGC CUGAUGAGGCCGAAAGGCCGAA AGUGGAA | 389 |
| 1009 | GGAAAGC CUGAUGAGGCCGAAAGGCCGAA ACCUUGG | 390 |
| 1013 | UCCUGGA CUGAUGAGGCCGAAAGGCCGAA AGCUACC | 391 |
| 1014 | AUCCUGG CUGAUGAGGCCGAAAGGCCGAA AAGCUAC | 392 |
| 1015 | CAUCCUG CUGAUGAGGCCGAAAGGCCGAA AAAGCUA | 393 |
| 1030 | UGAGCAU CUGAUGAGGCCGAAAGGCCGAA AGGCGGC | 394 |
| 1036 | UCAGGCU CUGAUGAGGCCGAAAGGCCGAA AGCAUGA | 395 |
| 1056 | UGCCUUG CUGAUGAGGCCGAAAGGCCGAA ACUCGUC | 396 |
| 1057 | CUGCCUU CUGAUGAGGCCGAAAGGCCGAA AACUCGU | 397 |
| 1083 | GGUGUUG CUGAUGAGGCCGAAAGGCCGAA AGCCCCA | 398 |
| 1084 | UGGUGUU CUGAUGAGGCCGAAAGGCCGAA AAGCCCC | 399 |
| 1102 | CUUGGAA CUGAUGAGGCCGAAAGGCCGAA AUUUCCU | 400 |
| 1104 | CUCUUGG CUGAUGAGGCCGAAAGGCCGAA AGAUUUC | 401 |
| 1105 | CCUCUUG CUGAUGAGGCCGAAAGGCCGAA AAGAUUU | 402 |
| 1114 | CGCCGAC CUGAUGAGGCCGAAAGGCCGAA ACCUCUU | 403 |
| 1117 | AGCCGCC CUGAUGAGGCCGAAAGGCCGAA ACAACCU | 404 |
| 1125 | GCUGGGG CUGAUGAGGCCGAAAGGCCGAA AGCCGCC | 405 |
| 1126 | GGCUGGG CUGAUGAGGCCGAAAGGCCGAA AAGCCGC | 406 |
| 1144 | GGACGGU CUGAUGAGGCCGAAAGGCCGAA ACUUGGG | 407 |
| 1150 | GGCAGUG CUGAUGAGGCCGAAAGGCCGAA ACGGUGA | 408 |
| 1159 | GCAUCUU CUGAUGAGGCCGAAAGGCCGAA AGGCAGU | 409 |
| 1174 | GGCAGGA CUGAUGAGGCCGAAAGGCCGAA AUCUUGG | 410 |
| 1176 | UUGGCAG CUGAUGAGGCCGAAAGGCCGAA AGAUCUU | 411 |
| 1195 | UGACCAC CUGAUGAGGCCGAAAGGCCGAA ACUCCCU | 412 |
| 1201 | AAGAAUU CUGAUGAGGCCGAAAGGCCGAA ACCACGA | 413 |
| 1205 | ACUGAAG CUGAUGAGGCCGAAAGGCCGAA AUUGACC | 414 |
| 1206 | CACUGAA CUGAUGAGGCCGAAAGGCCGAA AAUUGAC | 415 |
| 1208 | AUCACUG CUGAUGAGGCCGAAAGGCCGAA AGAAUUG | 416 |
| 1209 | CAUCACU CUGAUGAGGCCGAAAGGCCGAA AAGAAUU | 417 |
| 1224 | AAAGAGG CUGAUGAGGCCGAAAGGCCGAA AUUUCAC | 418 |
| 1225 | GAAAGAG CUGAUGAGGCCGAAAGGCCGAA AAUUUCA | 419 |
| 1228 | GUGGAAA CUGAUGAGGCCGAAAGGCCGAA AGGAAUU | 420 |
| 1230 | GCGUGGA CUGAUGAGGCCGAAAGGCCGAA AGAGGAA | 421 |
| 1231 | GGCGUGG CUGAUGAGGCCGAAAGGCCGAA AAGAGGA | 422 |
| 1232 | GGGCGUG CUGAUGAGGCCGAAAGGCCGAA AAAGAGG | 423 |
| 1253 | GCUACAG CUGAUGAGGCCGAAAGGCCGAA AUGUUGC | 424 |
| 1254 | AGCUACA CUGAUGAGGCCGAAAGGCCGAA AAUGUUG | 425 |
| 1258 | AGUAAGC CUGAUGAGGCCGAAAGGCCGAA ACAGAAU | 426 |
| 1262 | AAUGUGU CUGAUGAGGCCGAAAGGCCGAA AGCUACA | 427 |
| 1263 | AAAUGUG CUGAUGAGGCCGAAAGGCCGAA AAGCUAC | 428 |
| 1269 | CUCUUCA CUGAUGAGGCCGAAAGGCCGAA AUGUGUA | 429 |
| 1270 | CCUCUUC CUGAUGAGGCCGAAAGGCCGAA AAUGUGU | 430 |
| 1280 | GUCACGA CUGAUGAGGCCGAAAGGCCGAA AUCCUCU | 431 |
| 1282 | UAGUCAC CUGAUGAGGCCGAAAGGCCGAA AUAUCCU | 432 |
| 1289 | UGGACGG CUGAUGAGGCCGAAAGGCCGAA AGUCACG | 433 |
| 1294 | AGGCCUG CUGAUGAGGCCGAAAGGCCGAA ACGGUAG | 434 |
| 1302 | AGAAUAG CUGAUGAGGCCGAAAGGCCGAA AGGCCUG | 435 |
| 1305 | CUUAGAA CUGAUGAGGCCGAAAGGCCGAA AGGAGGC | 436 |
| 1307 | UUCUUAG CUGAUGAGGCCGAAAGGCCGAA AUAGGAG | 437 |
| 1308 | UUUCUUA CUGAUGAGGCCGAAAGGCCGAA AAUAGGA | 438 |

TABLE III-continued

Human CETP HH Ribozyme Sequence

| nt. Position | HH Ribozyme Sequence | Sequence ID No. |
|---|---|---|
| 1310 | UUUUUCU CUGAUGAGGCCGAAAGGCCGAA AGAAUAG | 439 |
| 1321 | UUAAGAA CUGAUGAGGCCGAAAGGCCGAA AGCUUUU | 440 |
| 1323 | GCUUAAG CUGAUGAGGCCGAAAGGCCGAA AGAGCUU | 441 |
| 1324 | GGCUUAA CUGAUGAGGCCGAAAGGCCGAA AAGAGCU | 442 |
| 1326 | GAGGCUU CUGAUGAGGCCGAAAGGCCGAA AGAAGAG | 443 |
| 1327 | AGAGGCU CUGAUGAGGCCGAAAGGCCGAA AAGAAGA | 444 |
| 1333 | AAUCCAA CUGAUGAGGCCGAAAGGCCGAA AGGCUUA | 445 |
| 1335 | GAAAUCC CUGAUGAGGCCGAAAGGCCGAA AGAGGCU | 446 |
| 1340 | AUCUGGA CUGAUGAGGCCGAAAGGCCGAA AUCCAAG | 447 |
| 1341 | AAUCUGG CUGAUGAGGCCGAAAGGCCGAA AAUCCAA | 448 |
| 1342 | UAAUCUG CUGAUGAGGCCGAAAGGCCGAA AAAUCCA | 449 |
| 1348 | UUGGUGU CUGAUGAGGCCGAAAGGCCGAA AUCUGGA | 450 |
| 1349 | UUUGGUG CUGAUGAGGCCGAAAGGCCGAA AAUCUGG | 451 |
| 1363 | AGUUGGA CUGAUGAGGCCGAAAGGCCGAA ACAGUCU | 452 |
| 1364 | AAGUUGG CUGAUGAGGCCGAAAGGCCGAA AACAGUC | 453 |
| 1365 | CAAGUUG CUGAUGAGGCCGAAAGGCCGAA AAACAGU | 454 |
| 1371 | CUCAGUC CUGAUGAGGCCGAAAGGCCGAA AGUUGGA | 455 |
| 1386 | GGACUCG CUGAUGAGGCCGAAAGGCCGAA AGCUGCU | 456 |
| 1392 | CUGGAUG CUGAUGAGGCCGAAAGGCCGAA ACUCGGA | 457 |
| 1396 | AGCUCUG CUGAUGAGGCCGAAAGGCCGAA AUGGACU | 458 |
| 1404 | CUGCAGG CUGAUGAGGCCGAAAGGCCGAA AGCUCUG | 459 |
| 1405 | ACUGCAG CUGAUGAGGCCGAAAGGCCGAA AAGCUCU | 460 |
| 1413 | GAUCAUU CUGAUGAGGCCGAAAGGCCGAA ACUGCAG | 461 |
| 1420 | CAGCGGU CUGAUGAGGCCGAAAGGCCGAA AUCAUUG | 462 |
| 1435 | CCUCAGG CUGAUGAGGCCGAAAGGCCGAA AUGCCCA | 463 |
| 1444 | GAGACAU CUGAUGAGGCCGAAAGGCCGAA ACCUCAG | 464 |
| 1449 | GAGCCGA CUGAUGAGGCCGAAAGGCCGAA ACAUGAC | 465 |
| 1451 | UCGAGCC CUGAUGAGGCCGAAAGGCCGAA AGACAUG | 466 |
| 1456 | CUACCUC CUGAUGAGGCCGAAAGGCCGAA AGCCGAG | 467 |
| 1462 | UAAACAC CUGAUGAGGCCGAAAGGCCGAA ACCUCGA | 468 |
| 1467 | GGCUGUA CUGAUGAGGCCGAAAGGCCGAA ACACUAC | 469 |
| 1468 | GGGCUGU CUGAUGAGGCCGAAAGGCCGAA AACACUA | 470 |
| 1469 | AGGGCUG CUGAUGAGGCCGAAAGGCCGAA AAACACU | 471 |
| 1477 | UGUUCAU CUGAUGAGGCCGAAAGGCCGAA AGGGCUG | 472 |
| 1501 | UGUCGAA CUGAUGAGGCCGAAAGGCCGAA AGGCUCA | 473 |
| 1503 | GAUGUCG CUGAUGAGGCCGAAAGGCCGAA AGAGGCU | 474 |
| 1504 | UGAUGUC CUGAUGAGGCCGAAAGGCCGAA AAGAGGC | 475 |
| 1510 | GGUUGAU CUGAUGAGGCCGAAAGGCCGAA AUGUCGA | 476 |
| 1513 | CAGGGUU CUGAUGAGGCCGAAAGGCCGAA AUGAUGU | 477 |
| 1525 | GAGUGAU CUGAUGAGGCCGAAAGGCCGAA AUCUCAG | 478 |
| 1526 | CGAGUGA CUGAUGAGGCCGAAAGGCCGAA AAUCUCA | 479 |
| 1528 | CUCGAGU CUGAUGAGGCCGAAAGGCCGAA AUAAUCU | 480 |
| 1532 | CCAUCUC CUGAUGAGGCCGAAAGGCCGAA AGUGAUA | 481 |
| 1542 | CAGCAGG CUGAUGAGGCCGAAAGGCCGAA AGCCAUC | 482 |
| 1543 | GCAGCAG CUGAUGAGGCCGAAAGGCCGAA AAGCCAU | 483 |
| 1563 | GAAGCCA CUGAUGAGGCCGAAAGGCCGAA AGUCCAU | 484 |
| 1564 | GGAAGCC CUGAUGAGGCCGAAAGGCCGAA AAGUCCA | 485 |
| 1569 | CUCAGGG CUGAUGAGGCCGAAAGGCCGAA AGCCAAA | 486 |
| 1570 | GCUCAGG CUGAUGAGGCCGAAAGGCCGAA AAGCCAA | 487 |
| 1592 | UGGAGGA CUGAUGAGGCCGAAAGGCCGAA AUCCACC | 488 |
| 1593 | CUGGAGG CUGAUGAGGCCGAAAGGCCGAA AAUCCAC | 489 |
| 1594 | UCUGGAG CUGAUGAGGCCGAAAGGCCGAA AAAUCCA | 490 |
| 1597 | AGCUCUG CUGAUGAGGCCGAAAGGCCGAA AGGAAAU | 491 |
| 1605 | CUAGCUC CUGAUGAGGCCGAAAGGCCGAA AGCUCUG | 492 |
| 1611 | AGACUUC CUGAUGAGGCCGAAAGGCCGAA AGCUCAA | 493 |
| 1617 | CCUUGGA CUGAUGAGGCCGAAAGGCCGAA ACUUCUA | 494 |
| 1619 | CUCCUUG CUGAUGAGGCCGAAAGGCCGAA AGACUUC | 495 |
| 1629 | CCAUCCC CUGAUGAGGCCGAAAGGCCGAA ACCUCCU | 496 |
| 1641 | CUGCUAC CUGAUGAGGCCGAAAGGCCGAA AGCCCCA | 497 |
| 1644 | CUUCUGC CUGAUGAGGCCGAAAGGCCGAA ACAAGCC | 498 |
| 1666 | CAGCUGU CUGAUGAGGCCGAAAGGCCGAA AGCCUGG | 499 |
| 1686 | UGGAGGA CUGAUGAGGCCGAAAGGCCGAA ACACCAG | 500 |
| 1688 | GCUGGAG CUGAUGAGGCCGAAAGGCCGAA AGACACC | 501 |
| 1691 | CACGCUG CUGAUGAGGCCGAAAGGCCGAA AGGAGAC | 502 |
| 1707 | CUAACCC CUGAUGAGGCCGAAAGGCCGAA ACUUCCA | 503 |
| 1712 | UACUCCU CUGAUGAGGCCGAAAGGCCGAA ACCCAAC | 504 |
| 1713 | GUACUCC CUGAUGAGGCCGAAAGGCCGAA AACCCAA | 505 |
| 1719 | AUCUCCG CUGAUGAGGCCGAAAGGCCGAA ACUCCUA | 506 |
| 1733 | GGAAGCC CUGAUGAGGCCGAAAGGCCGAA AUCUCCA | 507 |
| 1738 | GAGUUGG CUGAUGAGGCCGAAAGGCCGAA AGCCAAU | 508 |
| 1745 | UAGGGAG CUGAUGAGGCCGAAAGGCCGAA AGUUGGG | 509 |
| 1748 | GGAUAGG CUGAUGAGGCCGAAAGGCCGAA AGGAGUU | 510 |
| 1752 | UUUAGGA CUGAUGAGGCCGAAAGGCCGAA AGGGAGG | 511 |
| 1754 | CCUUUAG CUGAUGAGGCCGAAAGGCCGAA AUAGGGA | 512 |

TABLE III-continued

Human CETP HH Ribozyme Sequence

| nt. Position | HH Ribozyme Sequence | Sequence ID No. |
|---|---|---|
| 1757 | GGGCCUU CUGAUGAGGCCGAAAGGCCGAA AGGAUAG | 513 |
| 1773 | GCACUUU CUGAUGAGGCCGAAAGGCCGAA AUGCCAG | 514 |
| 1774 | AGCACUU CUGAUGAGGCCGAAAGGCCGAA AAUGCCA | 515 |

TABLE IV

Rabbit CETP HH Target Sequence

| nt. Positon | Target Sequence | Sequence ID No. |
|---|---|---|
| 20 | GGCgCCU C cuACGAG | 516 |
| 23 | GCCUcCU a CgAgGcu | 517 |
| 23 | gccUCCU a CgagGCU | 518 |
| 36 | CuGGCAU C GUGUGuC | 519 |
| 43 | cgUGuGU c GCAucAC | 520 |
| 43 | CgUgUgU c gCAUCAc | 521 |
| 48 | GuCGCAU C ACCAAGC | 522 |
| 63 | CcGCCCU C uUGGUGU | 523 |
| 71 | uUGGUGU U GAACCAa | 524 |
| 96 | AGGUGgU C CAGACgG | 525 |
| 96 | AGGUGgU C CaGaCgg | 526 |
| 96 | AGGuGGU C caGAcGG | 527 |
| 107 | ACgGCCU U CCAGCGg | 528 |
| 108 | CgGCCUU C CAGCGcG | 529 |
| 122 | GCCgGCU A uCCgGAc | 530 |
| 132 | CgGAcgU C AgcGGCG | 531 |
| 132 | cgGAcGU c agCGGCG | 532 |
| 132 | cGGacGU C aGCGGCg | 533 |
| 156 | UGAUGCU C CUcGGCC | 534 |
| 159 | UGCUCCU c GGCCggG | 535 |
| 168 | GCCggGU C AAGUAcG | 536 |
| 168 | GccGGGU c AaGuacg | 537 |
| 173 | GUCAAGU A cGGGcUG | 538 |
| 189 | aCaACcU c CAgAuCA | 539 |
| 189 | ACAACcU C CAGAUCA | 540 |
| 195 | UCCAGAU C AGCCACc | 541 |
| 206 | CACcUGU C CAUCGCC | 542 |
| 210 | UGUCCAU C GCCAGCA | 543 |
| 249 | AGaCCAU c GAcGUCg | 544 |
| 255 | UcGAcGU C gCCAUcC | 545 |
| 261 | UCgCCAU c CAGAACG | 546 |
| 261 | ucgCCAU C CAGAaCg | 547 |
| 272 | aACgUgU c CGuGgUC | 548 |
| 272 | AACGUGU C cGAGGUC | 549 |
| 279 | CcGUGGU C UUCAAGG | 550 |
| 279 | ccGugGU C UuCAAGG | 551 |
| 281 | GUGGUCU U CAAGGGG | 552 |
| 282 | UGGUCUU C AAGGGGA | 553 |
| 299 | CUGAAcU A caGCUAC | 554 |
| 299 | CuGAaCU a cAGCUAc | 555 |
| 305 | uAcAgcU A cACGaGu | 556 |
| 305 | UAcaGCU A CACgAgU | 557 |
| 305 | UaCAgCU A CAcGAgU | 558 |
| 323 | UGGggGU U GGGcauc | 559 |
| 330 | UGGGcAU c aAUCAGU | 560 |
| 334 | CauCAaU C AGucuGU | 561 |
| 334 | cAUcaAU C AGUCugU | 562 |
| 338 | aAUCAGU c ugUcGAC | 563 |
| 342 | AGUCugU c GACUUCG | 564 |
| 342 | AgUCUGU c GacUuCg | 565 |
| 347 | gUcGACU U CGAGAUC | 566 |
| 348 | UcGACUU C GAGAUCG | 567 |
| 354 | UCGAGAU C GACUCUG | 568 |
| 354 | UCGaGAU C gAcUCUg | 569 |
| 354 | UCGAGaU c GacUcUg | 570 |
| 354 | UcGAGAU c GaCUCug | 571 |
| 359 | AuCgACU c ugCCAUu | 572 |
| 359 | AUCGACU C UGCCAUU | 573 |
| 359 | AuCGAcU C UgCCAuU | 574 |
| 366 | CUGCCAU U GACCUCC | 575 |
| 372 | UUGACCU C CAGAUCA | 576 |
| 372 | UuGAccU C CAGAUcA | 577 |
| 372 | UUGAcCU c cAgaUCa | 578 |
| 378 | UCCAGAU C AACACAg | 579 |
| 378 | UCCAGAU c AacaCAg | 580 |
| 378 | UCCAgaU c aACacAG | 581 |
| 434 | GACUGCU A CCUGgCU | 582 |
| 434 | gACUgCU a CCUggCu | 583 |
| 442 | CCUGgCU U UCCAUAA | 584 |
| 442 | CCUGgCU U UCCAUAA | 585 |
| 442 | CCUggCU u UCCauAA | 586 |
| 443 | CUGgCUU U CCAUAAa | 587 |
| 443 | CugGcUU u CcauAAA | 588 |
| 444 | uGGcuuU c CAUAaAC | 589 |
| 444 | UGgCUUU C CAUAAaC | 590 |
| 448 | UUUCCAU A AaCUGCU | 591 |
| 456 | AaCUGCU C CUGCAcC | 592 |
| 465 | UGCAcCU C CAgGGGG | 593 |
| 492 | gGUGgCU C aaGcAGc | 594 |
| 492 | GGUGGcU C AAGCAGC | 595 |
| 492 | GGuGGCU c aagCAGC | 596 |
| 492 | gGUgGCU c AagCAgc | 597 |
| 503 | CAGCUcU U CACAAAc | 598 |
| 503 | CAgcUCU U CacaaAc | 599 |
| 504 | aGCucuU c ACAaACu | 600 |
| 504 | AGCUcUU C ACAAAcU | 601 |
| 512 | ACAAAcU U CAUCUCC | 602 |
| 513 | CAAAcUU C AUCUCCU | 603 |
| 516 | AcUUCAU C UCCUUCA | 604 |
| 518 | UUCAUCU C CUUCACC | 605 |
| 521 | AUCUCCU U CACCCUG | 606 |
| 521 | aUCUcCU U cAcCCUg | 607 |
| 521 | aUCUCCU u CAcCcUG | 608 |
| 522 | UCUCCUU C ACCCUGA | 609 |
| 537 | AGCUGaU u CUGAAGc | 610 |
| 552 | GACAGgU C UGCAAuG | 611 |
| 552 | GaCAggU C UgCAaUG | 612 |
| 564 | AuGAGAU C AACacCA | 613 |
| 573 | ACacCAU U UCcAACA | 614 |
| 573 | AcacCAU C UcCAAcA | 615 |
| 575 | acCAUCU C cAACAUC | 616 |
| 582 | cCAACaU C AUggCUg | 617 |
| 582 | CcAACAU C AUGGCuG | 618 |
| 593 | GCuGAcU U UGUCCAG | 619 |
| 594 | CuGAcUU U GUCCAGA | 620 |
| 597 | AcUUUGU C CAGACgA | 621 |
| 618 | CCAGCAU C CUcUCAG | 622 |
| 621 | GCAUCCU c UCAGAUG | 623 |
| 623 | AUCCUcU C AGAUGGA | 624 |
| 623 | aUccUCU c AGAuggA | 625 |
| 636 | GAGACAU c GGGGUGG | 626 |
| 648 | UGGACAU U UCCgUGA | 627 |
| 649 | GGACAUU U CCgUGAC | 628 |
| 650 | GACAUUU C CgUGACg | 629 |
| 650 | gAcauUU C cGUGAcG | 630 |
| 669 | ccCCuGU C AUCACAG | 631 |
| 672 | CuGUCAU C ACAGCCa | 632 |
| 672 | cuGUCAU c aCAgCcA | 633 |

TABLE IV-continued

Rabbit CETP HH Target Sequence

| nt. Positon | Target Sequence | Sequence ID No. |
|---|---|---|
| 683 | GCCAccU a CcUgGAg | 634 |
| 683 | GCCaCCU A CCUGGAG | 635 |
| 692 | CuggAgU c cCAUCaC | 636 |
| 692 | CUGGAGU C CCAUCAC | 637 |
| 697 | GUCCCAU C ACAAGGG | 638 |
| 706 | CAAGGGU C AcUUCAc | 639 |
| 710 | GGUCAcU U CAcgcAC | 640 |
| 711 | GUCAcUU C AcgcACA | 641 |
| 726 | AGAAcGU C UCcGAGG | 642 |
| 728 | AAcGUCU C cGAGGcC | 643 |
| 737 | GAGgCcU u CcCcCuC | 644 |
| 738 | AGGcCuU C CCCCUCC | 645 |
| 744 | UCCCCCU C CgCgCCU | 646 |
| 752 | CgCgCCU U CcCgCCC | 647 |
| 752 | CGcGcCU u CCcgCCc | 648 |
| 753 | gCgCCUU C cCGCCCg | 649 |
| 776 | GGGGACU C CCGCAUG | 650 |
| 788 | AUGCUcU A CUUCUGG | 651 |
| 791 | CUcUACU U CUGGUUC | 652 |
| 792 | UcUACUU C UGGUUCU | 653 |
| 797 | UUCUGGU U CUCcGAu | 654 |
| 798 | UCUGGUU C UCcGAuC | 655 |
| 800 | UGGUUCU c cGAuCaA | 656 |
| 805 | CUCcGaU c aAGUGCC | 657 |
| 818 | cUCaACU C cCUGGCC | 658 |
| 836 | GccGCcU U CCAGGAg | 659 |
| 836 | GcCgccU u cCAGgAG | 660 |
| 837 | CcgCCUU c CAGgaGG | 661 |
| 837 | ccGCcUU C CAGGAgG | 662 |
| 852 | gCCgUCU C GugCuCA | 663 |
| 852 | GCCGuCU C gUGCUCA | 664 |
| 858 | UCgUGCU C AGCCUGA | 665 |
| 878 | GAuGAGU U CAAGaaA | 666 |
| 879 | AuGAGUU C AAGaaAG | 667 |
| 905 | caGGGuU U CgACACC | 668 |
| 906 | aGGGuUU C gACACCA | 669 |
| 924 | AGGAAAU C UUCCAgG | 670 |
| 926 | GAAAUCU U CCAgGAG | 671 |
| 926 | GAAaUCU u CcAGGAG | 672 |
| 927 | AAAUCUU C CAgGAGc | 673 |
| 936 | aGgAGCU U UCCAGag | 674 |
| 937 | gGAGCUU u CcagAGg | 675 |
| 969 | CCcAGGU A GCcgUCC | 676 |
| 969 | CCCAgGU a gCCGUCC | 677 |
| 975 | UagCCGU C CACUGCC | 678 |
| 984 | ACUGCCU u AAGgUGC | 679 |
| 985 | cuGCcUU A AgGUGCc | 680 |
| 999 | CCAAGAU C UCCUGCC | 681 |
| 1001 | AAGAUCU C CUGCCAg | 682 |
| 1020 | gGGGuGU C GUGGUgu | 683 |
| 1028 | gUGGUGU C UuCUuCc | 684 |
| 1030 | GGUgucU U CUUCcGU | 685 |
| 1030 | GGUGUCU u CUuCcGu | 686 |
| 1034 | UCuUcUU C CGUcGcc | 687 |
| 1049 | GUGAcgU U CCgCUUc | 688 |
| 1049 | gUGaCgU u CcGCUuC | 689 |
| 1050 | UGAcgUU C CgCUUcC | 690 |
| 1055 | UUCCgCU U cCCcCGC | 691 |
| 1056 | UCCgCUU c CCcCGCC | 692 |
| 1088 | GUgGCcU A CAggUUU | 693 |
| 1094 | UACAggU U UGAgGAG | 694 |
| 1095 | ACAggUU U GAgGAGG | 695 |
| 1105 | gGAGGAU A UCaUcAC | 696 |
| 1107 | AGGAUAU C aUcACcA | 697 |
| 1110 | auAUcAU C ACCaCcG | 698 |
| 1119 | CCACcGU C CaGgCCu | 699 |
| 1119 | CcACCGU C CAGGCCU | 700 |
| 1119 | CcAcCgU c cAGGCCu | 701 |
| 1127 | cagGCCU C cUacUCC | 702 |
| 1127 | CAGGCCU C CUAcUCc | 703 |
| 1130 | GCCUCCU A cUCcCAG | 704 |
| 1133 | UCCUAcU C ccAGAAA | 705 |
| 1146 | AAaagCU C UUcCuAC | 706 |
| 1146 | AAAAGCU U UUCcUAc | 707 |
| 1148 | AAGCUCU U CcUAcaC | 708 |
| 1149 | AGCUCUU C cUAcaCC | 709 |
| 1152 | UCUUCcU A caCCUCU | 710 |
| 1158 | UAcaCCU C UUGGAUU | 711 |
| 1160 | caCCUCU U GGAUUUC | 712 |
| 1165 | CuUGgAU u UCCAguG | 713 |
| 1165 | CUUGGAU U UCCAGug | 714 |
| 1166 | UUGGAUU U CCAGugc | 715 |
| 1166 | UUGGaUU u ccAGUgC | 716 |
| 1245 | AGgCUGU U UCCAACc | 717 |
| 1246 | GgCUGUU U CCAACcU | 718 |
| 1247 | gCuGuuU C aACCUG | 719 |
| 1247 | gCUGUUU C CAACcUG | 720 |
| 1247 | gcUGUUU c CAaCCug | 721 |
| 1268 | AGCcGCU C CGAGUCC | 722 |
| 1274 | UCCGAGU C CcUgCAG | 723 |
| 1286 | CAGAGCU c uCUcCgc | 724 |
| 1290 | gCUCUcU C CgCuCCC | 725 |
| 1302 | cCCUGAU c gCCAcGg | 726 |
| 1317 | UGGGCAU C CCgGAGG | 727 |
| 1326 | CgGAGGU C AUGUCUC | 728 |
| 1331 | GUCAUGU C UCGGCUC | 729 |
| 1333 | CAUGUCU C GGCUCGA | 730 |
| 1338 | CUCGGCU C GAGGUgG | 731 |
| 1349 | GuGGCgU u CaCAGCC | 732 |
| 1349 | GUgGcGU U cACAGCC | 733 |
| 1350 | UgGcGUU c ACAGCCC | 734 |
| 1350 | UGGcGuU c acAGCcc | 735 |
| 1359 | CAGCCCU C AUGAACA | 736 |
| 1383 | UGgaCCU C UUCGAaA | 737 |
| 1385 | gaCCUCU U CGAaAUC | 738 |
| 1386 | aCCUCUU C GAaAUCA | 739 |
| 1392 | UCGAaAU C AUCAACC | 740 |
| 1395 | AaAUCAU C AACCCcG | 741 |
| 1407 | CcGAGAU U AUCACUC | 742 |
| 1408 | CGAGauU a uCACUCu | 743 |
| 1408 | cGAGAUU A UCACUCu | 744 |
| 1410 | AGAUUAU C ACUCucG | 745 |
| 1414 | UAUCACU C ucGAUGG | 746 |
| 1445 | AUGGACU U cGGuUUu | 747 |
| 1446 | UGGACUU c GGuUUuC | 748 |
| 1451 | UUcGGuU U uCCcaAG | 749 |
| 1452 | UcGGuUU u CCcaAGC | 750 |
| 1474 | GGuGGAU U UccUgCA | 751 |
| 1474 | GGUGGAU U UCCUgCA | 752 |
| 1475 | GUGGAUU U CCUgCAG | 753 |
| 1476 | UGGAUUU C CUgCAGA | 754 |
| 1529 | gACGuCU C cGcCCAu | 755 |
| 1529 | GAcGUCU C CgccCAu | 756 |
| 1549 | UgGagGU c aGGgagU | 757 |
| 1580 | GAUGGCU c CCaaCUc | 758 |
| 1580 | gaUGGCU C CCAACUC | 759 |
| 1587 | CCCAACU C CUuCugu | 760 |
| 1595 | CUucUGU c CuGaaGa | 761 |
| 1595 | CUuCUgU c CUgAagA | 762 |
| 1595 | cuuCUgU c CUgAAGa | 763 |
| 1624 | GCAgCAU a CccUgGg | 764 |
| 1694 | uCcGGaU c cCAGCUG | 765 |
| 1787 | cCuGGCU u uAGcCUG | 766 |
| 1788 | CUGGCUu U AgccUGC | 767 |
| 1816 | gCuAaAU c UCuCuGG | 768 |
| 1818 | UaAAUCU C UcuGGGu | 769 |
| 1818 | uAAaucU C UcUgGCU | 770 |
| 1828 | UggCUGU C UcUCucU | 771 |
| 1847 | CUcaAGU a AAcGAau | 772 |

TABLE V

| nt. Position | Ribozyme Sequence | Sequence ID No. |
|---|---|---|
| 20 | CUCGUAG CUGAUGAGGCCGAAAGGCCGAA AGGCGCC | 773 |
| 23 | AGCCUCG CUGAUGAGGCCGAAAGGCCGAA AGGAGGC | 774 |
| 23 | AGCCUCG CUGAUGAGGCCGAAAGGCCGAA AGGAGGC | 775 |
| 36 | GACACAC CUGAUGAGGCCGAAAGGCCGAA AUGCCAG | 776 |
| 43 | GUGAUGC CUGAUGAGGCCGAAAGGCCGAA ACACACG | 777 |
| 43 | GUGAUGC CUGAUGAGGCCGAAAGGCCGAA ACACACG | 778 |
| 48 | GCUUGGU CUGAUGAGGCCGAAAGGCCGAA AUGCGAC | 779 |
| 63 | ACACCAA CUGAUGAGGCCGAAAGGCCGAA AGGGCGG | 780 |
| 71 | UUGGUUC CUGAUGAGGCCGAAAGGCCGAA ACACCAA | 781 |
| 96 | CCGUCUG CUGAUGAGGCCGAAAGGCCGAA ACCACCU | 782 |
| 96 | CCGUCUG CUGAUGAGGCCGAAAGGCCGAA ACCACCU | 783 |
| 96 | CCGUCUG CUGAUGAGGCCGAAAGGCCGAA ACCACCU | 784 |
| 107 | GCGCUGG CUGAUGAGGCCGAAAGGCCGAA AGGCCGU | 785 |
| 108 | CGCGCUG CUGAUGAGGCCGAAAGGCCGAA AAGGCCG | 786 |
| 122 | GUCCGGA CUGAUGAGGCCGAAAGGCCGAA AGCCGGC | 787 |
| 132 | CGCCGCU CUGAUGAGGCCGAAAGGCCGAA ACGUCCG | 788 |
| 132 | CGCCGCU CUGAUGAGGCCGAAAGGCCGAA ACGUCCG | 789 |
| 132 | CGCCGCU CUGAUGAGGCCGAAAGGCCGAA ACGUCCG | 790 |
| 156 | GGCCGAG CUGAUGAGGCCGAAAGGCCGAA AGCAUCA | 791 |
| 159 | CCCGGCC CUGAUGAGGCCGAAAGGCCGAA AGGAGCA | 792 |
| 168 | CGUACUU CUGAUGAGGCCGAAAGGCCGAA ACCCGGC | 793 |
| 168 | CGUACUU CUGAUGAGGCCGAAAGGCCGAA ACCCGGC | 794 |
| 173 | CAGCCCG CUGAUGAGGCCGAAAGGCCGAA ACUUGAC | 795 |
| 189 | UGAUCUG CUGAUGAGGCCGAAAGGCCGAA AGGUUGU | 796 |
| 189 | UGAUCUG CUGAUGAGGCCGAAAGGCCGAA AGGUUGU | 797 |
| 195 | GGUGGCU CUGAUGAGGCCGAAAGGCCGAA AUCUGGA | 798 |
| 206 | GGCGAUG CUGAUGAGGCCGAAAGGCCGAA ACAGGUG | 799 |
| 210 | UGCUGGC CUGAUGAGGCCGAAAGGCCGAA AUGGACA | 800 |
| 249 | CGACGUC CUGAUGAGGCCGAAAGGCCGAA AUGGUCU | 801 |
| 255 | GGAUGGC CUGAUGAGGCCGAAAGGCCGAA ACGUCCA | 802 |
| 261 | CGUUCUG CUGAUGAGGCCGAAAGGCCGAA AUGGCGA | 803 |
| 261 | CGUUCUG CUGAUGAGGCCGAAAGGCCGAA AUGGCGA | 804 |
| 272 | GACCACG CUGAUGAGGCCGAAAGGCCGAA ACACGUU | 805 |
| 272 | GACCACG CUGAUGAGGCCGAAAGGCCGAA ACACGUU | 806 |
| 279 | CCUUGAA CUGAUGAGGCCGAAAGGCCGAA ACCACGG | 807 |
| 279 | CCUUGAA CUGAUGAGGCCGAAAGGCCGAA ACCACGG | 808 |
| 281 | CCCCUUG CUGAUGAGGCCGAAAGGCCGAA AGACCAC | 809 |
| 282 | UCCCCUU CUGAUGAGGCCGAAAGGCCGAA AAGACCA | 810 |
| 299 | GUAGCUG CUGAUGAGGCCGAAAGGCCGAA AGUUCAG | 811 |
| 299 | GUAGCUG CUGAUGAGGCCGAAAGGCCGAA AGUUCAG | 812 |
| 305 | ACUCGUG CUGAUGAGGCCGAAAGGCCGAA AGCUGUA | 813 |
| 305 | ACUCGUG CUGAUGAGGCCGAAAGGCCGAA AGCUGUA | 814 |
| 305 | ACUCGUG CUGAUGAGGCCGAAAGGCCGAA AGCUGUA | 815 |
| 323 | GAUGCCC CUGAUGAGGCCGAAAGGCCGAA ACCCCCA | 816 |
| 330 | ACUGAUU CUGAUGAGGCCGAAAGGCCGAA AUGCCCA | 817 |
| 334 | ACAGACU CUGAUGAGGCCGAAAGGCCGAA AUUGAUG | 818 |
| 334 | ACAGACU CUGAUGAGGCCGAAAGGCCGAA AUUGAUG | 819 |
| 338 | GUCGACA CUGAUGAGGCCGAAAGGCCGAA ACUGAUU | 820 |
| 342 | CGAAGUC CUGAUGAGGCCGAAAGGCCGAA ACAGACU | 821 |
| 342 | CGAAGUC CUGAUGAGGCCGAAAGGCCGAA ACAGACU | 822 |
| 347 | GAUCUCG CUGAUGAGGCCGAAAGGCCGAA AGUCGAC | 823 |
| 348 | CGAUCUC CUGAUGAGGCCGAAAGGCCGAA AAGUCGA | 824 |
| 354 | CAGAGUC CUGAUGAGGCCGAAAGGCCGAA AUCUCGA | 825 |
| 354 | CAGAGUC CUGAUGAGGCCGAAAGGCCGAA AUCUCGA | 826 |
| 354 | CAGAGUC CUGAUGAGGCCGAAAGGCCGAA AUCUCGA | 827 |
| 354 | CAGAGUC CUGAUGAGGCCGAAAGGCCGAA AUCUCGA | 828 |
| 359 | AAUGGCA CUGAUGAGGCCGAAAGGCCGAA AGUCGAU | 829 |
| 359 | AAUGGCA CUGAUGAGGCCGAAAGGCCGAA AGUCGAU | 830 |
| 359 | AAUGGCA CUGAUGAGGCCGAAAGGCCGAA AGUCGAU | 831 |
| 366 | GGAGGUC CUGAUGAGGCCGAAAGGCCGAA AUGGCAG | 832 |
| 372 | UGAUCUG CUGAUGAGGCCGAAAGGCCGAA AGGUCAA | 833 |
| 372 | UGAUCUG CUGAUGAGGCCGAAAGGCCGAA AGGUCAA | 834 |
| 372 | UGAUCUG CUGAUGAGGCCGAAAGGCCGAA AGGUCAA | 835 |
| 378 | CUGUGUU CUGAUGAGGCCGAAAGGCCGAA AUCUGGA | 836 |
| 378 | CUGUGUU CUGAUGAGGCCGAAAGGCCGAA AUCUGGA | 837 |
| 378 | CUGUGUU CUGAUGAGGCCGAAAGGCCGAA AUCUGGA | 838 |
| 434 | AGCCAGG CUGAUGAGGCCGAAAGGCCGAA AGCAGUC | 839 |
| 434 | AGCCAGG CUGAUGAGGCCGAAAGGCCGAA AGCAGUC | 840 |
| 442 | UUAUGGA CUGAUGAGGCCGAAAGGCCGAA AGCCAGG | 841 |
| 442 | UUAUGGA CUGAUGAGGCCGAAAGGCCGAA AGCCAGG | 842 |
| 442 | UUAUGGA CUGAUGAGGCCGAAAGGCCGAA AGCCAGG | 843 |
| 443 | UUUAUGG CUGAUGAGGCCGAAAGGCCGAA AAGCCAG | 844 |
| 443 | UUUAUGG CUGAUGAGGCCGAAAGGCCGAA AAGCCAG | 845 |
| 444 | GUUUAUG CUGAUGAGGCCGAAAGGCCGAA AAAGCCA | 846 |
| 444 | GUUUAUG CUGAUGAGGCCGAAAGGCCGAA AAAGCCA | 847 |
| 448 | AGCAGUU CUGAUGAGGCCGAAAGGCCGAA AUGGAAA | 848 |

TABLE V-continued

| nt. Position | Ribozyme Sequence | Sequence ID No. |
|---|---|---|
| 456 | GGUGCAG CUGAUGAGGCCGAAAGGCCGAA AGCAGUU | 849 |
| 465 | CCCCCUG CUGAUGAGGCCGAAAGGCCGAA AGGUGCA | 850 |
| 492 | GCUGCUU CUGAUGAGGCCGAAAGGCCGAA AGCCACC | 851 |
| 492 | GCUGCUU CUGAUGAGGCCGAAAGGCCGAA AGCCACC | 852 |
| 492 | GCUGCUU CUGAUGAGGCCGAAAGGCCGAA AGCCACC | 853 |
| 492 | GCUGCUU CUGAUGAGGCCGAAAGGCCGAA AGCCACC | 854 |
| 503 | GUUUGUG CUGAUGAGGCCGAAAGGCCGAA AGAGCUG | 855 |
| 503 | GUUUGUG CUGAUGAGGCCGAAAGGCCGAA AGAGCUG | 856 |
| 504 | AGUUUGU CUGAUGAGGCCGAAAGGCCGAA AAGAGCU | 857 |
| 504 | AGUUUGU CUGAUGAGGCCGAAAGGCCGAA AAGAGCU | 858 |
| 512 | GGAGAUG CUGAUGAGGCCGAAAGGCCGAA AGUUUGU | 859 |
| 513 | AGGAGAU CUGAUGAGGCCGAAAGGCCGAA AAGUUUG | 860 |
| 516 | UGAAGGA CUGAUGAGGCCGAAAGGCCGAA AUGAAGU | 861 |
| 518 | GGUGAAG CUGAUGAGGCCGAAAGGCCGAA AGAUGAA | 862 |
| 521 | CAGGGUG CUGAUGAGGCCGAAAGGCCGAA AGGAGAU | 863 |
| 521 | CAGGGUG CUGAUGAGGCCGAAAGGCCGAA AGGAGAU | 864 |
| 521 | CAGGGUG CUGAUGAGGCCGAAAGGCCGAA AGGAGAU | 865 |
| 522 | UCAGGGU CUGAUGAGGCCGAAAGGCCGAA AAGGAGA | 866 |
| 537 | GCUUCAG CUGAUGAGGCCGAAAGGCCGAA AUCAGCU | 867 |
| 552 | CAUUGCA CUGAUGAGGCCGAAAGGCCGAA ACCUGUC | 868 |
| 552 | CAUUGCA CUGAUGAGGCCGAAAGGCCGAA ACCUGUC | 869 |
| 564 | UGGUGUU CUGAUGAGGCCGAAAGGCCGAA AUCUCAU | 870 |
| 573 | UGUUGGA CUGAUGAGGCCGAAAGGCCGAA AUGGUGU | 871 |
| 573 | UGUUGGA CUGAUGAGGCCGAAAGGCCGAA AUGGUGU | 872 |
| 575 | GAUGUUG CUGAUGAGGCCGAAAGGCCGAA AGAUGGU | 873 |
| 582 | CAGCCAU CUGAUGAGGCCGAAAGGCCGAA AUGUUGG | 874 |
| 582 | CAGCCAU CUGAUGAGGCCGAAAGGCCGAA AUGUUGG | 875 |
| 593 | CUGGACA CUGAUGAGGCCGAAAGGCCGAA AGUCAGC | 876 |
| 594 | UCUGGAC CUGAUGAGGCCGAAAGGCCGAA AAGUCAG | 877 |
| 597 | UCGUCUG CUGAUGAGGCCGAAAGGCCGAA ACAAAGU | 878 |
| 618 | CUGAGAG CUGAUGAGGCCGAAAGGCCGAA AUGCUGG | 879 |
| 621 | CAUCUGA CUGAUGAGGCCGAAAGGCCGAA AGGAUGC | 880 |
| 623 | UCCAUCU CUGAUGAGGCCGAAAGGCCGAA AGAGGAU | 881 |
| 623 | UCCAUCU CUGAUGAGGCCGAAAGGCCGAA AGAGGAU | 882 |
| 636 | CCACCCC CUGAUGAGGCCGAAAGGCCGAA AUGUCUC | 883 |
| 648 | UCACGGA CUGAUGAGGCCGAAAGGCCGAA AUGUCCA | 884 |
| 649 | GUCACGG CUGAUGAGGCCGAAAGGCCGAA AAUGUCC | 885 |
| 650 | CGUCACG CUGAUGAGGCCGAAAGGCCGAA AAAUGUC | 886 |
| 650 | CGUCACG CUGAUGAGGCCGAAAGGCCGAA AAAUGUC | 887 |
| 669 | CUGUGAU CUGAUGAGGCCGAAAGGCCGAA ACAGGGG | 888 |
| 672 | UGGCUGU CUGAUGAGGCCGAAAGGCCGAA AUGACAG | 889 |
| 672 | UGGCUGU CUGAUGAGGCCGAAAGGCCGAA AUGACAG | 890 |
| 683 | CUCCAGG CUGAUGAGGCCGAAAGGCCGAA AGGUGGC | 891 |
| 683 | CUCCAGG CUGAUGAGGCCGAAAGGCCGAA AGGUGGC | 892 |
| 692 | GUGAUGG CUGAUGAGGCCGAAAGGCCGAA ACUCCAG | 893 |
| 692 | GUGAUGG CUGAUGAGGCCGAAAGGCCGAA ACUCCAG | 894 |
| 697 | CCCUUGU CUGAUGAGGCCGAAAGGCCGAA AUGGGAC | 895 |
| 706 | GUGAAGU CUGAUGAGGCCGAAAGGCCGAA ACCCUUG | 896 |
| 710 | GUGCGUG CUGAUGAGGCCGAAAGGCCGAA AGUGACC | 897 |
| 711 | UGUGCGU CUGAUGAGGCCGAAAGGCCGAA AAGUGAC | 898 |
| 726 | CCUCGGA CUGAUGAGGCCGAAAGGCCGAA ACGUUCU | 899 |
| 728 | GGCCUCG CUGAUGAGGCCGAAAGGCCGAA AGACGUU | 900 |
| 737 | GAGGGGG CUGAUGAGGCCGAAAGGCCGAA AGGCCUC | 901 |
| 738 | GGAGGGG CUGAUGAGGCCGAAAGGCCGAA AAGGCCU | 902 |
| 744 | AGGCGCG CUGAUGAGGCCGAAAGGCCGAA AGGGGGA | 903 |
| 752 | GGGCGGG CUGAUGAGGCCGAAAGGCCGAA AGGCGCG | 904 |
| 752 | GGGCGGG CUGAUGAGGCCGAAAGGCCGAA AGGCGCG | 905 |
| 753 | CGGGCGG CUGAUGAGGCCGAAAGGCCGAA AAGGCGC | 906 |
| 776 | CAUGCGG CUGAUGAGGCCGAAAGGCCGAA AGUCCCC | 907 |
| 788 | CCAGAAG CUGAUGAGGCCGAAAGGCCGAA AGAGCAU | 908 |
| 791 | GAACCAG CUGAUGAGGCCGAAAGGCCGAA AGUAGAG | 909 |
| 792 | AGAACCA CUGAUGAGGCCGAAAGGCCGAA AAGUAGA | 910 |
| 797 | AUCGGAG CUGAUGAGGCCGAAAGGCCGAA ACCAGAA | 911 |
| 798 | GAUCGGA CUGAUGAGGCCGAAAGGCCGAA AACCAGA | 912 |
| 800 | UUGAUCG CUGAUGAGGCCGAAAGGCCGAA AGAACCA | 913 |
| 805 | AGCACUU CUGAUGAGGCCGAAAGGCCGAA AUCGGAG | 914 |
| 818 | GGCCAGG CUGAUGAGGCCGAAAGGCCGAA AGUUGAG | 915 |
| 836 | CUCCUGG CUGAUGAGGCCGAAAGGCCGAA AGGCGGC | 916 |
| 836 | CUCCUGG CUGAUGAGGCCGAAAGGCCGAA AGGCGGC | 917 |
| 837 | CCUCCUG CUGAUGAGGCCGAAAGGCCGAA AAGGCGG | 918 |
| 837 | CCUCCUG CUGAUGAGGCCGAAAGGCCGAA AAGGCGG | 919 |
| 852 | UGAGCAC CUGAUGAGGCCGAAAGGCCGAA AGACGGC | 920 |
| 852 | UGAGCAC CUGAUGAGGCCGAAAGGCCGAA AGACGGC | 921 |
| 858 | UCAGGCU CUGAUGAGGCCGAAAGGCCGAA AGCACGA | 922 |
| 878 | UUUCUUG CUGAUGAGGCCGAAAGGCCGAA ACUCAUC | 923 |
| 879 | CUUUCUU CUGAUGAGGCCGAAAGGCCGAA AACUCAU | 924 |

TABLE V-continued

| nt. Position | Ribozyme Sequence | Sequence ID No. |
|---|---|---|
| 905 | GGUGUCG CUGAUGAGGCCGAAAGGCCGAA AACCCUG | 925 |
| 906 | UGGUGUC CUGAUGAGGCCGAAAGGCCGAA AAACCCU | 926 |
| 924 | CCUGGAA CUGAUGAGGCCGAAAGGCCGAA AUUUCCU | 927 |
| 926 | CUCCUGG CUGAUGAGGCCGAAAGGCCGAA AGAUUUC | 928 |
| 926 | CUCCUGG CUGAUGAGGCCGAAAGGCCGAA AGAUUUC | 929 |
| 927 | GCUCCUG CUGAUGAGGCCGAAAGGCCGAA AAGAUUU | 930 |
| 936 | CUCUGGA CUGAUGAGGCCGAAAGGCCGAA AGCUCCU | 931 |
| 937 | CCUCUGG CUGAUGAGGCCGAAAGGCCGAA AAGCUCC | 932 |
| 969 | GGACGGC CUGAUGAGGCCGAAAGGCCGAA ACCUGGG | 933 |
| 969 | GGACGGC CUGAUGAGGCCGAAAGGCCGAA ACCUGGG | 934 |
| 975 | GGCAGUG CUGAUGAGGCCGAAAGGCCGAA ACGGCUA | 935 |
| 984 | GCACCUU CUGAUGAGGCCGAAAGGCCGAA AGGCAGU | 936 |
| 985 | GGCACCU CUGAUGAGGCCGAAAGGCCGAA AAGGCAG | 937 |
| 999 | GGCAGGA CUGAUGAGGCCGAAAGGCCGAA AUCUUGG | 938 |
| 1001 | CUGGCAG CUGAUGAGGCCGAAAGGCCGAA AGAUCUU | 939 |
| 1020 | ACACCAC CUGAUGAGGCCGAAAGGCCGAA ACACCCC | 940 |
| 1028 | GGAAGAA CUGAUGAGGCCGAAAGGCCGAA ACACCAC | 941 |
| 1030 | ACGGAAG CUGAUGAGGCCGAAAGGCCGAA AGACACC | 942 |
| 1030 | ACGCAAG CUGAUGAGGCCGAAAGGCCGAA AGACACC | 943 |
| 1034 | GGCGACG CUGAUGAGGCCGAAAGGCCGAA AAGAAGA | 944 |
| 1049 | GAAGCGG CUGAUGAGGCCGAAAGGCCGAA ACGUCAC | 945 |
| 1049 | GAAGCGG CUGAUGAGGCCGAAAGGCCGAA ACGUCAC | 946 |
| 1050 | GGAAGCG CUGAUGAGGCCGAAAGGCCGAA AACGUCA | 947 |
| 1055 | GCGGGGG CUGAUGAGGCCGAAAGGCCGAA AGCGGAA | 948 |
| 1056 | GGCGGGG CUGAUGAGGCCGAAAGGCCGAA AAGCGGA | 949 |
| 1088 | AAACCUG CUGAUGAGGCCGAAAGGCCGAA AGGCCAC | 950 |
| 1094 | CUCCUCA CUGAUGAGGCCGAAAGGCCGAA ACCUGUA | 951 |
| 1095 | CCUCCUC CUGAUGAGGCCGAAAGGCCGAA AACCUGU | 952 |
| 1105 | GUGAUGA CUGAUGAGGCCGAAAGGCCGAA AUCCUCC | 953 |
| 1107 | UGGUGAU CUGAUGAGGCCGAAAGGCCGAA AUAUCCU | 954 |
| 1110 | CGGUGGU CUGAUGAGGCCGAAAGGCCGAA AUGAUAU | 955 |
| 1119 | AGGCCUG CUGAUGAGGCCGAAAGGCCGAA ACGGUGG | 956 |
| 1119 | AGGCCUG CUGAUGAGGCCGAAAGGCCGAA ACGGUGG | 957 |
| 1119 | AGGCCUG CUGAUGAGGCCGAAAGGCCGAA ACGGUGG | 958 |
| 1127 | GGAGUAG CUGAUGAGGCCGAAAGGCCGAA AGGCCUG | 959 |
| 1127 | GGAGUAG CUGAUGAGGCCGAAAGGCCGAA AGGCCUG | 960 |
| 1130 | CUGGGAG CUGAUGAGGCCGAAAGGCCGAA AGGAGGC | 961 |
| 1133 | UUUCUGG CUGAUGAGGCCGAAAGGCCGAA AGUAGGA | 962 |
| 1146 | GUAGGAA CUGAUGAGGCCGAAAGGCCGAA AGCUUUU | 963 |
| 1146 | GUAGGAA CUGAUGAGGCCGAAAGGCCGAA AGCUUUU | 964 |
| 1148 | GUGUAGG CUGAUGAGGCCGAAAGGCCGAA AGAGCUU | 965 |
| 1149 | GGUGUAG CUGAUGAGGCCGAAAGGCCGAA AAGAGCU | 966 |
| 1152 | AGAGGUG CUGAUGAGGCCGAAAGGCCGAA AGGAAGA | 967 |
| 1158 | AAUCCAA CUGAUGAGGCCGAAAGGCCGAA AGGUGUA | 968 |
| 1160 | GAAAUCC CUGAUGAGGCCGAAAGGCCGAA AGAGGUG | 969 |
| 1165 | CACUGGA CUGAUGAGGCCGAAAGGCCGAA AUCCAAG | 970 |
| 1165 | CACUGGA CUGAUGAGGCCGAAAGGCCGAA AUCCAAG | 971 |
| 1166 | GCACUGG CUGAUGAGGCCGAAAGGCCGAA AAUCCAA | 972 |
| 1166 | GCACUGG CUGAUGAGGCCGAAAGGCCGAA AAUCCAA | 973 |
| 1245 | GGUUGGA CUGAUGAGGCCGAAAGGCCGAA ACAGCCU | 974 |
| 1246 | AGGUUGG CUGAUGAGGCCGAAAGGCCGAA AACAGCC | 975 |
| 1247 | CAGGUUG CUGAUGAGGCCGAAAGGCCGAA AAACAGC | 976 |
| 1247 | CAGGUUG CUGAUGAGGCCGAAAGGCCGAA AAACAGC | 977 |
| 1247 | CAGGUUG CUGAUGAGGCCGAAAGGCCGAA AAACAGC | 978 |
| 1268 | GGACUCG CUGAUGAGGCCGAAAGGCCGAA AGCGGCU | 979 |
| 1274 | CUGCAGG CUGAUGAGGCCGAAAGGCCGAA ACUCGGA | 980 |
| 1286 | GCGGAGA CUGAUGAGGCCGAAAGGCCGAA AGCUCUG | 981 |
| 1290 | GGGAGCG CUGAUGAGGCCGAAAGGCCGAA AGAGAGC | 982 |
| 1302 | CCGUGGC CUGAUGAGGCCGAAAGGCCGAA AUCAGGG | 983 |
| 1317 | CCUCCGG CUGAUGAGGCCGAAAGGCCGAA AUGCCCA | 984 |
| 1326 | GAGACAU CUGAUGAGGCCGAAAGGCCGAA ACCUCCG | 985 |
| 1331 | GAGCCGA CUGAUGAGGCCGAAAGGCCGAA ACAUGAC | 986 |
| 1333 | UCGAGCC CUGAUGAGGCCGAAAGGCCGAA AGACAUG | 987 |
| 1338 | CCACCUC CUGAUGAGGCCGAAAGGCCGAA AGCCGAG | 988 |
| 1349 | GGCUGUG CUGAUGAGGCCGAAAGGCCGAA ACGCCAC | 989 |
| 1349 | GGCUGUG CUGAUGAGGCCGAAAGGCCGAA ACGCCAC | 990 |
| 1350 | GGGCUGU CUGAUGAGGCCGAAAGGCCGAA AACGCCA | 991 |
| 1350 | GGGCUGU CUGAUGAGGCCGAAAGGCCGAA AACGCCA | 992 |
| 1359 | UGUUCAU CUGAUGAGGCCGAAAGGCCGAA AGGGCUG | 993 |
| 1383 | UUUCGAA CUGAUGAGGCCGAAAGGCCGAA AGGUCCA | 994 |
| 1385 | GAUUUCG CUGAUGAGGCCGAAAGGCCGAA AGAGGUC | 995 |
| 1386 | UGAUUUC CUGAUGAGGCCGAAAGGCCGAA AAGAGGU | 996 |
| 1392 | GGUUGAU CUGAUGAGGCCGAAAGGCCGAA AUUUCGA | 997 |
| 1395 | CGGGGUU CUGAUGAGGCCGAAAGGCCGAA AUGAUUU | 998 |
| 1407 | GAGUGAU CUGAUGAGGCCGAAAGGCCGAA AUCUCGG | 999 |
| 1408 | AGAGUGA CUGAUGAGGCCGAAAGGCCGAA AAUCUCG | 1000 |

TABLE V-continued

| nt. Position | Ribozyme Sequence | Sequence ID No. |
|---|---|---|
| 1408 | AGAGUGA CUGAUGAGGCCGAAAGGCCGAA AAUCUCG | 1001 |
| 1410 | CGAGAGU CUGAUGAGGCCGAAAGGCCGAA AUAAUCU | 1002 |
| 1414 | CCAUCGA CUGAUGAGGCCGAAAGGCCGAA AGUGAUA | 1003 |
| 1445 | AAAACCG CUGAUGAGGCCGAAAGGCCGAA AGUCCAU | 1004 |
| 1446 | GAAAACC CUGAUGAGGCCGAAAGGCCGAA AAGUCCA | 1005 |
| 1451 | CUUGGGA CUGAUGAGGCCGAAAGGCCGAA AACCGAA | 1006 |
| 1452 | GCUUGGG CUGAUGAGGCCGAAAGGCCGAA AAACCGA | 1007 |
| 1474 | UGCAGGA CUGAUGAGGCCGAAAGGCCGAA AUCCACC | 1008 |
| 1474 | UGCAGGA CUGAUGAGGCCGAAAGGCCGAA AUCCACC | 1009 |
| 1475 | CUGCAGG CUGAUGAGGCCGAAAGGCCGAA AAUCCAC | 1010 |
| 1476 | UCUGCAG CUGAUGAGGCCGAAAGGCCGAA AAAUCCA | 1011 |
| 1529 | AUGGGCG CUGAUGAGGCCGAAAGGCCGAA AGACGUC | 1012 |
| 1529 | AUGGGCG CUGAUGAGGCCGAAAGGCCGAA AGACGUC | 1013 |
| 1549 | ACUCCCU CUGAUGAGGCCGAAAGGCCGAA ACCUCCA | 1014 |
| 1580 | GAGUUGG CUGAUGAGGCCGAAAGGCCGAA AGCCAUC | 1015 |
| 1580 | GAGUUGG CUGAUGAGGCCGAAAGGCCGAA AGCCAUC | 1016 |
| 1587 | ACAGAAG CUGAUGAGGCCGAAAGGCCGAA AGUUGGG | 1017 |
| 1595 | UCUUCAG CUGAUGAGGCCGAAAGGCCGAA ACAGAAG | 1018 |
| 1595 | UCUUCAG CUGAUGAGGCCGAAAGGCCGAA ACAGAAG | 1019 |
| 1595 | UCUUCAG CUGAUGAGGCCGAAAGGCCGAA ACAGAAG | 1020 |
| 1624 | CCCAGGG CUGAUGAGGCCGAAAGGCCGAA AUGCUGC | 1021 |
| 1594 | CAGCUGG CUGAUGAGGCCGAAAGGCCGAA AUCCGAA | 1022 |
| 1787 | CAGGCUA CUGAUGAGGCCGAAAGGCCGAA AGCCAGG | 1023 |
| 1788 | GCAGGCU CUGAUGAGGCCGAAAGGCCGAA AAGCCAG | 1024 |
| 1816 | CCAGAGA CUGAUGAGGCCGAAAGGCCGAA AUUUAGC | 1025 |
| 1818 | AGCCAGA CUGAUGAGGCCGAAAGGCCGAA AGAUUUA | 1026 |
| 1818 | AGCCAGA CUGAUGAGGCCGAAAGGCCGAA AGAUUUA | 1027 |
| 1828 | AGAGAGA CUGAUGAGGCCGAAAGGCCGAA ACAGCCA | 1028 |
| 1847 | AUUCGUU CUGAUGAGGCCGAAAGGCCGAA ACUUGAG | 1029 |

TABLE VI

Human CETP Hairpin Ribozyme and Substrate Sequence

| nt. | Ribozyme Sequence | Sequence ID No. |
|---|---|---|
| 27 | UUCCGGGC AGAA GGGUCU ACCAGAGAAACACACGUUGUGGUACAUUACCUGGUA | 1030 |
| 30 | CUCUUCCG AGAA GCAGGG ACCAGAGAAACACACGUUGUGGUACAUUACCUGGUA | 1031 |
| 96 | GUGGCCCG AGAA GUUCAG ACCAGAGAAACACACGUUGUGGUACAUUACCUGGUA | 1032 |
| 119 | GGUUAUCA AGAA GUGGUG ACCAGAGAAACACACGUUGUGGUACAUUACCUGGUA | 1033 |
| 145 | AGGGUCAG AGAA GUGGCA ACCAGAGAAACACACGUUGUGGUACAUUACCUGGUA | 1034 |
| 150 | GGGCCAGG AGAA GGACUG ACCAGAGAAACACACGUUGUGGUACAUUACCUGGUA | 1035 |
| 162 | CAUUGCCC AGAA GGGCCA ACCAGAGAAACACACGUUGUGGUACAUUACCUGGUA | 1036 |
| 182 | GCCUUUGG AGAA GGCAUG ACCAGAGAAACACACGUUGUGGUACAUUACCUGGUA | 1037 |
| 235 | ACCAGGAG AGAA GGCUUG ACCAGAGAAACACACGUUGUGGUACAUUACCUGGUA | 1038 |
| 276 | GGAAGGCG AGAA GGAUCA ACCAGAGAAACACACGUUGUGGUACAUUACCUGGUA | 1039 |
| 280 | CGCUGGAA AGAA GUCUGG ACCAGAGAAACACACGUUGUGGUACAUUACCUGGUA | 1040 |
| 369 | AGUGGCUG AGAA GGAUGU ACCAGAGAAACACACGUUGUGGUACAUUACCUGGUA | 1041 |
| 490 | AGCCACCA AGAA GUGGUG ACCAGAGAAACACACGUUGUGGUACAUUACCUGGUA | 1042 |
| 513 | AGUCAAUG AGAA GAUCAA ACCAGAGAAACACACGUUGUGGUACAUUACCUGGUA | 1043 |
| 552 | GUGUGUUG AGAA GGAGGU ACCAGAGAAACACACGUUGUGGUACAUUACCUGGUA | 1044 |
| 564 | CACAGGUC AGAA GUGUGU ACCAGAGAAACACACGUUGUGGUACAUUACCUGGUA | 1045 |
| 567 | AGUCACAG AGAA GCUGUG ACCAGAGAAACACACGUUGUGGUACAUUACCUGGUA | 1046 |
| 591 | GGGCAUCG AGAA GCACUC ACCAGAGAAACACACGUUGUGGUACAUUACCUGGUA | 1047 |
| 595 | UCAGGGGC AGAA GUCCGC ACCAGAGAAACACACGUUGUGGUACAUUACCUGGUA | 1048 |
| 604 | AGGUAGCA AGAA GGGGCA ACCAGAGAAACACACGUUGUGGUACAUUACCUGGUA | 1049 |
| 615 | UAUGGAAA AGAA GGUAGC ACCAGAGAAACACACGUUGUGGUACAUUACCUGGUA | 1050 |
| 630 | GAUGCAGG AGAA GCUUAU ACCAGAGAAACACACGUUGUGGUACAUUACCUGGUA | 1051 |
| 675 | UUGUGAAC AGAA GCUUGA ACCAGAGAAACACACGUUGUGGUACAUUACCUGGUA | 1052 |
| 678 | AAUUUGUG AGAA GCUGCU ACCAGAGAAACACACGUUGUGGUACAUUACCUGGUA | 1053 |
| 726 | CUUUGCAG AGAA GUCCCU ACCAGAGAAACACACGUUGUGGUACAUUACCUGGUA | 1054 |
| 766 | UGGACAAA AGAA GCCAUG ACCAGAGAAACACACGUUGUGGUACAUUACCUGGUA | 1055 |
| 802 | AUGUCUCC AGAA GAAAGG ACCAGAGAAACACACGUUGUGGUACAUUACCUGGUA | 1056 |
| 853 | AGGUAGGA AGAA GUGAUG ACCAGAGAAACACACGUUGUGGUACAUUACCUGGUA | 1057 |
| 942 | AGUCCCCC AGAA GUGUGG ACCAGAGAAACACACGUUGUGGUACAUUACCUGGUA | 1058 |
| 1025 | GAGCAUGA AGAA GCCAUC ACCAGAGAAACACACGUUGUGGUACAUUACCUGGUA | 1059 |
| 1037 | UCCCAUCA AGAA GAGCAU ACCAGAGAAACACACGUUGUGGUACAUUACCUGGUA | 1060 |
| 1041 | CGUCUCCC AGAA GGCUGA ACCAGAGAAACACACGUUGUGGUACAUUACCUGGUA | 1061 |
| 1121 | GCUGGGGA AGAA GCCGAC ACCAGAGAAACACACGUUGUGGUACAUUACCUGGUA | 1062 |
| 1147 | AGGCAGUG AGAA GUGACU ACCAGAGAAACACACGUUGUGGUACAUUACCUGGUA | 1063 |
| 1154 | CAUCUUGA AGAA GUGGAC ACCAGAGAAACACACGUUGUGGUACAUUACCUGGUA | 1064 |
| 1240 | UGUUGCUG AGAA GGGCGU ACCAGAGAAACACACGUUGUGGUACAUUACCUGGUA | 1065 |

TABLE VI-continued

Human CETP Hairpin Ribozyme and Substrate Sequence

| | | Sequence ID No. |
|---|---|---|
| 1291 | GAGGCCUG AGAA GUAGUC ACCAGAGAAACACACGUUGUGGUACAUUACCUGGUA | 1066 |
| 1344 | UUGGUGUA AGAA GGAAAU ACCAGAGAAACACACGUUGUGGUACAUUACCUGGUA | 1067 |
| 1360 | AAGUUGGA AGAA GUCUUU ACCAGAGAAACACACGUUGUGGUACAUUACCUGGUA | 1068 |
| 1382 | GGACUCGG AGAA GCUCUC ACCAGAGAAACACACGUUGUGGUACAUUACCUGGUA | 1069 |
| 1423 | AUGCCCAC AGAA GUGAUC ACCAGAGAAACACACGUUGUGGUACAUUACCUGGUA | 1070 |
| 1452 | CUACCUCG AGAA GAGACA ACCAGAGAAACACACGUUGUGGUACAUUACCUGGUA | 1071 |
| 1471 | UUCAUGAG AGAA GUAAAC ACCAGAGAAACACACGUUGUGGUACAUUACCUGGUA | 1072 |
| 1545 | UCUGCAGC AGAA GGAAGC ACCAGAGAAACACACGUUGUGGUACAUUACCUGGUA | 1073 |
| 1548 | CCAUCUGC AGAA GGAAGC ACCAGAGAAACACACGUUGUGGUACAUUACCUGGUA | 1074 |
| 1554 | CAAAGUCC AGAA GCAGCA ACCAGAGAAACACACGUUGUGGUACAUUACCUGGUA | 1075 |
| 1581 | AAUCCACC AGAA GGUGCU ACCAGAGAAACACACGUUGUGGUACAUUACCUGGUA | 1076 |
| 1669 | AGGGUUCC AGAA GUGAGC ACCAGAGAAACACACGUUGUGGUACAUUACCUGGUA | 1077 |

| nt. | Substrate | Sequence ID No. |
|---|---|---|
| 27 | AGACCCU GCU GCCCGGAA | 1078 |
| 30 | CCCUGCU GCC CGGAAGAG | 1079 |
| 96 | CUGAACG GCU CGGGCCAC | 1080 |
| 119 | CACCACU GCC UGAUAACC | 1081 |
| 145 | UGCCACA GUC CUGACCCU | 1082 |
| 150 | CAGUCCU GAC CCUGGCCC | 1083 |
| 162 | UGGCCCU GCU GGGCAAUG | 1084 |
| 182 | CAUGCCU GCU CCAAAGGC | 1085 |
| 235 | CAAGCCU GCC CUCCUGGU | 1086 |
| 276 | UGAUCCA GAC CGCCUUCC | 1087 |
| 280 | CCAGACC GCC UUCCAGCG | 1088 |
| 369 | ACAUCCA GAU CAGCCACU | 1089 |
| 490 | CACCACU GCC UGGUGGCU | 1090 |
| 513 | UUGAUCA GUC CAUUGACU | 1091 |
| 552 | ACCUCCA GAU CAACACAC | 1092 |
| 564 | ACACACA GCU GACCUGUG | 1093 |
| 567 | CACAGCU GAC CUGUGACU | 1094 |
| 591 | GAGUGCG GAC CGAUGCCC | 1095 |
| 595 | GCGGACC GAU GCCCCUGA | 1096 |
| 604 | UGCCCCU GAC UGCUACCU | 1097 |
| 615 | GCUACCU GUC UUUCCAUA | 1098 |
| 630 | AUAAGCU GCU CCUGCAUC | 1099 |
| 675 | UCAAGCA GCU GUUCACAA | 1100 |
| 678 | AGCAGCU GUU CACAAAUU | 1101 |
| 726 | AGGGACA GAU CUGCAAAG | 1102 |
| 766 | CAUGGCC GAU UUUGUCCA | 1103 |
| 802 | CCUUUCA GAU GGAGACAU | 1104 |
| 853 | CAUCACA GAU GGAGACAU | 1105 |
| 942 | CAUCACA GCC UCCUACCU | 1106 |
| 1025 | GAUGGCC GCC UCAUGCUC | 1107 |
| 1037 | AUGCUCA GCC UGAUGGGA | 1108 |
| 1041 | UCAGCCU GAU GGGAGACG | 1109 |
| 1121 | GUCGGCG GCU UCCCCAGC | 1110 |
| 1147 | AGUCACC GUC CACUGCCU | 1111 |
| 1154 | GUCCACU GCC UCAAGAUG | 1112 |
| 1240 | ACGCCCA GAC CAGCAACA | 1113 |
| 1291 | GACUACC GUC CAGGCCUC | 1114 |
| 1344 | AUUUCCA GAU UACACCAA | 1115 |
| 1360 | AAAGACU GUU UCCAACUU | 1116 |
| 1381 | GAGAGCA GCU CCGAGUCC | 1117 |
| 1423 | GAUCACC GCU GUGGGCAU | 1118 |
| 1452 | UGUCUCG GCU CGAGGUAG | 1119 |
| 1471 | GUUUACA GCC CUCAUGAA | 1120 |
| 1545 | GCUUCCU GCU GCUGCAGA | 1121 |
| 1548 | UCCUGCU GCU GCAGAUGG | 1122 |
| 1554 | UGCUGCA GAU GGACUUUG | 1123 |
| 1581 | AGCACCU GCU GGUGGAUU | 1124 |
| 1669 | GCUCACA GCU GGAACCCU | 1125 |

TABLE VII

Rabbit CEPT Hairpin Ribozyme and Substrate Sequence

| Position | Ribozyme Sequence | Seq. ID No. |
|---|---|---|
| 57 | ACCAAGAG AGAA GGCUUG ACCAGAGAAACACACGUUGUGGUACAUUACCUGGUA | 1126 |
| 98 | GGAAGGCC AGAA GGACCA ACCAGAGAAACACACGUUGUGGUACAUUACCUGGUA | 1127 |

TABLE VII-continued

Rabbit CEPT Hairpin Ribozyme and Substrate Sequence

| | | |
|---|---|---|
| 102 | CGCUGGAA AGAA GUCUGG ACCAGAGAAACACACGUUGUGGUACAUUACCUGGUA | 1128 |
| 126 | CCGCUGAC AGAA GGAUAG ACCAGAGAAACACACGUUGUGGUACAUUACCUGGUA | 1129 |
| 160 | CUUGACCC AGAA GAGGAG ACCAGAGAAACACACGUUGUGGUACAUUACCUGGUA | 1130 |
| 191 | GGUGGCUG AGAA GGAGGU ACCAGAGAAACACACGUUGUGGUACAUUACCUGGUA | 1131 |
| 203 | UGGCGAUG AGAA GGUGGC ACCAGAGAAACACACGUUGUGGUACAUUACCUGGUA | 1132 |
| 335 | AGUCGACA AGAA GAUUGA ACCAGAGAAACACACGUUGUGGUACAUUACCUGGUA | 1133 |
| 339 | UCGAAGUC AGAA GACUGA ACCAGAGAAACACACGUUGUGGUACAUUACCUGGUA | 1134 |
| 374 | CUGUGUUG AGAA GGAGGU ACCAGAGAAACACACGUUGUGGUACAUUACCUGGUA | 1135 |
| 389 | CGUCGCAG AGAA GCUCUG ACCAGAGAAACACACGUUGUGGUACAUUACCUGGUA | 1136 |
| 426 | AGGUAGCA AGAA GGGGCA ACCAGAGAAACACACGUUGUGGUACAUUACCUGGUA | 1137 |
| 452 | GGUGCAGG AGAA GUUUAU ACCAGAGAAACACACGUUGUGGUACAUUACCUGGUA | 1138 |
| 497 | UUGUGAAG AGAA GCUUGA ACCAGAGAAACACACGUUGUGGUACAUUACCUGGUA | 1139 |
| 533 | GCUUCAGA AGAA GCUUCA ACCAGAGAAACACACGUUGUGGUACAUUACCUGGUA | 1140 |
| 588 | UGGACAAA AGAA GCCAUG ACCAGAGAAACACACGUUGUGGUACAUUACCUGGUA | 1141 |
| 599 | CGGCCCUC AGAA GGACAA ACCAGAGAAACACACGUUGUGGUACAUUACCUGGUA | 1142 |
| 624 | AUGUCUCC AGAA GAGAGG ACCAGAGAAACACACGUUGUGGUACAUUACCUGGUA | 1143 |
| 755 | GAAGACCG AGAA GGAAGG ACCAGAGAAACACACGUUGUGGUACAUUACCUGGUA | 1144 |
| 760 | CCCCAGAA AGAA GGGCGG ACCAGAGAAACACACGUUGUGGUACAUUACCUGGUA | 1145 |
| 801 | AGCACUUG AGAA GAGAAC ACCAGAGAAACACACGUUGUGGUACAUUACCUGGUA | 1146 |
| 831 | UCCUGGAA AGAA GCCCUG ACCAGAGAAACACACGUUGUGGUACAUUACCUGGUA | 1147 |
| 847 | GAGCACGA AGAA GCCCUC ACCAGAGAAACACACGUUGUGGUACAUUACCUGGUA | 1148 |
| 859 | CCCUGUCA AGAA GAGCAC ACCAGAGAAACACACGUUGUGGUACAUUACCUGGUA | 1149 |
| 972 | AGGCAGUG AGAA GCUACC ACCAGAGAAACACACGUUGUGGUACAUUACCUGGUA | 1150 |
| 979 | CACCUUAA AGAA GUGGAC ACCAGAGAAACACACGUUGUGGUACAUUACCUGGUA | 1151 |
| 1035 | GUCACGGC AGAA GAAGAA ACCAGAGAAACACACGUUGUGGUACAUUACCUGGUA | 1152 |
| 1051 | GCGGGGGA AGAA GAACGU ACCAGAGAAACACACGUUGUGGUACAUUACCUGGUA | 1153 |
| 1060 | GCCAUCUG AGAA GGGGAA ACCAGAGAAACACACGUUGUGGUACAUUACCUGGUA | 1154 |
| 1065 | UCUCGGCC AGAA GGGCGG ACCAGAGAAACACACGUUGUGGUACAUUACCUGGUA | 1155 |
| 1116 | GAGGCCUG AGAA GUGGUG ACCAGAGAAACACACGUUGUGGUACAUUACCUGGUA | 1156 |
| 1198 | AUUUGCUG AGAA GCCUGC ACCAGAGAAACACACGUUGUGGUACAUUACCUGGUA | 1157 |
| 1242 | AGGUUGGA AGAA GCCUUA ACCAGAGAAACACACGUUGUGGUACAUUACCUGGUA | 1158 |
| 1253 | GGCUCUCA AGAA GGUUGG ACCAGAGAAACACACGUUGUGGUACAUUACCUGGUA | 1159 |
| 1264 | GGACUCGG AGAA GCUCUC ACCAGAGAAACACACGUUGUGGUACAUUACCUGGUA | 1160 |
| 1291 | GAUCAGGG AGAA GAGAGA ACCAGAGAAACACACGUUGUGGUACAUUACCUGGUA | 1161 |
| 1298 | CCGUGGCG AGAA GGGAGC ACCAGAGAAACACACGUUGUGGUACAUUACCUGGUA | 1162 |
| 1334 | CCACCUCG AGAA GAGACA ACCAGAGAAACACACGUUGUGGUACAUUACCUGGUA | 1163 |
| 1353 | UUCAUGAG AGAA GUGAAC ACCAGAGAAACACACGUUGUGGUACAUUACCUGGUA | 1164 |
| 1423 | CAGCAGCA AGAA GCCAUC ACCAGAGAAACACACGUUGUGGUACAUUACCUGGUA | 1165 |
| 1427 | UCUGCAGC AGAA GGCAGC ACCAGAGAAACACACGUUGUGGUACAUUACCUGGUA | 1166 |
| 1430 | CCAUCUGC AGAA GCAGGC ACCAGAGAAACACACGUUGUGGUACAUUACCUGGUA | 1167 |
| 1436 | CGAAGUCC AGAA GCAGCA ACCAGAGAAACACACGUUGUGGUACAUUACCUGGUA | 1168 |
| 1448 | CUUGGGAA AGAA GAAGUC ACCAGAGAAACACACGUUGUGGUACAUUACCUGGUA | 1169 |
| 1463 | AAUCCACC AGAA GGUGCU ACCAGAGAAACACACGUUGUGGUACAUUACCUGGUA | 1170 |
| 1521 | GCGGAGAC AGAA GCGUGU ACCAGAGAAACACACGUUGUGGUACAUUACCUGGUA | 1171 |
| 1530 | CCCCGAUG AGAA GAGACG ACCAGAGAAACACACGUUGUGGUACAUUACCUGGUA | 1172 |
| 1592 | GUCUUCAG AGAA GAAGGA ACCAGAGAAACACACGUUGUGGUACAUUACCUGGUA | 1173 |
| 1690 | CAGCUGGG AGAA GGAGCA ACCAGAGAAACACACGUUGUGGUACAUUACCUGGUA | 1174 |
| 1697 | UAGCAGGC AGAA GGGAUC ACCAGAGAAACACACGUUGUGGUACAUUACCUGGUA | 1175 |
| 1700 | CGUUAGCA AGAA GCUGGG ACCAGAGAAACACACGUUGUGGUACAUUACCUGGUA | 1176 |
| 1727 | ACCAGCAC AGAA GCUCCC ACCAGAGAAACACACGUUGUGGUACAUUACCUGGUA | 1177 |
| 1763 | GGACCUCA AGAA GGGUCU ACCAGAGAAACACACGUUGUGGUACAUUACCUGGUA | 1178 |
| 1793 | ACUCACUG AGAA GGCUAA ACCAGAGAAACACACGUUGUGGUACAUUACCUGGUA | 1179 |
| 1825 | CAGAGAGA AGAA GCCAGA ACCAGAGAAACACACGUUGUGGUACAUUACCUGGUA | 1180 |
| 1835 | ACUUGAGA AGAA GAGAGA ACCAGAGAAACACACGUUGUGGUACAUUACCUGGUA | 1181 |

| nt. Position | Substrate | Seq. ID No. |
|---|---|---|
| 57 | CAAGCCC GCC CUCUUGGU | 1182 |
| 98 | UGGUCCA GAC GGCCUUCC | 1883 |
| 102 | CCAGACG GCC UUCCAGCG | 1884 |
| 126 | CUAUCCG GAC GUCAGCGG | 1185 |
| 160 | CUCCUCG GCC GGGUCAAG | 1186 |
| 191 | ACCUCCA GAU CAGCCACC | 1187 |
| 203 | GCCACCU GUC CAUCGCCA | 1188 |
| 335 | UCAAUCA GUC UGUCGACU | 1189 |
| 339 | UCAGUCU GUC GACUUCGA | 1190 |
| 374 | ACCUCCA GAU CAACACAG | 1191 |
| 389 | CAGAGCU GAC CUGCGACG | 1192 |
| 426 | UGCCCCC GAC UGCUACCU | 1193 |
| 452 | AUAAACU GCU CCUGCACC | 1194 |
| 497 | UCAAGCA GCU CUUCACAA | 1195 |
| 533 | UGAAGCU GAU UCUGAAGC | 1196 |
| 588 | CAUGGCU GAC UUUGUCCA | 1197 |
| 599 | UUGUCCA GAC GAGGGCCG | 1198 |
| 624 | CCUCUCA GAU GGAGACAU | 1199 |
| 755 | CCUUCCC GCC CGGUCUUC | 1200 |

TABLE VII-continued

Rabbit CEPT Hairpin Ribozyme and Substrate Sequence

| | | |
|---|---|---|
| 760 | CCGCCCG GUC UUCUGGGG | 1201 |
| 801 | GUUCUCC GAU CAAGUGCU | 1202 |
| 831 | CAGGGCC GCC UUCCAGGA | 1203 |
| 847 | GAGGGCC GUC UCGUGCUC | 1204 |
| 859 | GUGCUCA GCC UGACAGGG | 1205 |
| 972 | GGUAGCC GUC CACUGCCU | 1206 |
| 979 | GUCCACU GCC UUAAGGUG | 1207 |
| 1035 | UUCUUCC GUC GCCGUGAC | 1208 |
| 1051 | ACGUUCC GCU UCCCCCGC | 1209 |
| 1060 | UUCCCCC GCC CAGAUGGC | 1210 |
| 1065 | CCGCCCA GAU GGCCGAGA | 1211 |
| 1116 | CACCACC GUC CAGGCCUC | 1212 |
| 1198 | GCAGGCA GCU CAGCAAAU | 1213 |
| 1242 | UAAGGCU GUU UCCAACCU | 1214 |
| 1253 | CCAACCU GAC UGAGAGCC | 1215 |
| 1264 | GAGAGCC GCU CCGAGUCC | 1216 |
| 1291 | UCUCUCC GCU CCCUGAUC | 1217 |
| 1298 | GCUCCCU GAU CGCCACGG | 1218 |
| 1334 | UGUCUCG GCU CGAGGUGG | 1219 |
| 1353 | GUUCACA GCC CUCAUGAA | 1220 |
| 1423 | GAUGGCU GCC UGCUGCUG | 1221 |
| 1427 | GCUGCCU GCU GCUGCAGA | 1222 |
| 1430 | GCCUGCU GCU GCAGAUGG | 1223 |
| 1436 | UGCUGCA GAU GGACUUCG | 1224 |
| 1447 | GACUUCG GUU UUCCCAAG | 1225 |
| 1463 | AGCACCU GCU GGUGGAUU | 1226 |
| 1521 | ACACGCU GAC GUCUCCGC | 1227 |
| 1530 | CGUCUCC GCC CAUCGGGG | 1228 |
| 1592 | UCCUUCU GUC CUGAAGAC | 1229 |
| 1690 | UGCUCCG GAU CCCAGCUG | 1230 |
| 1697 | GAUCCCA GCU GCCUGCUA | 1231 |
| 1700 | CCCAGCU GCC UGCUAACG | 1232 |
| 1727 | GGGAGCA GCC GUGCUGGU | 1233 |
| 1763 | AGACCCA GAC UGAGGUCC | 1234 |
| 1793 | UUAGCCU GCC CAGUGAGU | 1235 |
| 1825 | UCUGGCU GUC UCUCUCUG | 1236 |
| 1835 | UCUCUCU GCC UCUCAAGU | 1237 |

We claim:

1. An enzymatic RNA molecule which specifically cleaves RNA produced from the gene encoding cholesterol ester transfer protein (CETP).

2. The enzymatic RNA molecule of claim 1, wherein said RNA molecule is in a hammerhead motif.

3. The enzymatic RNA molecule of claim 5, wherein the binding arms of said enzymatic RNA molecule comprises sequences complementary to any of sequences defined as Seq ID Nos 2–258.

4. The enzymatic RNA molecule of claim 1, wherein said RNA molecule is in a hairpin, hepatitis Delta virus, group I intron, VS nucleic acid or RNaseP RNA motif.

5. The hairpin enzymatic RNA molecule of claim 4, wherein said hairpin RNA molecule comprises sequences complementary any of sequences defined as Seq ID Nos 1078–1125.

6. The enzymatic RNA molecule of claim 1, wherein said enzymatic RNA molecule comprises at least one sugar modification.

7. The enzymatic RNA molecule of claim 1, wherein said RNA comprises between 12 and 100 bases complementary to the RNA of said region.

8. The enzymatic RNA molecule of claim 1, wherein said RNA molecule comprises between 14 and 24 bases complementary to the RNA of said region.

9. The Enzymatic RNA molecule of claim 1, wherein said enzymatic RNA molecule comprises any of sequences shown as Seq ID Nos 259–515 and 1030–1077.

10. A mammalian cell including an enzymatic RNA molecule of claim 1 in vitro.

11. The mammalian cell of claim 10, wherein said cell is a human cell.

12. An expression vector comprising nucleic acid encoding the enzymatic RNA molecule of claim 1, in a manner which allows expression and/or delivery of that enzymatic RNA molecule within a mammalian cell in vitro.

13. A mammalian cell including the expression vector of claim 12 in vitro.

14. The mammalian cell of claim 13, wherein said cell is a human cell.

* * * * *